US012312409B2

(12) United States Patent
You et al.

(10) Patent No.: US 12,312,409 B2
(45) Date of Patent: May 27, 2025

(54) BISPECIFIC CD137-BINDING ANTIBODIES FOR T-CELL ACTIVATION

(71) Applicant: AP Biosciences, Inc., Taipei (TW)

(72) Inventors: Jhong-Jhe You, Taipei (TW); Ching-Hsuan Hsu, Taoyaun (TW); Po-Lin Huang, Taipei (TW); Jeng-Horng Her, San Jose, CA (US)

(73) Assignee: AP Biosciences, Inc., Taipei (TW)

( * ) Notice: Subject to any disclaimer, the term of this patent is extended or adjusted under 35 U.S.C. 154(b) by 0 days.

(21) Appl. No.: 18/222,763

(22) Filed: Jul. 17, 2023

(65) Prior Publication Data

US 2024/0026018 A1    Jan. 25, 2024

Related U.S. Application Data

(62) Division of application No. 16/911,052, filed on Jun. 24, 2020, now Pat. No. 11,725,058.

(60) Provisional application No. 62/953,302, filed on Dec. 24, 2019, provisional application No. 62/866,699, filed on Jun. 26, 2019.

(51) Int. Cl.
    *C07K 16/28*    (2006.01)
    *A61K 39/00*    (2006.01)

(52) U.S. Cl.
    CPC ...... *C07K 16/2878* (2013.01); *C07K 16/2827* (2013.01); *A61K 2039/505* (2013.01); *C07K 2317/31* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/622* (2013.01); *C07K 2317/75* (2013.01); *C07K 2317/76* (2013.01)

(58) Field of Classification Search
    None
    See application file for complete search history.

(56) References Cited

U.S. PATENT DOCUMENTS

| 7,973,140 B2 | 7/2011 | Green et al. |
| 8,629,250 B2 | 1/2014 | Sasu et al. |
| 9,880,160 B2 | 1/2018 | Chen et al. |

(Continued)

FOREIGN PATENT DOCUMENTS

| CN | 106243223 A | 12/2016 |
| EP | 3470428 A1 | 4/2019 |

(Continued)

OTHER PUBLICATIONS

Chen et al., "Enhancement and Destruction of Antibody Function by Somatic Mutation: Unequal Occurrence is Controlled by V Gene Combinatorial Associations," *EMBO J.* (1995), 14(12):2784-2794, Oxford University Press.

(Continued)

*Primary Examiner* — Claire Kaufman
(74) *Attorney, Agent, or Firm* — DLA Piper LLP (US)

(57) ABSTRACT

Antibodies that include an antigen binding region that binds to CD137 are provided herein. Also provided herein are bispecific antibodies that include a first antigen binding region that binds to CD137 and a second antigen binding region that binds to an immune checkpoint molecule, an immune stimulatory molecule, or a tumor antigen. Pharmaceutical compositions that include the antibodies and methods of treating cancer are provided.

9 Claims, 35 Drawing Sheets

Specification includes a Sequence Listing.

(56) References Cited

U.S. PATENT DOCUMENTS

| | | | |
|---|---|---|---|
| 10,131,704 | B2 | 11/2018 | Marasco et al. |
| 10,233,251 | B2 | 3/2019 | Gray et al. |
| 10,688,178 | B2 * | 6/2020 | Kumanogoh .......... C12N 15/09 |
| 10,906,983 | B2 | 2/2021 | Frye et al. |
| 11,180,568 | B2 | 11/2021 | Gray et al. |
| 11,274,155 | B2 * | 3/2022 | Jiang ................ G01N 33/57492 |
| 11,685,786 | B2 | 6/2023 | Geuijen et al. |
| 2006/0246071 | A1 | 11/2006 | Green et al. |
| 2012/0039807 | A1 | 2/2012 | Freimoser-Grundschober et al. |
| 2013/0004501 | A1 | 1/2013 | Towne et al. |
| 2013/0177572 | A1 | 7/2013 | Chen et al. |
| 2014/0065166 | A1 | 3/2014 | Broder et al. |
| 2014/0113831 | A1 | 4/2014 | Chen et al. |
| 2016/0244528 | A1 | 8/2016 | Gray et al. |
| 2017/0198050 | A1 | 7/2017 | Eckelman et al. |
| 2018/0346601 | A1 | 12/2018 | Dettling et al. |
| 2019/0161554 | A1 | 5/2019 | Gray et al. |
| 2020/0017595 | A1 | 1/2020 | Geuijen et al. |

FOREIGN PATENT DOCUMENTS

| | | | |
|---|---|---|---|
| EP | 3708582 A1 | 9/2020 | |
| WO | WO-2015164865 A1 * | 10/2015 | ............. A61K 39/42 |
| WO | WO 2017/220988 A1 | 12/2017 | |
| WO | WO 2018/091740 A2 | 5/2018 | |
| WO | WO 2018/156740 A1 | 8/2018 | |
| WO | WO 2019/027754 A1 | 2/2019 | |
| WO | WO 2019/089753 A2 | 5/2019 | |
| WO | WO 2019/091436 A1 | 5/2019 | |

OTHER PUBLICATIONS

Herold et al., "Determinants of the Assembly and Function of Antibody Variable Domains," *Sci. Rep.* (2017), 7:12276.

Kranz and Voss, Jr., "Restricted Reassociation of Heavy and Light Chains from Hapten-Specific Monoclonal Antibodies," *Proc. Natl. Acad. Sci. USA* (1981), 78(9):5807-5811.

Lamminmaki and Kankare, "Crystal Structure of a Recombinant Anti-Estradiol Fab fragment in Complex with 17Beta-Estradiol," *J. Biol. Chem.* (2001), 276(39):36687-36694, The American Society for Biochemistry and Molecular Biology, Inc.

MacCallum et al. "Antibody-Antigen Interactions: Contact Analysis and Binding Site Topography," *J. Mol. Biol.* (1996) 262:732-745, Academic Press Limited.

Nezlin, R.S., "Biochemistry of Antibodies," (1970), p. 160, Plenum Press, New York.

PCT International Search Report and Written Opinion in International Application No. PCT/US2020/039218 dated Nov. 24, 2020, 19 pages.

Su et al., "Immunoglobulin Lambda Variable Region, Partial [*Homo sapiens*]," *GenBank: CAP74504*, Jul. 26, 2016, 1 page.

Titani et al., "THE Amino Acid Sequence of a Lambda Type Bence-Jones Protein," *J. Biol. Chem.* (1970), 245(8):2171-2176.

EP Extended Search Report in European Application No. 20831405. 4, dated Oct. 10, 2023, 20 pages.

CN Office Action in Chinese Application No. 202080045146.1, dated Feb. 6, 2024, 19 pages (with English translation).

Compte et al., "A tumor-targeted trimeric 4-1BB-agonistic antibody induces potent anti-tumor immunity without systemic toxicity", Nature Communications, Nov. 2018, 9(1): 1-13.

EP Partial Supplementary Search Report in European Application No. 20831405, dated Jun. 2, 2023, 17 pages.

TW Office Action in Taiwanese Application No. 109121449, dated Mar. 18, 2024, 19 pages (with English translation).

* cited by examiner

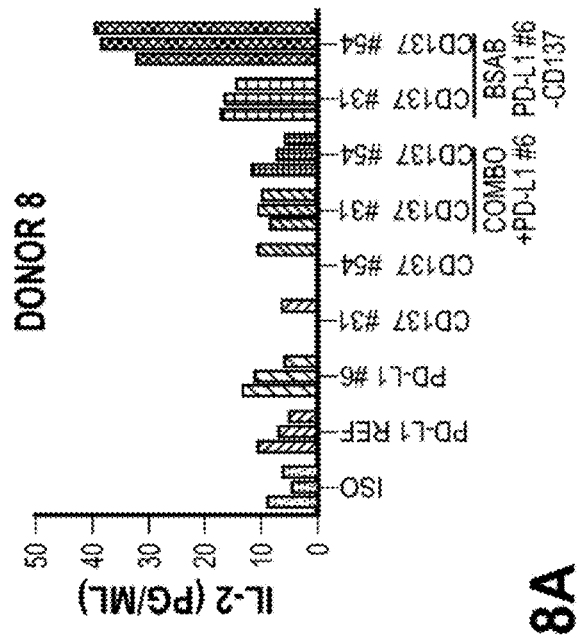
FIG. 18A
FIG. 18B
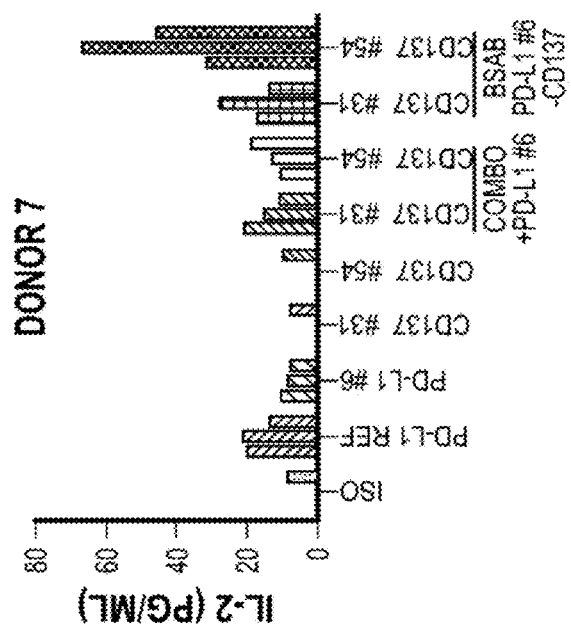
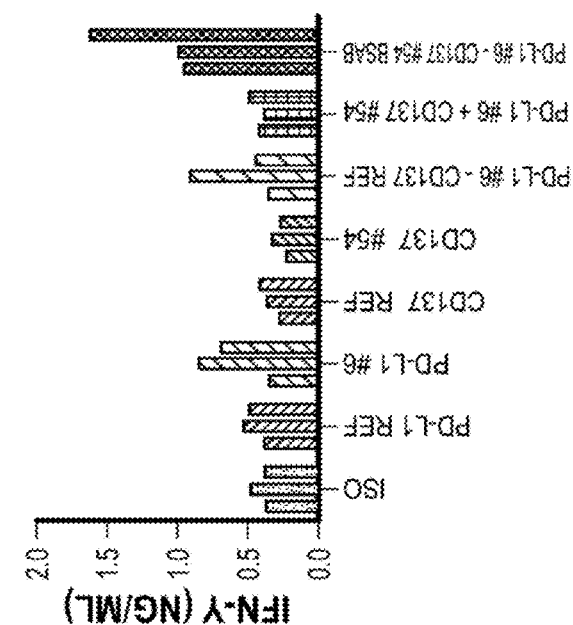

| | UNIT | 25 mg/kg FEMALE | 25 mg/kg MALE | 5 mg/kg FEMALE | 5 mg/kg MALE |
|---|---|---|---|---|---|
| CMAX | µg/ml | 507.88 | 403.85 | 96.24 | 95.78 |
| T1/2 | h | 91.03 | 82.43 | 45.31 | 51.83 |
| AUC 0-T | µG/ML*H | 35414.62 | 32919.44 | 4837.25 | 4647.08 |
| CL_OBS | (mg/kg)/(µg/ml)h | 0.0004748 | 0.0005284 | 0.0046397 | 0.0046334 |
| VSS_OBS | (mg/kg)/(µg/ml) | 0.0607443 | 0.0631104 | 0.2785128 | 0.3257398 |

SEQUENCE LISTING

```
Sequence total quantity: 46
SEQ ID NO: 1                    moltype = AA  length = 124
FEATURE                         Location/Qualifiers
REGION                          1..124
                                note = Synthetic
REGION                          1..124
                                note = misc_feature - Anti-CD137 clone 15 heavy chain
source                          1..124
                                mol_type = protein
                                organism = synthetic construct
SEQUENCE: 1
QVQLVQSGAE VKKPGSSVKV SCKASGGTFS SYAISWVRQA PGQGLEWMGR IIPILGIANY    60
AQKFQGRVTI TADKSTSTAY MELSSLRSED TAVYYCASDL YQLLFPYYYG MDVWGQGTTV   120
TVSS                                                                124

SEQ ID NO: 2                    moltype = AA  length = 222
FEATURE                         Location/Qualifiers
REGION                          1..222
                                note = Synthetic
REGION                          1..222
                                note = misc_feature - Anti-CD137 clone 15 light chain
source                          1..222
                                mol_type = protein
                                organism = synthetic construct
SEQUENCE: 2
QLVLTQPPSA SASLGASVTL TCTLSSGYSN YKVDWYQQRP GKGPRFVMRV GTGGIVGSKG    60
DGIPDRFSVL GSGLNRYLTI KNIQEEDESD YHCGADHGSG SNLFWVFGGG TKLTVLGQPK   120
AAPSVTLFPP SSEELQANKA TLVCLISDFY PGAVTVAWKA DSSPVKAGVE TTTPSKQSNN   180
KYAASSYLSL TPEQWKSHRS YSCQVTHEGS TVEKTVAPTE CS                      222

SEQ ID NO: 3                    moltype = AA  length = 7
FEATURE                         Location/Qualifiers
REGION                          1..7
                                note = Synthetic
REGION                          1..7
                                note = misc_feature - CDR-H1 of anti-CD137 clone 15
source                          1..7
                                mol_type = protein
                                organism = synthetic construct
SEQUENCE: 3
GGTFSSY                                                               7

SEQ ID NO: 4                    moltype = AA  length = 6
FEATURE                         Location/Qualifiers
REGION                          1..6
                                note = Synthetic
REGION                          1..6
                                note = misc_feature - CDR-H2 of anti-CD137 clone 15
source                          1..6
                                mol_type = protein
                                organism = synthetic construct
SEQUENCE: 4
IPILGI                                                                6

SEQ ID NO: 5                    moltype = AA  length = 15
FEATURE                         Location/Qualifiers
REGION                          1..15
                                note = Synthetic
REGION                          1..15
                                note = misc_feature - CDR-H3 of anti-CD137 clone 15
source                          1..15
                                mol_type = protein
                                organism = synthetic construct
SEQUENCE: 5
DLYQLLFPYY YGMDV                                                     15

SEQ ID NO: 6                    moltype = AA  length = 12
FEATURE                         Location/Qualifiers
REGION                          1..12
                                note = Synthetic
REGION                          1..12
                                note = misc_feature - CDR-L1 of anti-CD137 clone 15
source                          1..12
                                mol_type = protein
                                organism = synthetic construct
SEQUENCE: 6
TLSSGYSNYK VD                                                        12
```

```
SEQ ID NO: 7                moltype = AA  length = 12
FEATURE                     Location/Qualifiers
REGION                      1..12
                            note = Synthetic
REGION                      1..12
                            note = misc_feature - CDR-L2 of anti-CD137 clone 15
source                      1..12
                            mol_type = protein
                            organism = synthetic construct
SEQUENCE: 7
VGTGGIVGSK GD                                                               12

SEQ ID NO: 8                moltype = AA  length = 13
FEATURE                     Location/Qualifiers
REGION                      1..13
                            note = Synthetic
REGION                      1..13
                            note = misc_feature - CDR-L3 of anti-CD137 clone 15
source                      1..13
                            mol_type = protein
                            organism = synthetic construct
SEQUENCE: 8
GADHGSGSNL FWV                                                              13

SEQ ID NO: 9                moltype = AA  length = 117
FEATURE                     Location/Qualifiers
REGION                      1..117
                            note = Synthetic
REGION                      1..117
                            note = misc_feature - Anti-CD137 clone 31 heavy chain
source                      1..117
                            mol_type = protein
                            organism = synthetic construct
SEQUENCE: 9
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCARDL RGAFDPWGQG TTVTVSS      117

SEQ ID NO: 10               moltype = AA  length = 217
FEATURE                     Location/Qualifiers
REGION                      1..217
                            note = Synthetic
REGION                      1..217
                            note = misc_feature - Anti-CD137 clone 31 light chain
source                      1..217
                            mol_type = protein
                            organism = synthetic construct
SEQUENCE: 10
QSALTQPASV SGSPGQSITI SCTGTSSDVG AYNFVSWYQQ RPGKAPELMI YDVSDRPSGV    60
SNRFSGSKSG NTASLTISGL QTEDEADYYC SSYTSSITRY VFGTGTKVTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECS                            217

SEQ ID NO: 11               moltype = AA  length = 7
FEATURE                     Location/Qualifiers
REGION                      1..7
                            note = Synthetic
REGION                      1..7
                            note = misc_feature - CDR-H1 of anti-CD137 clone 31
source                      1..7
                            mol_type = protein
                            organism = synthetic construct
SEQUENCE: 11
GYTFTGY                                                                      7

SEQ ID NO: 12               moltype = AA  length = 6
FEATURE                     Location/Qualifiers
REGION                      1..6
                            note = Synthetic
REGION                      1..6
                            note = misc_feature - CDR-H2 of anti-CD137 clone 31
source                      1..6
                            mol_type = protein
                            organism = synthetic construct
SEQUENCE: 12
NPNSGG                                                                       6

SEQ ID NO: 13               moltype = AA  length = 8
FEATURE                     Location/Qualifiers
REGION                      1..8
```

```
                              note = Synthetic
REGION                        1..8
                              note = misc_feature - CDR-H3 of anti-CD137 clone 31
source                        1..8
                              mol_type = protein
                              organism = synthetic construct
SEQUENCE: 13
DLRGAFDP                                                                      8

SEQ ID NO: 14                 moltype = AA  length = 14
FEATURE                       Location/Qualifiers
REGION                        1..14
                              note = Synthetic
REGION                        1..14
                              note = misc_feature - CDR-L1 of anti-CD137 clone 31
source                        1..14
                              mol_type = protein
                              organism = synthetic construct
SEQUENCE: 14
TGTSSDVGAY NFVS                                                              14

SEQ ID NO: 15                 moltype = AA  length = 7
FEATURE                       Location/Qualifiers
REGION                        1..7
                              note = Synthetic
REGION                        1..7
                              note = misc_feature - CDR-L2 of anti-CD137 clone 31
source                        1..7
                              mol_type = protein
                              organism = synthetic construct
SEQUENCE: 15
DVSDRPS                                                                       7

SEQ ID NO: 16                 moltype = AA  length = 11
FEATURE                       Location/Qualifiers
REGION                        1..11
                              note = Synthetic
REGION                        1..11
                              note = misc_feature - CDR-L3 of anti-CD137 clone 31
source                        1..11
                              mol_type = protein
                              organism = synthetic construct
SEQUENCE: 16
SSYTSSITRY V                                                                 11

SEQ ID NO: 17                 moltype = AA  length = 126
FEATURE                       Location/Qualifiers
REGION                        1..126
                              note = Synthetic
REGION                        1..126
                              note = misc_feature - Anti-CD137 clone 54 heavy chain
source                        1..126
                              mol_type = protein
                              organism = synthetic construct
SEQUENCE: 17
QVQLVQSGAE VKKPGSTVKV SCKASGGTFS SYAISWVRQA PGQGLEWMGR IIPILGIANY      60
AQKFQGRVTI TADKSTSTAY MELSSLRSED TAVYYCASPP YYDSSGYYPL GAFDIWGQGT     120
MVTVSS                                                               126

SEQ ID NO: 18                 moltype = AA  length = 213
FEATURE                       Location/Qualifiers
REGION                        1..213
                              note = Synthetic
REGION                        1..213
                              note = misc_feature - Anti-CD137 clone 54 light chain
source                        1..213
                              mol_type = protein
                              organism = synthetic construct
SEQUENCE: 18
SYELTQPPSV SVSPGQTASI TCSGDKLGEK YASWYQQKAG QSPILVIYQD SKRPSGIPER      60
FSGSNSGNTA TLTISGLQAG DEADYYCQAW DGSSTYVFGT GTKVTVFGQP KANPTVTLFP     120
PSSEELQANK ATLVCLISDF YPGAVTVAWK ADGSPVKAGV ETTKPSKQSN NKYAASSYLS     180
LTPEQWKSHR SYSCQVTHEG STVEKTVAPT ECS                                 213

SEQ ID NO: 19                 moltype = AA  length = 7
FEATURE                       Location/Qualifiers
REGION                        1..7
                              note = Synthetic
REGION                        1..7
```

```
                    note = misc_feature - CDR-H1 of anti-CD137 clone 54
source              1..7
                    mol_type = protein
                    organism = synthetic construct
SEQUENCE: 19
GGTFSSY                                                                   7

SEQ ID NO: 20       moltype = AA  length = 6
FEATURE             Location/Qualifiers
REGION              1..6
                    note = Synthetic
REGION              1..6
                    note = misc_feature - CDR-H2 of anti-CD137 clone 54
source              1..6
                    mol_type = protein
                    organism = synthetic construct
SEQUENCE: 20
IPILGI                                                                    6

SEQ ID NO: 21       moltype = AA  length = 17
FEATURE             Location/Qualifiers
REGION              1..17
                    note = Synthetic
REGION              1..17
                    note = misc_feature - CDR-H3 of anti-CD137 clone 54
source              1..17
                    mol_type = protein
                    organism = synthetic construct
SEQUENCE: 21
PPYYDSSGYY PLGAFDI                                                       17

SEQ ID NO: 22       moltype = AA  length = 11
FEATURE             Location/Qualifiers
REGION              1..11
                    note = Synthetic
REGION              1..11
                    note = misc_feature - CDR-L1 of anti-CD137 clone 54
source              1..11
                    mol_type = protein
                    organism = synthetic construct
SEQUENCE: 22
SGDKLGEKYA S                                                             11

SEQ ID NO: 23       moltype = AA  length = 7
FEATURE             Location/Qualifiers
REGION              1..7
                    note = Synthetic
REGION              1..7
                    note = misc_feature - CDR-L2 of anti-CD137 clone 54
source              1..7
                    mol_type = protein
                    organism = synthetic construct
SEQUENCE: 23
QDSKRPS                                                                   7

SEQ ID NO: 24       moltype = AA  length = 10
FEATURE             Location/Qualifiers
REGION              1..10
                    note = Synthetic
REGION              1..10
                    note = misc_feature - CDR-L3 of anti-CD137 clone 54
source              1..10
                    mol_type = protein
                    organism = synthetic construct
SEQUENCE: 24
QAWDGSSTYV                                                               10

SEQ ID NO: 25       moltype = AA  length = 327
FEATURE             Location/Qualifiers
REGION              1..327
                    note = Synthetic
REGION              1..327
                    note = misc_feature - constant domain in heavy chain (IgG4)
source              1..327
                    mol_type = protein
                    organism = synthetic construct
SEQUENCE: 25
ASTKGPSVFP LAPCSRSTSE STAALGCLVK DYFPEPVTVS WNSGALTSGV HTFPAVLQSS         60
GLYSLSSVVT VPSSSLGTKT YTCNVDHKPS NTKVDKRVES KYGPPCPPCP APEFLGGPSV        120
```

```
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 26           moltype = AA  length = 329
FEATURE                 Location/Qualifiers
REGION                  1..329
                        note = Synthetic
REGION                  1..329
                        note = misc_feature - constant domain in heavy chain
                          (engineered IgG1)
source                  1..329
                        mol_type = protein
                        organism = synthetic construct
SEQUENCE: 26
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCAVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 27           moltype = AA  length = 20
FEATURE                 Location/Qualifiers
REGION                  1..20
                        note = Synthetic
REGION                  1..20
                        note = misc_feature - SP1
source                  1..20
                        mol_type = protein
                        organism = synthetic construct
SEQUENCE: 27
METDTLLLWV LLLWVPGSTG                                               20

SEQ ID NO: 28           moltype = AA  length = 5
FEATURE                 Location/Qualifiers
REGION                  1..5
                        note = Synthetic
REGION                  1..5
                        note = misc_feature - GS linker
source                  1..5
                        mol_type = protein
                        organism = synthetic construct
SEQUENCE: 28
GGGGS                                                                5

SEQ ID NO: 29           moltype = AA  length = 10
FEATURE                 Location/Qualifiers
REGION                  1..10
                        note = Synthetic
REGION                  1..10
                        note = misc_feature - (G4S)2 linker
source                  1..10
                        mol_type = protein
                        organism = synthetic construct
SEQUENCE: 29
GGGGSGGGGS                                                          10

SEQ ID NO: 30           moltype = AA  length = 217
FEATURE                 Location/Qualifiers
REGION                  1..217
                        note = Synthetic
REGION                  1..217
                        note = misc_feature - Anti-PD-L1#6 Light Chain
source                  1..217
                        mol_type = protein
                        organism = synthetic construct
SEQUENCE: 30
QSVLTQPPSA SGTPGQRVTI SCSGSSSNIG SNTVNWYQQL PGTAPKLLIY SNNQRPSGVP    60
DRFSGSKSGT SASLAISGLQ SEDEADYYCA TWDSLNAWV VFGGGTKLTV LGQPKAAPSV    120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 31           moltype = AA  length = 700
FEATURE                 Location/Qualifiers
REGION                  1..700
                        note = Synthetic
REGION                  1..700
```

```
                          note = misc_feature - Anti-PD-L1 #6-CD137 #31 bsAb Heavy
                              Chain
source                    1..700
                          mol_type = protein
                          organism = synthetic construct
SEQUENCE: 31
QVQLVQSGAE VKKPGSSVKV SCKASGGTFR RYSISWVRQA PGQGLEWMGG IIPVFGAAKY      60
AQKFQGRVTI TADEFTSTAY MELSSLTSED TAVYYCALSG DSDAFDIWGQ GTMVTVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSNT KVDKKVEPKS CDKTHTCPPC PAPELLGGPS     240
VFLFPPKPKD TLMISRTPEV TCVVVDVSHE DPEVKFNWYV DGVEVHNAKT KPREEQYAST     300
YRVVSVLTVL HQDWLNGKEY KCAVSNKALP APIEKTISKA KGQPREPQVY TLPPSREEMT     360
KNQVSLTCLV KGFYPSDIAV EWESNGQPEN NYKTTPPVLD SDGSFFLYSK LTVDKSRWQQ     420
GNVFSCSVMH EALHNHYTQK SLSLSPGGGG GSGGGGQSAL TQPASVSGSP GQSITISCTG     480
TSSDVGAYNF VSWYQQRPGK APELMIYDVS DRPSGVSNRF SGSKSGNTAS LTISGLQTED     540
EADYYCSSYT SSITRYVFGT GTKVTVLGGG GSGGGGSGGG GSQVQLVQSG AEVKKPGASV     600
KVSCKASGYT FTGYYMHWVR QAPGQGLEWM GWINPNSGGT NYAQKFQGRV TMTRDTSIST     660
AYMELSRLRS DDTAVYYCAR DLRGAFDPWG QGTTVTVSSA                           700

SEQ ID NO: 32             moltype = AA  length = 712
FEATURE                   Location/Qualifiers
REGION                    1..712
                          note = Synthetic
REGION                    1..712
                          note = misc_feature - Anti-PD-L1#6-CD137 #54 bsAb Heavy
                              Chain
source                    1..712
                          mol_type = protein
                          organism = synthetic construct
SEQUENCE: 32
QVQLVQSGAE VKKPGSSVKV SCKASGGTFR RYSISWVRQA PGQGLEWMGG IIPVFGAAKY      60
AQKFQGRVTI TADEFTSTAY MELSSLTSED TAVYYCALSG DSDAFDIWGQ GTMVTVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSNT KVDKKVEPKS CDKTHTCPPC PAPELLGGPS     240
VFLFPPKPKD TLMISRTPEV TCVVVDVSHE DPEVKFNWYV DGVEVHNAKT KPREEQYAST     300
YRVVSVLTVL HQDWLNGKEY KCAVSNKALP APIEKTISKA KGQPREPQVY TLPPSREEMT     360
KNQVSLTCLV KGFYPSDIAV EWESNGQPEN NYKTTPPVLD SDGSFFLYSK LTVDKSRWQQ     420
GNVFSCSVMH EALHNHYTQK SLSLSPGGGG GSGGGGSQVQ LVQSGAEVKK PGSTVKVSCK     480
ASGGTFSSYA ISWVRQAPGQ GLEWMGRIIP ILGIANYAQK FQGRVTITAD KSTSTAYMEL     540
SSLRSEDTAV YYCASPPYYD SSGYYPLGAF DIWGQGTMVT VSSAGGGGSG GGGSGGGGSG     600
GGGSSYELTQ PPSVSVSPGQ TASITCSGDK LGEKYASWYQ QKAGQSPILV IYQDSKRPSG     660
IPERFSGSNS GNTATLTISG LQAGDEADYY CQAWDGSSTY VFGTGTKVTV LG            712

SEQ ID NO: 33             moltype = AA  length = 244
FEATURE                   Location/Qualifiers
REGION                    1..244
                          note = Synthetic
REGION                    1..244
                          note = misc_feature - CD137#31-scFv
source                    1..244
                          mol_type = protein
                          organism = synthetic construct
SEQUENCE: 33
QSALTQPASV SGSPGQSITI SCTGTSSDVG AYNFVSWYQQ RPGKAPELMI YDVSDRPSGV      60
SNRFSGSKSG NTASLTISGL QTEDEADYYC SSYTSSITRY VFGTGTKVTV LGGGGSGGGG     120
SGGGGSQVQL VQSGAEVKKP GASVKVSCKA SGYTFTGYYM HWVRQAPGQG LEWMGWINPN     180
SGGTNYAQKF QGRVTMTRDT SISTAYMELS RLRSDDTAVY YCARDLRGAF DPWGQGTTVT     240
VSSA                                                                  244

SEQ ID NO: 34             moltype = AA  length = 255
FEATURE                   Location/Qualifiers
REGION                    1..255
                          note = Synthetic
REGION                    1..255
                          note = misc_feature - CD137#54-scFv
source                    1..255
                          mol_type = protein
                          organism = synthetic construct
SEQUENCE: 34
QVQLVQSGAE VKKPGSTVKV SCKASGGTFS SYAISWVRQA PGQGLEWMGR IIPILGIANY      60
AQKFQGRVTI TADKSTSTAY MELSSLRSED TAVYYCASPP YYDSSGYYPL GAFDIWGQGT     120
MVTVSSAGGG GSGGGGSGGG GSGGGGSSYE LTQPPSVSVS PGQTASITCS GDKLGEKYAS     180
WYQQKAGQSP ILVIYQDSKR PSGIPERFSG SNSGNTATLT ISGLQAGDEA DYYCQAWDGS     240
STYVFGTGTK VTVLG                                                     255

SEQ ID NO: 35             moltype = AA  length = 214
FEATURE                   Location/Qualifiers
REGION                    1..214
                          note = Synthetic
```

```
REGION                      1..214
                            note = misc_feature - Trastuzumab Light Chain
source                      1..214
                            mol_type = protein
                            organism = synthetic construct
SEQUENCE: 35
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 36               moltype = AA  length = 714
FEATURE                     Location/Qualifiers
REGION                      1..714
                            note = Synthetic
REGION                      1..714
                            note = misc_feature - Trastuzumab-CD137 #54 bsAb Heavy Chain
source                      1..714
                            mol_type = protein
                            organism = synthetic construct
SEQUENCE: 36
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYA   300
STYRVVSVLT VLHQDWLNGK EYKCAVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGG GGGSGGGGSQ VQLVQSGAEV KKPGSTVKVS   480
CKASGGTFSS YAISWVRQAP GQGLEWMGRI IPILGIANYA QKFQGRVTIT ADKSTSTAYM   540
ELSSLRSEDT AVYYCASPPY YDSSGYYPLG AFDIWGQGTM VTVSSAGGGG SGGGGSGGGG   600
SGGGGSSYEL TQPPSVSVSP GQTASITCSG DKLGEKYASW YQQKAGQSPI LVIYQDSKRP   660
SGIPERFSGS NSGNTATLTI SGLQAGDEAD YYCQAWDGSS TYVFGTGTKV TVLG         714

SEQ ID NO: 37               moltype = AA  length = 216
FEATURE                     Location/Qualifiers
REGION                      1..216
                            note = Synthetic
REGION                      1..216
                            note = misc_feature - Anti-Her2 #3-7 Light Chain
source                      1..216
                            mol_type = protein
                            organism = synthetic construct
SEQUENCE: 37
QTVVTQEPSF SVSPGGTVTL TCGLSSGSVS TSYYPSWYQQ TPGQAPRTLI YSTNTRSSGV    60
PDRFSGSILG NKAALTITGA QADDESDYYC VLYMGSGIWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 38               moltype = AA  length = 717
FEATURE                     Location/Qualifiers
REGION                      1..717
                            note = Synthetic
REGION                      1..717
                            note = misc_feature - Anti-Her2 #3-7-CD137 #54 bsAb Heavy
                             Chain
source                      1..717
                            mol_type = protein
                            organism = synthetic construct
SEQUENCE: 38
EVQLVQSGAE VKKPGESLKI SCKGSGYSFT SYWIGWVRQM PGKGLEWMGI IYPGDSDTRY    60
SPSFQGQVTI SADKSISTAY LQWSSLKASD TAMYYCARQD NWNHGPYDAF DIWGQGTMVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYASTYRVVS VLTVLHQDWL NGKEYKCAVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGGSGGGG GSQVQLVQSG AEVKKPGSTV   480
KVSCKASGGT FSSYAISWVR QAPGQGLEWM GRIIPILGIA NYAQKFQGRV TITADKSTST   540
AYMELSSLRS EDTAVYYCAS PPYYDSSGYY PLGAFDIWGQ GTMVTVSSAG GGGSGGGGSG   600
GGGSGGGGSS YELTQPPSVS VSPGQTASIT CSGDKLGEKY ASWYQQKAGQ SPILVIYQDS   660
KRPSGIPERF SGSNSGNTAT LTISGLQAGD EADYYCQAWD GSSTYVFGTG TKVTVLG      717

SEQ ID NO: 39               moltype = AA  length = 213
FEATURE                     Location/Qualifiers
REGION                      1..213
                            note = Synthetic
REGION                      1..213
                            note = misc_feature - Anti-Glycan Light Chain
```

```
source                    1..213
                          mol_type = protein
                          organism = synthetic construct
SEQUENCE: 39
EIVLTQSPST LSLSPGERAT LSCQASEDVS YMHWYQQKPG QAPQPWIYGT SNKASGVPSR    60
FSGSGSGTDF TLTISSLQPE DVATYYCQQW SRRPFTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 40             moltype = AA  length = 717
FEATURE                   Location/Qualifiers
REGION                    1..717
                          note = Synthetic
REGION                    1..717
                          note = misc_feature - Anti-Glycan-CD137 #54 bsAb Heavy Chain
source                    1..717
                          mol_type = protein
                          organism = synthetic construct
SEQUENCE: 40
QITLQESGPT LVKPTQTLTL TCTFSGFSLY RFDMGVGWIR QPPGQGLEWL AHIWWDDDKY    60
YNPALKSRLT ISKDTSKNQV VLTMTNMDPV DTATYYCARV RGLHDYYYF AYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYASTYRVVS VLTVLHQDWL NGKEYKCAVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGGGSGGG GSQVQLVQSG AEVKKPGSTV   480
KVSCKASGGT FSSYAISWVR QAPGQGLEWM GRIIPILGIA NYAQKFQGRV TITADKSTST   540
AYMELSSLRS EDTAVYYCAS PPYYDSSGYY PLGAFDIWGQ GTMVTVSSAG GGGSGGGGSG   600
GGGSGGGGSS YELTQPPSVS VSPGQTASIT CSGDKLGEKY ASWYQQKAGQ SPILVIYQDS   660
KRPSGIPERF SGSNSGNTAT LTISGLQAGD EADYYCQAWD GSSTYVFGTG TKVTVLG      717

SEQ ID NO: 41             moltype = AA  length = 7
FEATURE                   Location/Qualifiers
REGION                    1..7
                          note = Synthetic
REGION                    1..7
                          note = misc_feature - CDR-H1 of anti-Her2#3-7
source                    1..7
                          mol_type = protein
                          organism = synthetic construct
SEQUENCE: 41
GYSFTSY                                                              7

SEQ ID NO: 42             moltype = AA  length = 6
FEATURE                   Location/Qualifiers
REGION                    1..6
                          note = Synthetic
REGION                    1..6
                          note = misc_feature - CDR-H2 of anti-Her2#3-7
source                    1..6
                          mol_type = protein
                          organism = synthetic construct
SEQUENCE: 42
YPGDSD                                                               6

SEQ ID NO: 43             moltype = AA  length = 14
FEATURE                   Location/Qualifiers
REGION                    1..14
                          note = Synthetic
REGION                    1..14
                          note = misc_feature - CDR-H3 of anti-Her2#3-7
source                    1..14
                          mol_type = protein
                          organism = synthetic construct
SEQUENCE: 43
QDNWNHGPYD AFDI                                                     14

SEQ ID NO: 44             moltype = AA  length = 14
FEATURE                   Location/Qualifiers
REGION                    1..14
                          note = Synthetic
REGION                    1..14
                          note = misc_feature - CDR-L1 of anti-Her2#3-7
source                    1..14
                          mol_type = protein
                          organism = synthetic construct
SEQUENCE: 44
GLSSGSVSTS YYPS                                                     14
```

```
SEQ ID NO: 45          moltype = AA  length = 7
FEATURE                Location/Qualifiers
REGION                 1..7
                       note = Synthetic
REGION                 1..7
                       note = misc_feature - CDR-L2 of anti-Her2#3-7
source                 1..7
                       mol_type = protein
                       organism = synthetic construct
SEQUENCE: 45
STNTRSS                                                                    7

SEQ ID NO: 46          moltype = AA  length = 10
FEATURE                Location/Qualifiers
REGION                 1..10
                       note = Synthetic
REGION                 1..10
                       note = misc_feature - CDR-L3 of anti-Her2#3-7
source                 1..10
                       mol_type = protein
                       organism = synthetic construct
SEQUENCE: 46
VLYMGSGIWV                                                                10
```

BISPECIFIC CD137-BINDING ANTIBODIES FOR T-CELL ACTIVATION

CROSS-REFERENCE TO RELATED APPLICATIONS

This application is a divisional application of U.S. application Ser. No. 16/911,052 filed Jun. 24, 2020; which claims the benefit under 35 USC § 119(e) to U.S. Application Ser. No. 62/953,302 filed Dec. 24, 2019 and to U.S. Application Ser. No. 62/866,699 filed Jun. 26, 2019. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing xml file, named AP1100-3_ST26.xml, was created on Jul. 13, 2023, and is 82,579 bytes in size.

BACKGROUND OF THE INVENTION

Field of the Invention

The present invention relates generally to antibodies and antigen binding fragments thereof and more specifically to antibodies and antigen binding fragments for enhancing T-cell function.

Background Information

Immunoregulation of the adaptive immune system has been an attractive field in cancer immunotherapy because of fewer side effects and long-term protection from cancer relapse. Two signals are generally required to fully activate T cells, an antigen-specific signal from the T-cell receptor (TCR), and a signal from a costimulatory molecule, such as CD28. In the past decade, additional co-stimulatory as well as co-inhibitory molecules were discovered on T cells that can positively or negatively modulate TCR signaling.

CD137 (4-1BB), a costimulatory molecule that belongs to the TNF receptor superfamily, was cloned from activated T cells in 1989 (Kwon & Weissman, 1989). The 4-1BB:4-1BBL pathway appears to amplify existing costimulatory signals, although engagement of 4-1BB in the presence of strong TCR signaling can induce IL-2 production in a CD28-independent manner. CD137 signaling has been demonstrated to boost TCR signaling, induce cytokine synthesis and T-cell proliferation, and inhibit activation-induced apoptosis. CD137 stimulation on T cells induces the NF-κB and PI3K/ERK signaling pathways responsible for preventing T-cell activation-induced apoptosis and inducing T-cell proliferation, respectively. Both CD4 and CD8 T cells respond to CD137 stimulation that results in enhanced expansion and effector function, while CD8 T cells preferentially respond to CD137 signaling by inducing greater cytokine production. In addition to expression on activated T cells, CD137 is expressed on multiple lineages of hematopoietic cells, including regulatory T cells, B cells, natural killer cells (NKs), monocytes, and dendritic cells (DCs). In DCs, stimulation of CD137 increases the secretion of IL-6 and IL-12, and more importantly it enhances the ability of DCs to stimulate T cell proliferation in response to alloantigens and nominal antigens. In NKs, CD137 stimulation promotes proliferation and IFN-γ production, but not cytolytic activity. Nevertheless, CD137-stimulated NK cells show a helper role in promoting the expansion of activated T cells.

In the clinic, the anti-CD137 agonist antibody Urelumab (BMS-663513) showed partial remission and some stabilization of disease. However, fatal hepatotoxicity resulted in termination of most trials. Trials of another anti-CD137 antibody, Utomilumab (PF-05082566), achieved an objective response rate of 3.8% in patients with solid tumors and 13.3% in patients with Merkel cell carcinoma, including complete and partial responses, without causing hepatotoxicity. Urelumab and Utomilumab show distinct properties. For agonist activity, Urelumab is strong and crosslinking-independent, whereas Utomilumab is weak and crosslinking-dependent. Crystal structures of Urelumab and Utomilumab with CD137 reveal distinct binding epitopes that affect the CD137-CD137L interaction. Distinct epitope recognition and CD137-CD137L binding blockade may result in the distinct potency and toxicity of these two anti-CD137 antibodies. However, ligand engagement does not determine CD137-mediated toxicity since the anti-4-1BB monoclonal antibodies (mAbs) 3H3 and 2A have opposing effects on CD137L binding, but show similar hepatotoxicity profiles. Recently, the engineered Fc region of a weak agonistic antibody has been shown to preferentially bind to FcγRIIB (at a low A/I FcγR-binding ratio), resulting in potent agonistic activity comparable to Urelumab without inducing hepatotoxicity. Agonistic anti-CD137 antibodies have been shown to have anticancer activities through potentiating T-cell cytotoxicity in a CD40-dependent manner. Moreover, antigen expression is required for anti-CD137 antibodies to regress established poorly antigenic tumors. Furthermore, the combination of anti-PD-1 and anti-CD137 antibodies showed enhanced antitumor activity in mouse tumor models through enhancing T-cell effector function and tumor infiltration compared to mono-treatment with each antibody. In addition to anti-cancer treatment, anti-CD137 agonist antibodies have also been shown to ameliorate experimental autoimmune encephalomyelitis and enhance antiviral immunity, depending on the timing of treatment.

PD-1 was first isolated from T cells undergoing apoptosis. Its ligand PD-L1 was later identified, and interaction between PD-1 and PD-L1 has been demonstrated to block T cell activation. PD-1 is not expressed on resting T cells, but is induced upon activation. Sustained expression of PD-1 is found on exhausted T cells in chronic infections and cancer. Under normal conditions, the PD-1/PD-L1 pathway is important for maintaining peripheral tolerance to prevent autoimmunity. However, the self-protective function of PD-L1 is hijacked in cancer, with PD-L1 expressed by various cancer cell types to evade immune system surveillance. Antibodies targeting PD-1/PD-L1 block inhibitory signaling and restore anti-cancer activities of T cells. The PD-1/PD-L1 pathway has been regarded as a dominant-negative regulator of effector function of anti-tumor T cells. In the clinic, blockade of this pathway has achieved a high objective response rate ranging from 35% to 87% in some cancer types, such as Hodgkin's lymphoma, Merkel cell carcinoma, and melanoma. Other cancer types, such as NSCLC, head and neck cancer, and renal cell carcinoma, achieved lower objective response rates in the range of 15% to 25%.

The combination of anti-PD-1 and anti-CD137 antibodies showed enhanced anti-tumor activity in mouse tumor models through enhancing T-cell effector function and tumor infiltration compared to mono-treatment with each antibody. In the clinic, the combination of Utomilumab (0.45-5.0 mg/kg) and Pembrolizumab showed a synergistic anti-tumor effect in patients with advanced solid tumors with no dose-limiting toxicity.

Based on the immune modulating roles of CD137, anti-human 4-1BB agonist antibodies could be used for the treatment of cancer and autoimmune and infectious diseases. However, the use of anti-human-4-1BB agonist antibodies is limited due to liver toxicity. Moreover, no effective treatments have been described that combine activation of the 4-1BB:4-1BBL pathway in the absence of liver toxicity with blocking immune inhibitory or tumor signaling pathways. Thus, there exists a need for effective engagement of the 4-1BB:4-1BBL pathway in combination with relieving inhibition of immune activation or in combination with inhibiting tumor cell signaling.

SUMMARY OF THE INVENTION

The present invention is based on the seminal discovery that anti-CD137 antibodies can be generated that possess potent cross-linking dependent agonist activity and that might circumvent liver toxicity seen in clinical trials. The present invention is further based on the discovery that bispecific antibodies targeting PD-L1 and CD137 possess extraordinary activity to boost T-cell effector function and inhibit tumor growth in vivo better than mono-treatment or combination treatment with each antibody. Bispecific antibodies may have a unique anti-CD137 single chain variable fragment (scFv) that activates T cells upon crosslinking via the other arm of the bispecific antibody that binds to PD-L1, for example. The bispecific antibody may also be targeted to non-PD-L1-expressing tumors by changing the anti-PD-L1 arm to other tumor-specific binders, such as anti-Her2 or an anti-tumor-specific glycan, as provided herein. A bispecific antibody that induces target-dependent T-cell activation may avoid hepatotoxicity while maintaining the anti-tumor potency of anti-CD137 monoclonal antibodies.

In some embodiments, the present invention provides three agonist antibodies or antigen binding fragments thereof: anti-CD137 antibody clone 15 (CD137 #15), anti-CD137 antibody clone 31 (CD137 #31), and anti-CD137 antibody clone 54 (CD137 #54). In one aspect, anti-CD137 antibodies provided herein include a heavy chain variable ($V_H$) region including an amino acid sequence with at least 80% sequence identity to a sequence selected from SEQ ID NO:1, SEQ ID NO:9, or SEQ ID NO:17; and a light chain variable ($V_L$) region including an amino acid sequence with at least 80% sequence identity to a sequence selected from SEQ ID NO:2, SEQ ID NO:10, or SEQ ID NO:18. In another aspect, the antibody or antigen binding fragment having a $V_H$ region that includes an amino acid sequence having at least 80% identity to SEQ ID NO:1 and a $V_L$ region that includes an amino acid sequence having at least 80% identity to SEQ ID NO:2 includes (a) $V_H$ CDR-H1, CDR-H2, and CDR-H3, wherein CDR-H1 includes an amino acid sequence having at least 80% identity to SEQ ID NO:3, wherein CDR-H2 includes an amino acid sequence having at least 80% identity to SEQ ID NO:4, and wherein CDR-H3 includes an amino acid sequence having at least 80% identity to SEQ ID NO:5; and (b) $V_L$ CDR-L1, CDR-L2, and CDR-L3, wherein CDR-L1 includes an amino acid sequence having at least 80% identity to SEQ ID NO:6, wherein CDR-L2 includes an amino acid sequence having at least 80% identity to SEQ ID NO:7, and wherein CDR-L3 includes an amino acid sequence having at least 80% identity to SEQ ID NO:8.

In another aspect, the antibody or antigen binding fragment thereof having a $V_H$ region that includes an amino acid sequence having at least 80% identity to SEQ ID NO:9 and a $V_L$ region that includes an amino acid sequence having at least 80% identity to SEQ ID NO:10 includes (a) $V_H$ CDR-H1, CDR-H2, and CDR-H3, wherein CDR-H1 includes an amino acid sequence having at least 80% identity to SEQ ID NO: 11, wherein CDR-H2 includes an amino acid sequence having at least 80% identity to SEQ ID NO:12, and wherein CDR-H3 includes an amino acid sequence having at least 80% identity to SEQ ID NO:13; and (b) $V_L$ CDR-L1, CDR-L2, and CDR-L3, wherein CDR-L1 includes an amino acid sequence having at least 80% identity to SEQ ID NO:14, wherein CDR-L2 includes an amino acid sequence having at least 80% identity to SEQ ID NO: 15, and wherein CDR-L3 includes an amino acid sequence having at least 80% identity to SEQ ID NO: 16.

In yet another aspect, the antibody or antigen binding fragment thereof having a $V_H$ region that includes an amino acid sequence having at least 80% identity to SEQ ID NO:17 and a $V_L$ region that includes an amino acid sequence having at least 80% identity to SEQ ID NO:18 includes (a) $V_H$ CDR-H1, CDR-H2, and CDR-H3, wherein CDR-H1 includes an amino acid sequence having at least 80% identity to SEQ ID NO:19, wherein CDR-H2 includes an amino acid sequence having at least 80% identity to SEQ ID NO:20, and wherein CDR-H3 includes an amino acid sequence having at least 80% identity to SEQ ID NO:21; and (b) $V_L$ CDR-L1, CDR-L2, and CDR-L3, wherein CDR-L1 includes an amino acid sequence having at least 80% identity to SEQ ID NO:22, wherein CDR-L2 includes an amino acid sequence having at least 80% identity to SEQ ID NO:23, and wherein CDR-L3 includes an amino acid sequence having at least 80% identity to SEQ ID NO:24.

In one aspect, antibodies or antigen binding fragments thereof provided herein include an Fc domain. In another aspect, the Fc domain is an IgG, IgE, IgM, IgD, IgA, or IgY domain. In yet another aspect, the IgG domain is an IgG1, IgG2, IgG3, or IgG4 domain. In an additional aspect, the IgG1 domain includes an amino acid sequence of SEQ ID NO:26. In certain aspects, IgG1 includes point mutations compared to wild-type IgG1 that modify or reduce antibody-dependent cellular cytotoxicity (ADCC) and/or complement-dependent cytotoxicity (CDC). Exemplary point mutations include K297A and K322A mutations. In yet another aspect, the IgG4 domain includes an amino acid sequence of SEQ ID NO:25. In a further aspect, antigen fragments provided herein include an scFv, an F(ab)2, or an Fab.

In an embodiment, the present disclosure also provides a pharmaceutical composition that includes any one of the antibodies or an antigen binding fragment thereof provided herein. In one aspect, antibodies or antigen binding fragments of pharmaceutical compositions provided herein include a pharmaceutically acceptable carrier conjugated to the C-terminus of one or more polypeptides of the antibody or antigen binding fragment thereof. In another aspect, pharmaceutical compositions provided herein include a bispecific antibody.

In one embodiment, the present disclosure also provides a method of treating cancer that includes administering to a subject in need thereof an effective amount of an antibody or antigen binding fragment thereof provided herein, or an effective amount of a bispecific antibody provided herein. In one aspect, the cancer is selected from prostate cancer, lung cancer, Non-Small Cell Lung Cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

In one embodiment, provided herein are bispecific antibodies that include a first antigen binding region and a second antigen binding region, wherein the first antigen binding region binds to CD137. In one aspect, bispecific antibodies provided herein include (i) a $V_H$ region including an amino acid sequence having at least 80% identity to a sequence selected from SEQ ID NO:1; SEQ ID NO:9; and SEQ ID NO:17; and (ii) a $V_L$ region including an amino acid sequence having at least 80% identity to an N-terminal sequence of about 100 to 120 amino acids of a sequence selected from SEQ ID NO:2; SEQ ID NO:10; and SEQ ID NO:18, wherein the second antigen binding region binds to an immune checkpoint molecule, an immune stimulatory molecule, or a tumor antigen.

In one aspect, bispecific antibodies provided herein include a heavy chain sequence of SEQ ID NO:31 or SEQ ID NO:32. In another aspect, bispecific antibodies provided herein further include a light chain sequence of SEQ ID NO:30. In one aspect, bispecific antibodies provided herein include a heavy chain sequence of SEQ ID NO:36. In another aspect, bispecific antibodies provided herein further include a light chain sequence of SEQ ID NO:35. In one aspect, bispecific antibodies provided herein include a heavy chain sequence of SEQ ID NO:38. In another aspect, bispecific antibodies provided herein further include a light chain sequence of SEQ ID NO:37. In one aspect, bispecific antibodies provided herein include a heavy chain sequence of SEQ ID NO:40. In another aspect, bispecific antibodies provided herein further include a light chain sequence of SEQ ID NO:39.

In one aspect, bispecific antibodies provided herein include a first antigen binding region having (a) a $V_H$ region including an amino acid sequence of SEQ ID NO:9 and a $V_L$ region including an amino acid sequence of about 100 to 120 amino acids of an N-terminal sequence of SEQ ID NO:10; or (b) a $V_H$ region including an amino acid sequence of SEQ ID NO:17 and a $V_L$ region including an amino acid sequence of about 100 to 120 amino acids of an N-terminal sequence of SEQ ID NO:18. In another aspect, the second antigen binding region binds to an antigen selected from PD-L1, PD-1, CTLA-4, LAG3, CD28, CD40, CD137, CD27, ICOS, Her2, or a glycan. In yet another aspect, the second antigen binding region binds to PD-L1, Her2, or a glycan.

In one aspect, the present invention discloses that anti-PD-L1 #6-CD137 #54 bispecific antibody (bsAb) could act as a platform to exert target-dependent T cell activation through the crosslinking-dependent agonist activity of an anti-CD137 #54 single chain.

In another aspect, bispecific antibodies that bind to CD137 and PD-L1 are modified to bind to CD137 and other targets expressed on tumors, including immune regulatory molecules and tumor-specific markers, such as Her2 or a tumor-specific glycan.

In one aspect, the first antigen binding region and the second antigen binding region of bispecific antibodies provided herein include an Fc domain, an Fab fragment, a single chain variable fragment (scFv), or any combination thereof. In yet another aspect, the scFv includes (i) a $V_H$ region that includes an amino acid sequence of SEQ ID NO:9 and a $V_L$ region that includes an amino acid sequence of about 100 to 120 amino acids of an N-terminal sequence of SEQ ID NO:10; or (ii) a $V_H$ region that includes an amino acid sequence of SEQ ID NO:17 and a $V_L$ region that includes an amino acid sequence of about 100 to 120 amino acids of an N-terminal sequence of SEQ ID NO:18. In a further aspect, bispecific antibodies provided herein include a linker between the $V_H$ region and the $V_L$ region of the scFv. In an additional aspect, the scFv includes an amino acid sequence SEQ ID NO:33 or SEQ ID NO:34.

In one aspect, bispecific antibodies provided herein include an Fc domain. In another aspect, the Fc domain is an IgG domain, an IgE domain, an IgM domain, and IgD domain, an IgA domain, or an IgY domain. In yet another aspect, the Fc domain is an IgG domain. In a further aspect, the IgG domain is an IgG1 domain, an IgG2 domain, an IgG3 domain, or an IgG4 domain.

In one aspect, the scFv is linked to the C-terminus of the Fc domain. In another aspect, bispecific antibodies provided herein include a linker between the Fab domain and the scFv domain. In a further aspect, the Fab fragment is linked to the N-terminus of the Fc domain. In yet a further aspect, the Fab includes a PD-L1 binding site, a Her2 binding site, or a glycan binding site and the scFv includes a CD137 binding site.

In one embodiment, the invention provides an antibody-drug conjugate that includes a therapeutic agent and an antibody, including any bispecific antibody, provided herein or an antigen binding fragment thereof. In one aspect, the therapeutic agent is covalently linked to the antibody or the antigen binding fragment via a linker.

In one embodiment, provided herein are pharmaceutical compositions that include any bispecific antibody provided herein and at least one pharmaceutically acceptable carrier.

In one embodiment, the invention provides an isolated amino acid sequence as set forth in SEQ ID NOs:1-26. In another embodiment, the invention provides an isolated amino acid sequence as set forth in SEQ ID NOs:30-40.

In one embodiment, the present disclosure also provides an isolated nucleic acid sequence encoding the antibody, an antigen-binding fragment thereof, or the bispecific antibody of the invention. In another embodiment, the invention provides an isolated nucleic acid encoding any one of SEQ ID NOs:1-26. In another embodiment, the invention provides an isolated nucleic acid sequence encoding any one of SEQ ID NOs:30-40.

BRIEF DESCRIPTION OF THE DRAWINGS

FIGS. 18A-18B show that the antigen-specific recall responses of memory CD4 (FIG. 18A) and memory CD8 (FIG. 18B) T cells are strikingly boosted by the anti-PD-L1 #6-CD137 #54 bsAb.

(FIG. 20A) NCI-H1975, non-small cell lung cancer cells; (FIG. 20B) PC-3, prostate cancer cells; (FIG. 20C) MDA-MB-231, breast cancer cells.

(FIG. 21A) SKBR-3, breast cancer cells; (FIG. 21B) MDA-MD-361, breast cancer cells.

(FIG. 22A) MCF-7, breast cancer cells; (FIG. 22B) NCI-N87, gastric cancer cells.

DETAILED DESCRIPTION OF THE INVENTION

Figure 1:
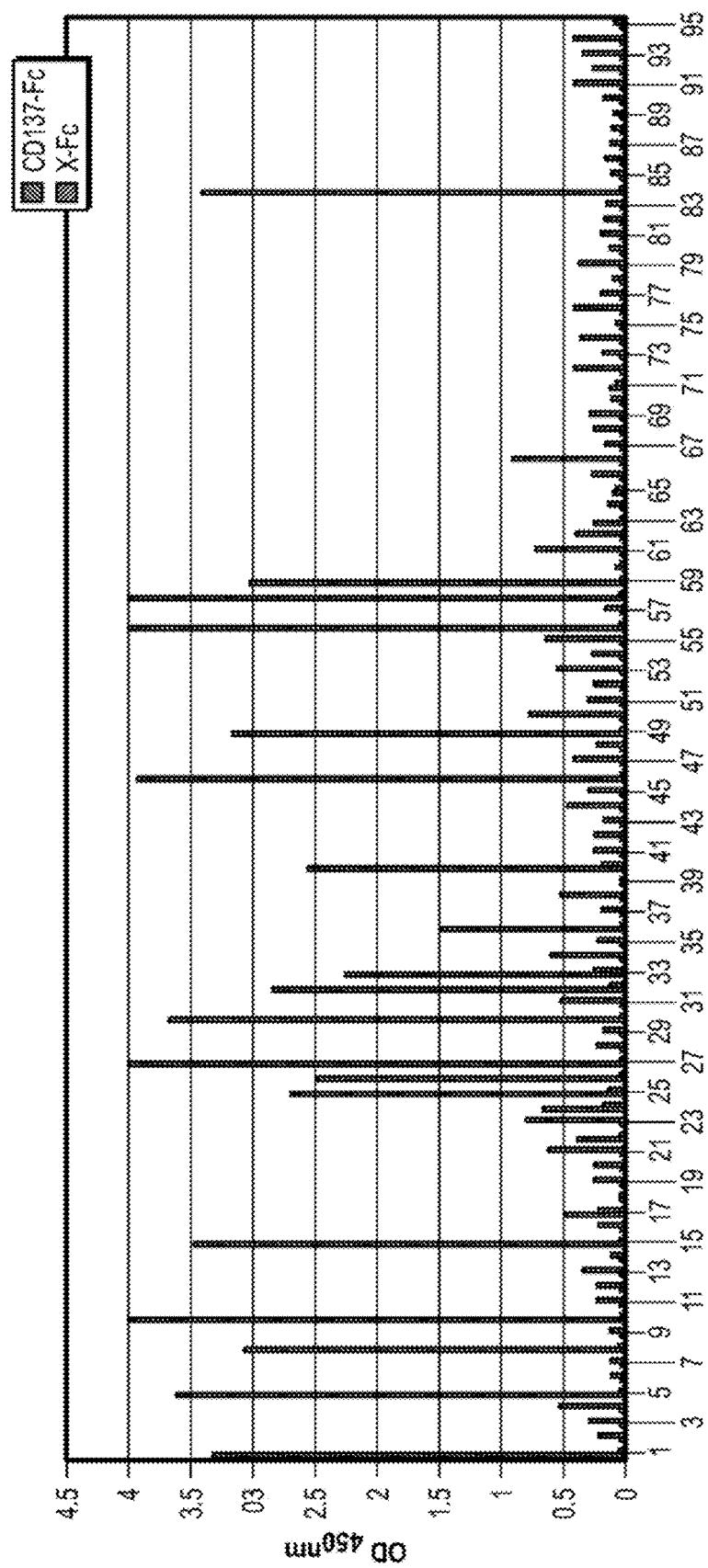
FIG. 1 shows the screening for phage clones targeted to CD137 by direct ELISA.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Provided herein, in some embodiments, are antibodies and antigen binding fragments thereof that bind CD137. Also provided herein are amino sequences of antibodies that bind CD137. As used herein, the term "antibody" refers to an immunoglobulin molecule that has the ability to specifically bind to an antigen. The term "antibody" includes, but is not limited to, monoclonal antibodies, polyclonal antibodies, human antibodies, humanized antibodies, chimeric antibodies, bispecific antibodies, and anti-idiotypic antibodies, unless context clearly indicates otherwise. In one aspect, antibodies provided herein include monoclonal antibodies. Antibodies provided herein include any isotype and class (e.g., IgG, IgE, IgM, IgD, IgA and IgY), or subclass (e.g., IgG1, IgG2, IgG3, IgG4, IgA1 and IgA2). As used herein, "antigen binding fragment" means a fragment or portion of an immunoglobulin molecule or antibody that has the ability to specifically bind to the same antigen as the immunoglobulin molecule or antibody. Exemplary antigen binding fragments include scFv, Fab, or F(ab)2 fragments. As used herein, "antigen binding region" means the part of an antibody or immunoglobulin molecule that binds to antigens or proteins by contacting the antigen or protein, for example. An antigen binding region generally includes heavy chain variable ($V_H$) regions and light chain variable ($V_L$) regions. An antigen binding region generally includes one or more antigen binding sites or paratopes.

Antibodies provided herein have a $V_H$ region including an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to a sequence of SEQ ID NO:1; SEQ ID NO:9; or SEQ ID NO:17. Antibodies provided herein also include an $V_L$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to a sequence of SEQ ID NO:2; SEQ ID NO: 10; or SEQ ID NO: 18.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence. As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad. Sci. USA* 87:2264-2268 (1990) and as discussed in Altschul, et al., *J. Mol. Biol.* 215:403-410 (1990); Karlin and Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at ebi.ac.uk/Tools/psa/emboss_needle/, optionally with default settings), the Smith-Waterman algorithm (see, e.g., the EMBOSS Water aligner available at ebi.ac.uk/Tools/psa/emboss_water/, optionally with default settings), the similarity search method of Pearson and Lipman, 1988, *Proc. Natl. Acad. Sci. USA* 85, 2444, or computer programs which use these algorithms (GAP, BESTFIT, FASTA, BLAST P, BLAST N and TFASTA in Wisconsin Genetics Software Package, Genetics Computer Group, 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

In one aspect, the antibody or antigen binding fragment thereof has a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:1 and a $V_L$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:2. SEQ ID NO:1 provides an amino acid sequence that includes the variable region of anti-CD137 antibody clone #15 heavy chain. SEQ ID NO: 2 provides an amino acid sequence that includes the variable region of anti-CD137 clone #15 light chain.

The antigen binding region of an antibody or antigen binding fragment thereof generally includes complementarity determining regions (CDRs). "Complementarity determining region (CDR)" refers to hypervariable regions of $V_H$ and $V_L$. CDRs include the target protein or antigen binding site of an antibody that confers specificity for protein or antigen binding. $V_H$ and $V_L$ generally include three sequentially numbered CDRs. As used herein, CDR-H1, CDR-H2, and CDR-H3 refer to three consecutively arranged CDRs of the heavy chain variable region ($V_H$), as numbered from the N-terminus of the heavy chain polypeptide. As used herein, CDR-L1, CDR-L2, and CDR-L3 refer to three consecutively arranged CDRs of the light chain variable region ($V_L$), as numbered from the N-terminus of the light chain polypeptide.

In one aspect, the antigen binding region of the antibody or antigen binding fragment thereof having a $V_H$ region that includes an amino acid sequence having at least about 80% identity to SEQ ID NO:1 and a $V_L$ region that includes an amino acid sequence having at least about 80% identity to SEQ ID NO:2 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:3, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:4, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:5. In another aspect, the antigen binding region of the antibody or antigen binding fragment thereof having a $V_H$ region that includes an amino acid sequence having at least about 80% identity to SEQ ID NO:1 and a $V_L$ region that includes an amino acid sequence having at least about 80% identity to SEQ ID NO:2 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:6, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:7, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:8.

In some aspects, the antibody or antigen binding fragment thereof includes a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:9 and a $V_L$ region that includes an amino acid sequence having at least about 80%, identity at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 10. SEQ ID NO:9 provides an amino acid sequence that includes the variable region of anti-CD137 antibody clone #31 heavy chain. SEQ ID NO: 10 provides an amino acid sequence that includes the variable region of anti-CD137 clone #31 light chain.

In one aspect, the antigen binding region of the antibody or antigen binding fragment thereof that includes a $V_H$ region including an amino acid sequence having at least about 80% identity to SEQ ID NO:9 and a $V_L$ region including an amino acid sequence having at least about 80% identity to SEQ ID NO:10 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 11, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 12, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:13. In another aspect, the antigen binding region of the antibody or antigen binding fragment thereof that includes a $V_H$ region including an amino acid sequence having at least about 80% identity to SEQ ID NO:9 and a $V_L$ region that includes an amino acid sequence having at least about 80%, identity to SEQ ID NO:10 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 14, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 15, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:16.

In some aspects, the antibody or antigen binding fragment thereof has a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 17 and a $V_L$ region that includes an amino acid sequence having at least about 80%, identity at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 18. SEQ ID NO:17 provides an amino acid sequence that includes the variable region of anti-CD137 antibody clone #54 heavy chain. SEQ ID NO: 18 provides an amino acid sequence that includes the variable region of anti-CD137 clone #54 light chain.

In one aspect, the antigen binding region of the antibody or antigen binding fragment thereof that includes a $V_H$ region including an amino acid sequence having at least about 80% identity to SEQ ID NO:17 and a $V_L$ region including an amino acid sequence having at least about 80% identity to SEQ ID NO:18 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 19, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:20, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:21. In another aspect, the antigen binding region of the antibody or antigen binding fragment thereof that includes a $V_H$ region including an amino acid sequence having at least about 80% identity to SEQ ID NO:17 and a $V_L$ region including an amino acid sequence having at least about 80%, identity to SEQ ID NO:18 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:22, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO: 23, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:24.

Antibodies or antigen binding fragments thereof provided herein further include an Fc domain. As used herein, the term Fc domain refers to an antibody region that includes at least a hinge region, a CH2 domain, and a CH3 domain, unless context clearly indicates otherwise. The terms Fc domain and Fc region may be used interchangeably, unless context clearly indicates otherwise. In certain aspects, the Fc domain is an IgG domain, an IgE domain, an IgM domain, and IgD domain, an IgA domain, or an IgY domain. Fc domains of any sequence and from any species can be used, including human, ape, monkey, mouse, rabbit, goat, sheep, guinea pig, horse, and others. In certain aspects, Fc domains are engineered, i.e., non-naturally occurring or recombinant Fc domains generated using techniques of molecular biology, for example. In some aspects, the IgG domain is an IgG1 domain, an IgG2 domain, an IgG3 domain, or an IgG4 domain. In one aspect, the IgG4 domain includes an amino acid sequence of SEQ ID NO:25. In another aspect, the IgG1 domain includes an amino acid sequence of SEQ ID NO:26. In one aspect, the Fc domain is human.

Also provided herein, in some embodiments, are pharmaceutical compositions including any of the antibodies or antigen binding fragments thereof provided herein and a pharmaceutically acceptable carrier. In some aspects, the pharmaceutically acceptable carrier is conjugated to the C-terminus of one or more polypeptides of the antibody or antigen binding fragment. Any suitable means of conjugating the pharmaceutically acceptable carrier can be used, including covalent conjugation and use of linkers, for example.

In some embodiments, provided herein are isolated amino acid sequences as set forth in SEQ ID NOs:1-26. Also provided herein, in some embodiments, are isolated nucleic acid sequences that encode any one of the amino acid sequences of SEQ ID NOs:1-26.

In some embodiments, methods of treating cancer in a subject are provided herein. In some aspects, methods of treating cancer include administering to a subject an amount of any of the antibodies or antigen binding fragments thereof provided herein that bind CD137, effective for treating the cancer. In some aspects, the cancer is prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the term "effective amount" or "therapeutically effective amount" refers to that amount of an antibody, an antigen binding fragment thereof, or other composition described herein that is sufficient to effect the intended application, including but not limited to disease treatment, as defined herein. The therapeutically effective amount may vary depending upon the intended treatment application (e.g., in vivo), or the patient and disease condition being treated, e.g., the weight and age of the patient, the severity of the disease condition, the manner of administration and the like, which can readily be determined by one of ordinary skill in the art. The term also applies to a dose that will induce a particular response in a target cell. The specific dose will vary depending on the particular antibody, an antigen binding fragment thereof, or other composition chosen, the dosing regimen to be followed, whether it is administered in combination with other compounds, timing of administration, the tissue to which it is administered, and the physical delivery system in which it is carried.

In some aspects, antibodies of the invention or antigen binding fragments thereof are used as a monotherapy or combined with other therapeutic agents such as radiotherapy, cytotoxic chemotherapy, and other immunoregulatory agents, such as vaccines, interleukins, cytokines, chemokines, and biologics as a combination therapy. Exemplary interleukins for immune therapy include IL-1, IL-2, IL-3, IL-4, IL-5, IL-6, IL-7, IL-8, IL-10, IL-12, IL-15, IL-18, IL-21, and IL-23. Exemplary cytokines for immune therapy include interferons, TNF-α, TGF-β, G-CSF, and GM-CSF. Exemplary chemokines for immune therapy include CCL3, CCL26, and CXCL7. Exemplary biologics include CAR T-cell therapy, tumor-infiltrating lymphocyte (TIL) therapy, and monoclonal antibodies, such as alemtuzumab (CAMPATH), trastuzumab (HERCEPTIN), ibritumomab tiuxetan (ZEVALIN), brentuximab vedotin (ADCETRIS), ado-trastuzumab emtansine (KADCYLA), blinatumomab (BLINCYTO), bevacizumab (AVASTIN), and cetuximab (ERBITUX). Antibodies also include checkpoint inhibitors, including PD-1 inhibitors, such as pembrolizumab (KEYTRUDA), nivolumab (OPDIVO), and cemiplimab (LIBTAYO), for example, PD-L1 inhibitors, such as atezolizumab (TECENTRIQ), avelumab (BAVENCIO) and durvalumab (IMFINZI), for example, CTLA-4 inhibitors, such as iplimumab (YERVOY), for example, and other checkpoint inhibitors, such as an anti B7-H3 antibody (MGA271), an anti-KIR antibody (lirilumab) and an anti-LAG3 antibody (BMS-986016), for example.

In some embodiments, the invention further provides the expression, purification and characterization of anti-CD137 agonist antibodies, as detailed in the examples below. A signal sequence can be included in expression constructs for antibodies provided herein. Any suitable signal sequence can be used, such as a sequence of SEQ ID NO:27. In some aspects, T cells treated with anti-PD-L1 antibody together with anti-CD137 antibodies provided herein showed a further increase in T-cell effector function. Without being limited by theory, this indicates that combination treatment or treatment with bispecific antibodies targeting both CD137 and PD-L1 may overcome a lower response rate of monotherapy seen with each antibody alone in clinical trials. In addition to anti-PD-L1 antibody, a second antibody for combination treatment that targets other immune potentiating antigens, such as CD40 or CTLA-4, or treatment with a bispecific antibody targeting CD137 and a second antigen such as PD-L1, CD40, or CTLA-4, for example, can be used.

Bispecific molecules, such as bispecific antibodies (bs-Abs), provide a means for simultaneously targeting multiple epitopes on the same or different molecular targets with a single therapeutic agent. Without being limited by theory, bispecific molecules as cancer therapeutics have the potential to confer novel or more potent activities, lower the cost of goods, and facilitate the development of new therapeutic regimens as compared to a mixture of two monoclonal antibodies (mAbs), for example.

Accordingly, also provided herein is the expression, purification, and characterization of bi-functional proteins, including bispecific antibodies. As used herein, the term "bi-functional protein" refers to a protein that has at least two functions. A non-limiting example of a bi-functional protein includes a bispecific antibody that is capable of binding to two antigens. Bispecific antibodies provided herein can include isolated, functional scFv fragments that bind to CD137 and that are fused to the C-terminus of the Fc domain of an anti-PD-L1 antibody, for example. In some aspects, a C-terminally positioned scFv that binds CD137 in fusion constructs provided herein is fused to an Fc domain of an antibody that binds to other immunoregulatory molecules, such as CD40 or CTLA-4, for example. In other aspects, a C-terminally positioned scFv can bind to an immunoregulatory molecule, such as CD40 or CTLA-4, for example.

Provided herein, in some embodiments, are bispecific antibodies that include a first antigen binding region and a second antigen binding region. Generally, the first antigen binding region and the second antigen binding region specifically bind to different antigens or targets. In some aspects, the first antigen binding region and the second antigen binding region bind to different epitopes in the same antigen or target.

In an embodiment, bispecific antibodies provided herein include a first antigen binding region that binds to CD137. The first antigen binding region includes a $V_H$ region that includes an amino acid sequence having at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, at least 99.5% identity, at least 99.9% identity, and any number or range in between, to a sequence selected from SEQ ID NO: 1; SEQ ID NO:9; and SEQ ID NO:17 and a $V_L$ region that includes an amino acid sequence having at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, at least 99.5% identity, at least 99.9% identity, and any number or range in between, to about 100 to 120 amino acids of an N-terminal sequence of a sequence selected from SEQ ID NO:2; SEQ ID NO:10; and SEQ ID NO:18. In some aspects, the second antigen binding region of bispecific antibodies provided herein binds to an immune checkpoint molecule, an immune stimulatory molecule, or a tumor antigen.

Any number of amino acids of sequences as set forth in SEQ ID NO:1, SEQ ID NO:9, and SEQ ID NO:17 that include a $V_H$ region or as set forth in SEQ ID NO:2, SEQ ID NO:10, or SEQ ID NO:18 that include a $V_L$ region can be included in bispecific antibodies. N-terminal or C-terminal sequences of sequences provided herein having a $V_H$ region or a $V_L$ region can be included in bispecific antibodies. In one aspect, about 100 to 105 amino acids, about 100 to 110 amino acids, about 100 to 115 amino acids, about 100 to 120 amino acids, about 100 to 125 amino acids, and any number or range in between, of an N-terminal or of a C-terminal sequence of SEQ ID NO:1, SEQ ID NO:2, SEQ ID NO:9, SEQ ID NO: 10, SEQ ID NO:17, or SEQ ID NO:18 is included in bispecific antibodies provided herein. In another aspect, bispecific antibodies include a sequence of SEQ ID NO:1, SEQ ID NO:9, or SEQ ID NO:17. In yet another aspect, bispecific antibodies include about 100 to 120 amino acids of an N-terminal sequence of SEQ ID NO:2, SEQ ID NO: 10, or SEQ ID NO:18. In yet a further aspect, bispecific antibodies include about 112 amino acids of an N-terminal sequence of SEQ ID NO: 10 or about 108 amino acids of an N-terminal sequence of SEQ ID NO:18.

In one aspect, the first antigen binding region of bispecific antibodies provided herein includes a $V_H$ region having an amino acid sequence of SEQ ID NO:9 and a $V_L$ region having an amino acid sequence of about 100 to 120 amino acids of an N-terminal sequence of SEQ ID NO:10. In another aspect, the first antigen binding region of bispecific antibodies provided herein includes a $V_H$ region having an amino acid sequence of SEQ ID NO:17 and a $V_L$ region having an amino acid sequence of about 100 to 120 amino acids of an N-terminal sequence SEQ ID NO:18.

In some aspects, the second antigen binding region of bispecific antibodies provided herein binds to an immune checkpoint molecule, an immune stimulatory molecule, or a tumor antigen. As used herein, the term "immune checkpoint molecule" refers to any molecule that inhibits or negatively regulates immune responses. In one aspect, binding of the second antigen binding region to an immune checkpoint molecule inhibits the immune checkpoint molecule. Exemplary immune checkpoint molecules include PD-L1, PD-1, CTLA-4, and LAG3. As used herein, the term "immune stimulatory molecule" refers to any molecule that induces, enhances, or positively regulates immune responses. Exemplary immune stimulatory molecules include CD28, CD40, CD137, CD27, and ICOS. In some aspects, binding of the second antigen binding region to an immune stimulatory molecule activates the immune stimulatory molecule, resulting in increased signaling and increased immune activation, for example. As used herein, the term "tumor antigen" refers to any antigen that is present on the surface of a tumor cell or expressed in a tumor cell. Exemplary tumor antigens include products of mutated oncogenes, products or mutated tumor suppressor genes, products of mutated genes other than oncogenes or tumor suppressors, tumor antigens produced by oncogenic viruses, altered cell surface glycolipids and glycoproteins, oncofetal antigens, and others. Tumor antigens also include immune regulatory molecules, such as immune checkpoint inhibitors and immune stimulatory molecules. Accordingly, in some aspects, the tumor antigen the second antigen binding region of bispecific antibodies provided herein binds to functions as an immune regulatory molecule. In one aspect, binding of the second antigen binding region to a tumor antigen results in targeting an immune cell, such as a T cell, to a tumor cell, for example.

Any combination of first and second antigen binding regions can be included in bispecific antibodies provided herein, including first and second antigen binding regions that bind to any immune checkpoint molecule, any immune stimulatory molecule, or any tumor antigen, for example. Accordingly, in some aspects, the second antigen binding region of bispecific antibodies provided herein binds to any immune checkpoint molecule, any immune stimulatory molecule, or any tumor antigen. In some aspects, the first and second antigen binding regions bind to the same molecule. For example, the first and second antigen binding regions may bind to the same or to a different epitope of the same molecule. In other aspects, the first and second antigen binding regions bind to different molecules.

In some aspects, the second antigen binding region binds to an antigen selected from PD-L1, PD-1, CTLA-4, LAG3, CD28, CD40, CD137, CD27, ICOS, human epidermal growth factor receptor 2 (Her2), or a glycan. Exemplary glycans include N-glycans, O-glycans, and glycosphingolipids. A glycan may be expressed exclusively in cancer cells, such as GloboH, for example. In one aspect, the second antigen binding region binds to PD-L1. In another aspect, the second antigen binding region binds to Her2. In yet another aspect, the second antigen binding region binds to a glycan. In a further aspect, the glycan is GloboH. Expanding the repertoire of bispecific antibodies to bind to CD137 and antigens expressed on tumors in addition to or other than PD-L1 allows for targeting bispecific antibodies to cancer types that do not express PD-L1, for example.

Figure 16:
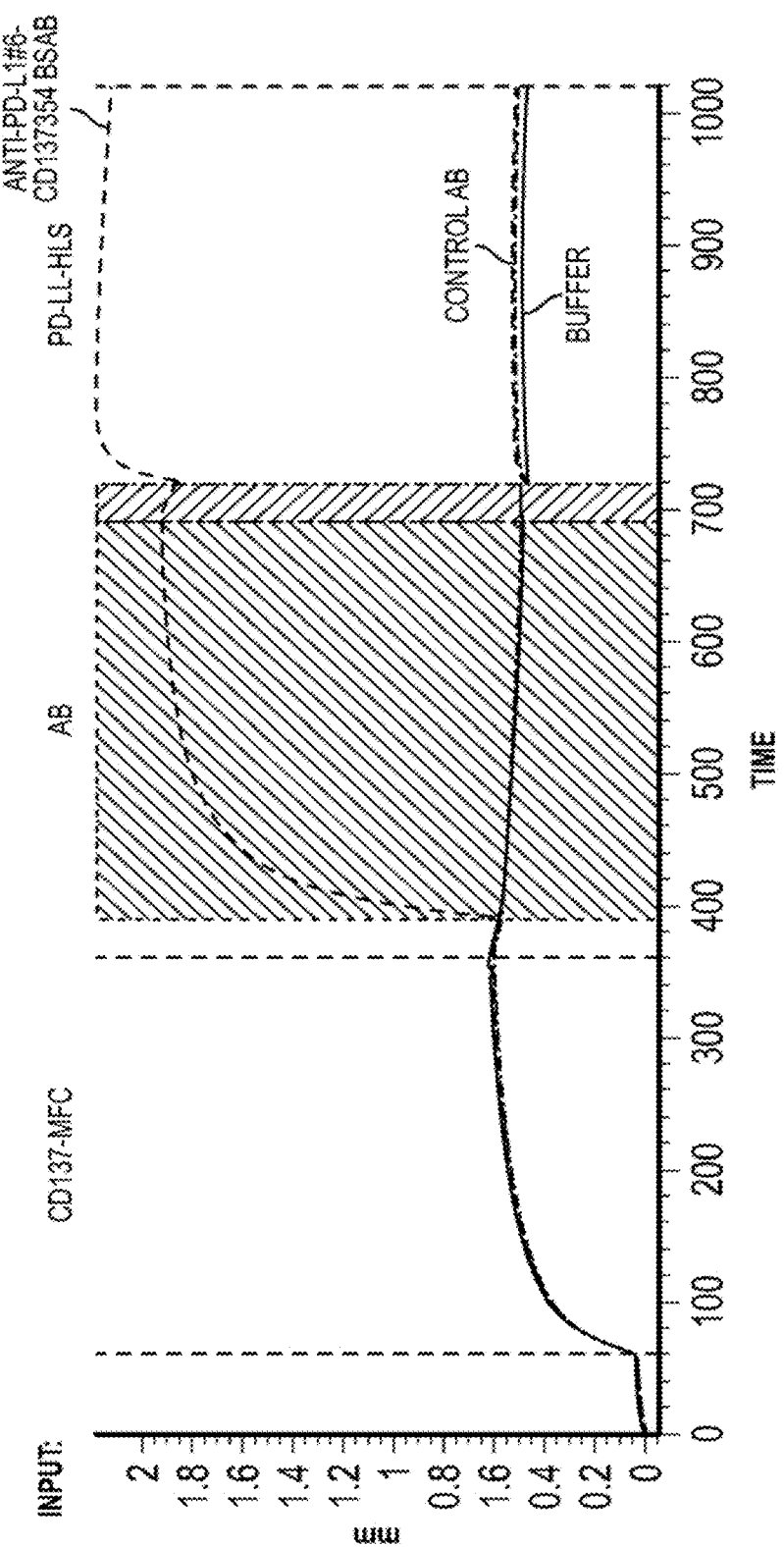
FIG. 16 shows that anti-PD-L1-CD137 bsAbs simultaneously recognize CD137 and PD-L1, as seen by FortéBio® biosensor analysis.
Figure 16:
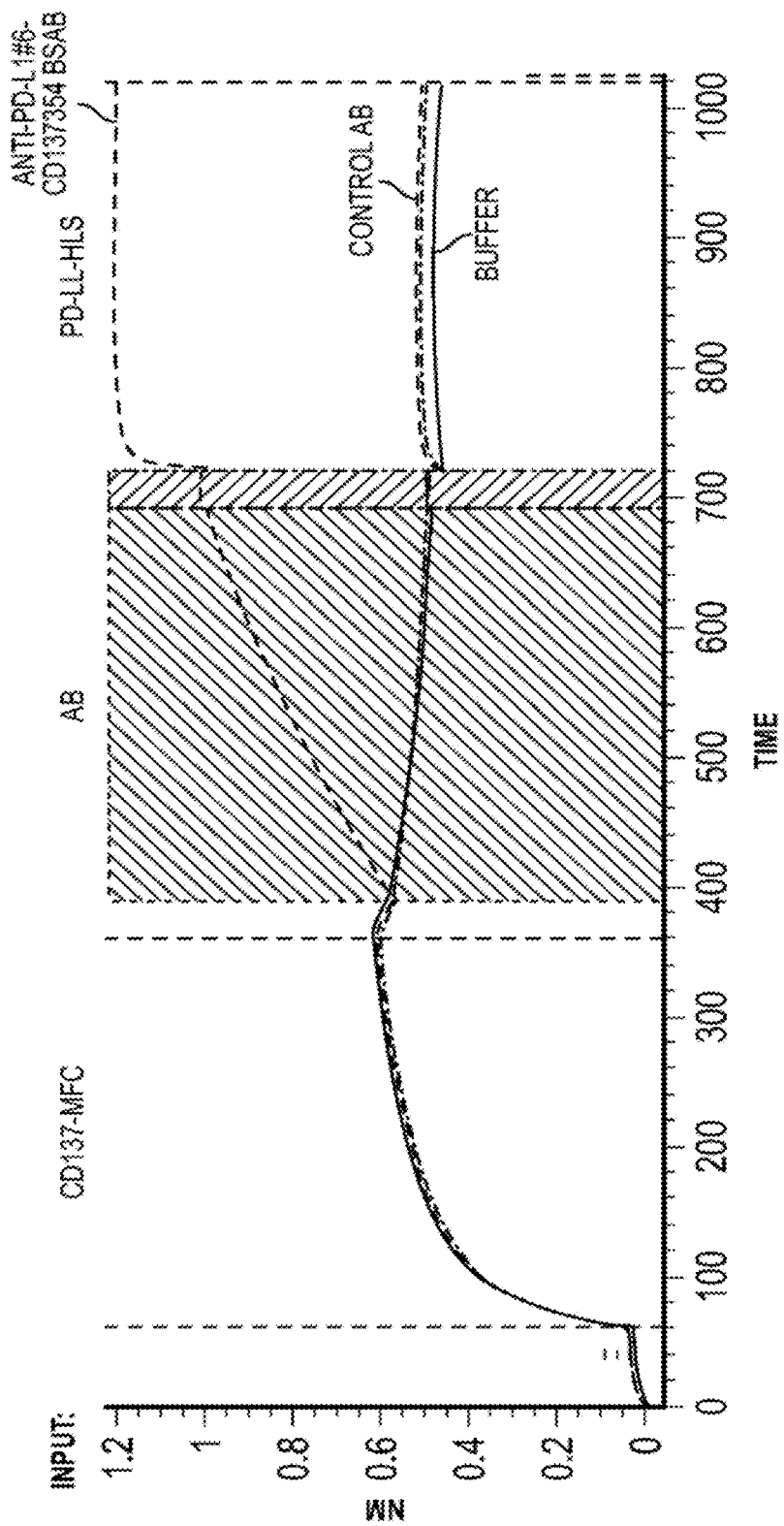
Figure 23:
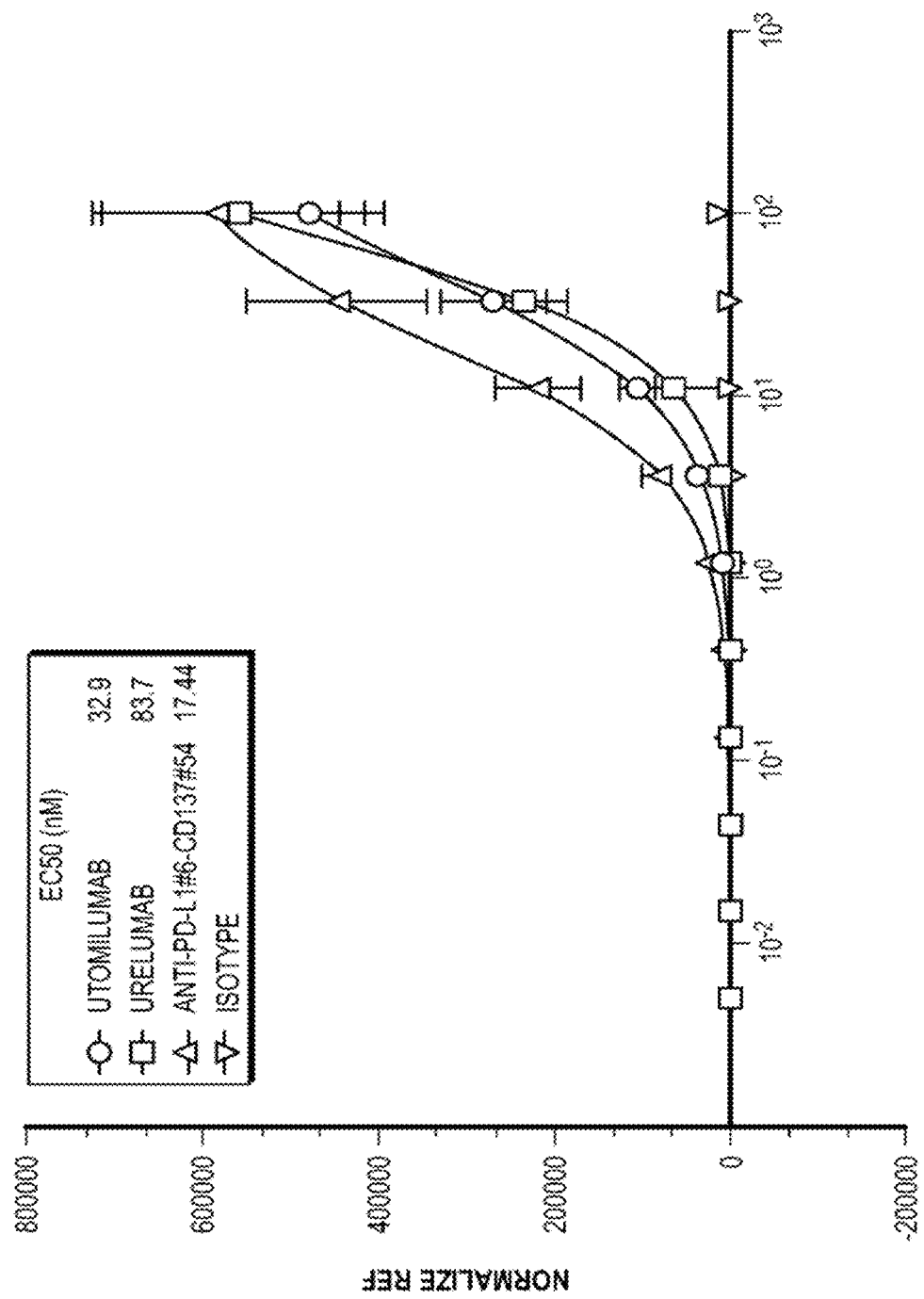
FIG. 23 shows that anti-PD-L1 #6-CD137 #54 bsAb induces internalization of CD137 expressed on HEK293 cells.

In one aspect, bispecific antibodies having a first antigen binding region that binds to CD137 and a second antigen binding region that binds to PD-L1 bind to CD137 and PD-L1 simultaneously (FIG. 16). Without being limited by theory, restricting anti-CD137 binding activity to tumor sites that express PD-L1 by designing bispecific antibodies that are able to bind to both CD137 and PD-L1 may reduce the risk of hepatotoxicity and its associated fatality seen in clinical trials with anti-CD137 antibodies such as Urelumab. In addition, it is believed that simultaneous binding to CD137 and PD-L1 may enhance T-cell activation as a result of cross-linking (see also Example 10 below). In another aspect, bispecific antibodies having a first antigen binding region that binds to CD137 and a second antigen binding region that binds to PD-L1 induce stronger CD137 internalization compared to reference antibodies such as Utomilumab and Urelumab (FIG. 23).

In some aspects, first antigen binding regions and second antigen binding regions include an scFv, an F(ab)2, an Fab, or any combination thereof. In one aspect, the first antigen binding region includes an scFv and the second antigen binding region includes an Fab. In another aspect, an scFv included in bispecific antibodies provided herein binds to an immune checkpoint molecule, an immune stimulatory molecule, or a tumor antigen. In yet another aspect, an scFv included in bispecific antibodies provided herein binds to a CD137. In some aspects, an Fab included in bispecific antibodies provided herein binds to an immune checkpoint molecule, an immune stimulatory molecule, or a tumor antigen. In one aspect, an Fab included in bispecific antibodies provided herein binds to PD-L1. In another aspect, the scFv of bispecific antibodies provided herein includes a $V_H$ region that includes an amino acid sequence of SEQ ID NO:9 and a $V_L$ region that includes an amino acid sequence of about 100 to 120 amino acids of an N-terminal sequence of SEQ ID NO: 10. In yet another aspect, the scFv of bispecific antibodies provided herein includes a $V_H$ region that includes an amino acid sequence of SEQ ID NO:17 and a $V_L$ region that includes an amino acid sequence of about 100 to 120 amino acids of an N-terminal sequence of SEQ ID NO: 18.

In one aspect, bispecific antibodies provided herein include a first antigen binding region that binds CD137 and a second antigen binding region that binds Her2. Bispecific antibodies that bind CD137 and Her2 include an scFv that binds CD137 fused to the C-terminus of the Fc domain of antibodies that bind to Her2, such as Trastuzumab (heavy chain SEQ ID NO:36) or anti-Her2 #3-7 (heavy chain SEQ ID NO:38). In certain aspects, bispecific antibodies that bind CD137 and Her2 further include a light chain of SEQ ID NO:35 (Trastuzumab) or SEQ ID NO:37 (anti-Her2 #3-7). In another aspect, bispecific antibodies provided herein include a first antigen binding region that binds CD137 and a second antigen binding region that binds a tumor-specific glycan. Bispecific antibodies that bind CD137 and a tumor-specific glycan include an scFv that binds CD137 fused to the C-terminus of the Fc domain of antibodies that bind to the tumor-specific glycan, such as anti-glycan provided herein (heavy chain SEQ ID NO:40). In certain aspects, bispecific antibodies that bind CD137 and a tumor-specific glycan further include a light chain of SEQ ID NO:39 (anti-glycan). In some aspects, bispecific antibodies that bind CD137 and Her2 or CD137 and a tumor-specific glycan further include a linker that links the anti-CD137 scFv to the Fc domain. Any linker can be used, such as GS linkers (SEQ ID NO:28), G4S linkers (SEQ ID NO:29), or multiples thereof. In one aspect, the linker is a G4S linker.

Accordingly, the present invention provides a platform of target-dependent T-cell activation. In one aspect, the agonist activity of an anti-CD137 scFv is induced upon binding to tumor-specific antigens such as PD-L1, for example, as shown in FIGS. 19 and 20A-20C. Anti-CD137 agonist activity can also be activated by binding to other tumor-specific antigens, such as Her2 and tumor-specific glycans, as shown in FIGS. 21A-21B and 22A-22B.

In some aspects, bispecific antibodies provided herein further include a linker between the $V_H$ region and the $V_L$ region of the scFv. Any linker can be used. For example, linkers can include any amino acid sequence. Linkers can be of any length, such as one amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, or more amino acids. Linkers can also include multiples of an amino acid sequence. Any number of multiples of an amino acid sequence can be included in a linker. Exemplary linker sequences are provided in SEQ ID NO:28 and SEQ ID NO:29. In some aspects, the scFv includes an amino acid sequence of SEQ ID NO:33 or SEQ ID NO:34.

In some aspects, bispecific antibodies provided herein further include an Fc domain. In certain aspects, the Fc domain is an IgG domain, an IgE domain, an IgM domain, and IgD domain, an IgA domain, or an IgY domain. Fc domains of any sequence and from any species can be used, including human, ape, monkey, mouse, rabbit, goat, sheep, guinea pig, horse, and others. In some aspects, the IgG domain is an IgG1 domain, an IgG2 domain, an IgG3 domain, or an IgG4 domain. In one aspect, the IgG4 domain includes an amino acid sequence of SEQ ID NO:25. In another aspect, the IgG1 domain includes an amino acid sequence of SEQ ID NO:26. In one aspect, the Fc domain is human. Generally, human Fc domains are not immunogenic in humans and are therefore suitable for use in human therapeutics.

In some aspects, the scFv of bispecific antibodies provided herein is conjugated to the C-terminus of the Fc domain. In one aspect, a linker is included between the Fc domain and the scFv. In another aspect, a linker links the scFv to the Fc domain. Any linker can be used, such as G4S linkers provided herein.

In some aspects, the Fab of bispecific antibodies provided herein is linked to the N-terminus of the Fc domain. In one aspect, the Fab is linked directly to the N-terminus of the Fc domain via a peptide bond. In another aspect, the Fab domain is linked to the N-terminus of the Fc domain via a linker.

In some aspects, bispecific antibodies provided herein include a heavy chain sequence of SEQ ID NO:31 or SEQ ID NO:32. In another aspect, bispecific antibodies provided herein further include a light chain sequence of SEQ ID NO: 30. In one aspect, bispecific antibodies provided herein include a heavy chain sequence of SEQ ID NO:36. In another aspect, bispecific antibodies provided herein further include a light chain sequence of SEQ ID NO:35. In one aspect, bispecific antibodies provided herein include a heavy chain sequence of SEQ ID NO:38. In another aspect, bispecific antibodies provided herein further include a light chain sequence of SEQ ID NO:37. In one aspect, bispecific antibodies provided herein include a heavy chain sequence of SEQ ID NO:40. In another aspect, bispecific antibodies provided herein further include a light chain sequence of SEQ ID NO:39. Heavy chain sequences such as SEQ ID NO:31, SEQ ID NO:32, SEQ ID NO:36, SEQ ID NO:38, SEQ ID NO:40, and others, can include one or more G linkers (SEQ ID NO:28), one or more G4S linkers (SEQ ID NO:29), or any multiple of a G linker or G4S linker, although any other suitable linker can be used.

In some embodiments, provided herein are isolated amino acid sequences as set forth in SEQ ID NOs:30-40. Also provided herein, in some embodiments, are isolated nucleic acid sequences encoding any one of the amino sequences of SEQ ID NOs:30-40.

In some embodiments, provided herein are antibody-drug conjugates. Antibody-drug conjugates provided herein can include any antibody or antigen binding fragment thereof provided herein. For example, any antibody or antigen binding fragment thereof that specifically binds to CD137 can be included in antibody-drug conjugates. Any bispecific antibody or antigen binding fragment thereof provided herein can also be included in antibody-drug conjugates. In some aspects, antibody-drug conjugates provided herein include a therapeutic agent. Any therapeutic agent can be included in antibody-drug conjugates provided herein, including small molecules. In some aspects, the therapeutic agent has cytotoxic activity. Any chemotherapeutic agent that has cytotoxic activity can be included in antibody-drug conjugates. Exemplary chemotherapeutic agents include, but are not limited to, actinomycin, all-trans retinoic acid, anti-estrogens, azacitidine, azathioprine, bleomycin, bortezomib, carboplatin, capecitabine, cisplatin, chlorambucil, cyclophosphamide, cytarabine, dacarbazine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitomycin C, mitoxantrone, oxaliplatin, paclitaxel, pemetrexed, taxol, taxotere, tamoxifen, teniposide, tioguanine, topotecan, valrubicin, vemurafenib, vinblastine, vincristine, and vindesine.

In some aspects, antibody-drug conjugates provided herein are used for the treatment of cancer. For example, an antibody included in an antibody-drug conjugate binds to an antigen on tumor cells, thereby targeting a small molecule with cytotoxic activity or other therapeutic agent included in the antibody-drug conjugate to tumor cells. Upon binding of the antibody-drug conjugate to tumor cells, the small molecule or other therapeutic agent is internalized and released in tumor cells.

In some aspects, the therapeutic agent included in antibody-drug molecules provided herein is covalently linked to an antibody or antigen binding fragment thereof provided herein or to a bispecific antibody or antigen binding fragment thereof provided herein. A linker can be used to covalently link the therapeutic agent to the antibody or antigen binding fragment thereof or to the bispecific antibody or antigen binding fragment thereof. Any suitable linker can be used to covalently link a therapeutic agent to an antibody or antigen binding fragment thereof provided herein or to a bispecific antibody or antigen binding fragment thereof provided herein. In some aspects, the linker included in antibody-drug conjugates provided herein is stable outside of target cells, including in the circulation, and cleaved inside target cells to release the therapeutic agent. A therapeutic agent with cytotoxic activity, for example, can induce target cell death upon release. Accordingly, in some aspects, a therapeutic agent is selectively targeted to tumor cells. Selective targeting of a therapeutic agent to tumor cells generally results in reduced cytotoxicity to non-tumor cells and increased tolerability, for example.

Provided herein, in some embodiments, are pharmaceutical compositions that include a bispecific antibody provided herein. Any bispecific antibody provided herein can be included in a pharmaceutical composition. In one aspect, bispecific antibodies included in pharmaceutical compositions provided herein bind to CD137, PD-L1, or both CD137 and PD-L1. Antibody-drug conjugates provided herein can also be included in pharmaceutical compositions. In some aspects, pharmaceutical compositions are used for the treatment of cancer. Any cancer can be treated using a pharmaceutical composition provided herein. Exemplary cancers include prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, and leukemia.

In some embodiments, methods of treating cancer in a subject are provided herein. Methods of treating cancer include administering to a subject an amount of any bispecific antibody or an antigen binding fragment thereof provided herein, effective for treating the cancer. In some aspects, the cancer is prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

EXAMPLES

Example 1

This example illustrates antibody generation from an OmniMab library.

To generate therapeutic antibodies against CD137, selections with an OmniMab phagemid library were carried out. The phagemid library was built up by AP Biosciences Inc. (APBio Inc.) from a collection of peripheral blood mononuclear cells from over a hundred healthy donors. Pre-coated CD137-Fc recombinant protein was incubated with supernatant containing rescued phages for 1 hour and washed three with PBS containing 0.1% Tween-20. Bound phages were detected by HRP conjugated anti-M13 antibody (Roche) and TMB substrate was used for signal development. The OD450 readings were recorded.

Figure 2:
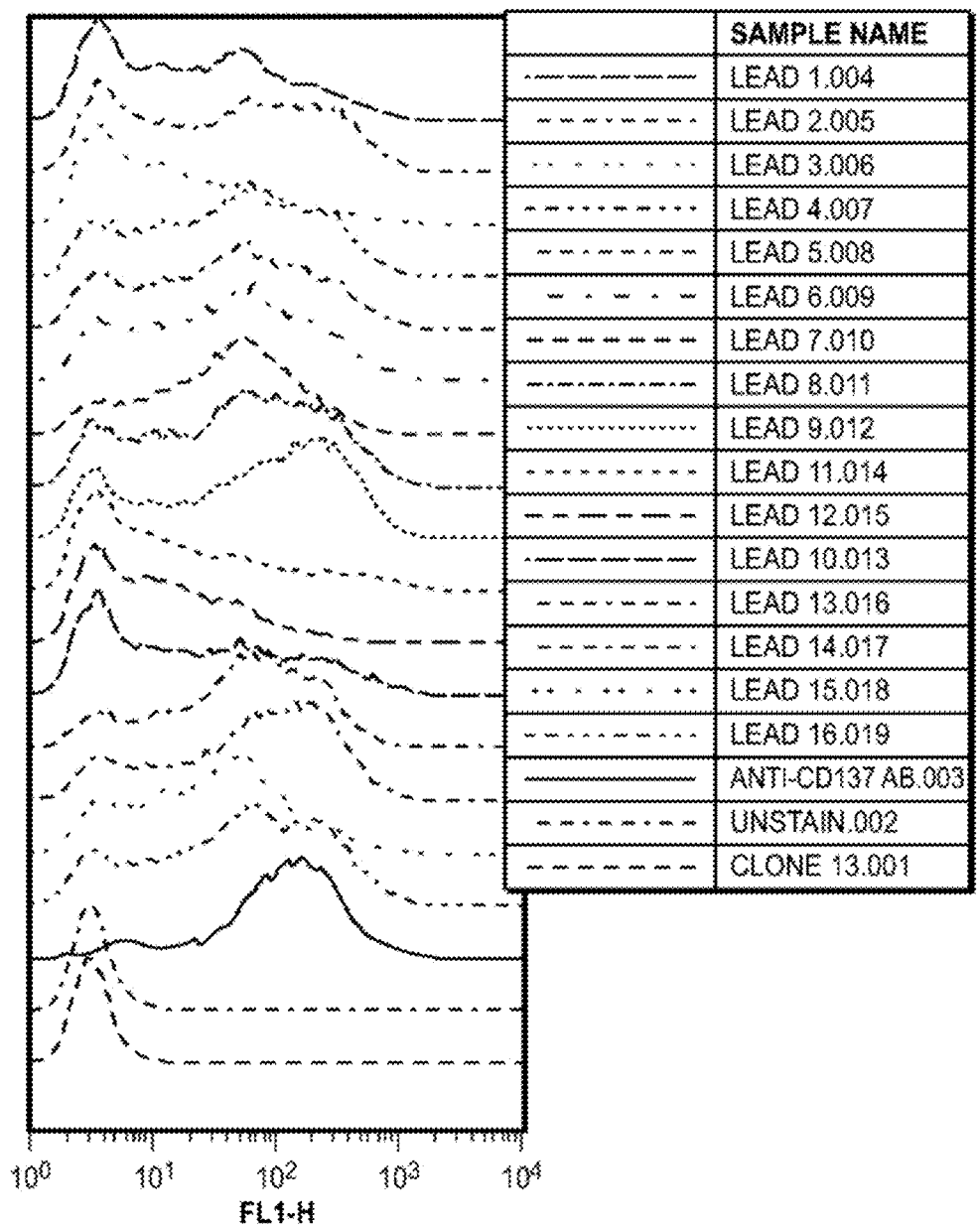
FIG. 2 shows the binding of phage clones targeted to CD137 on CD137-overexpressing HEK-293F cells by flow cytometry.
Figure 2:
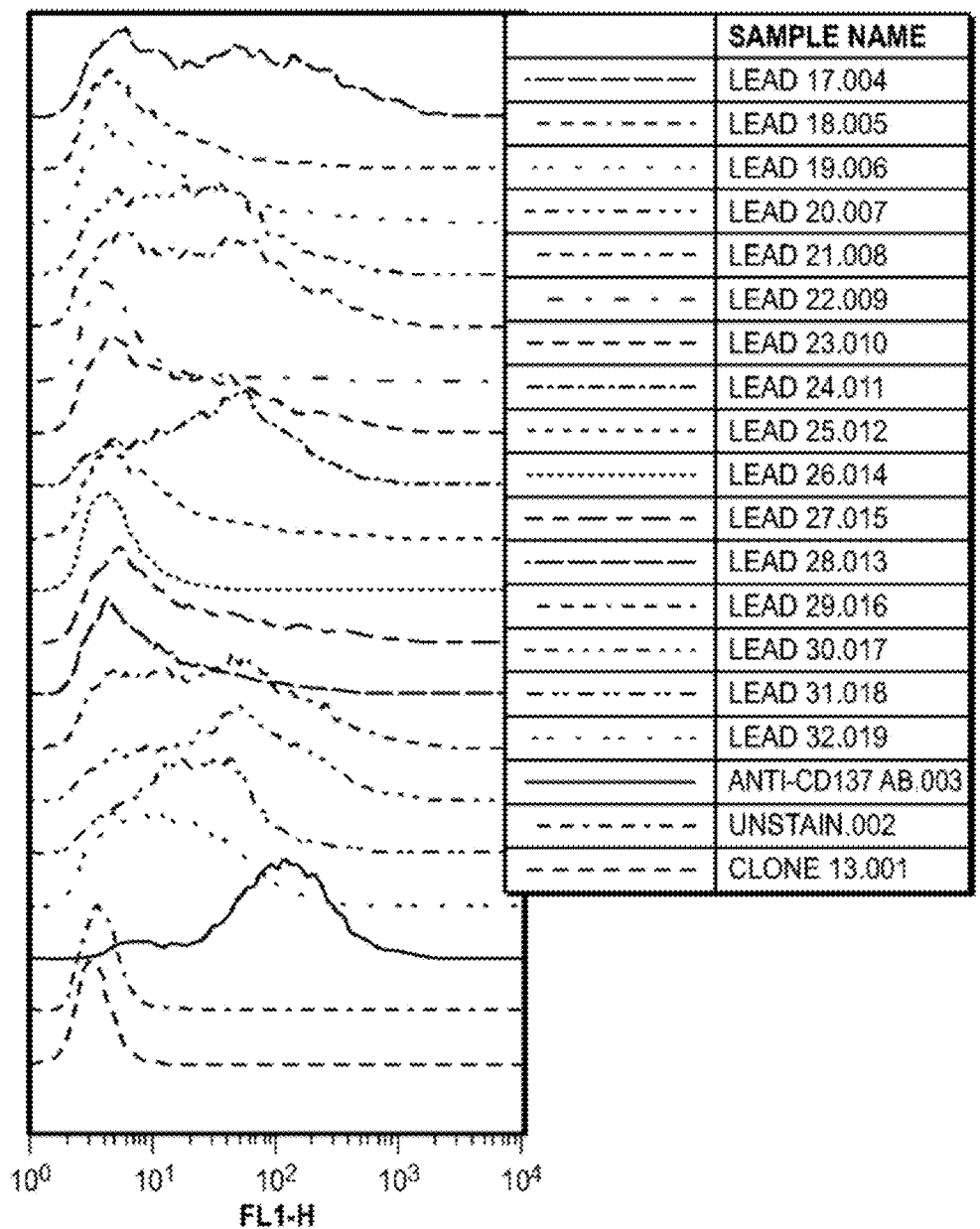
Figure 2:
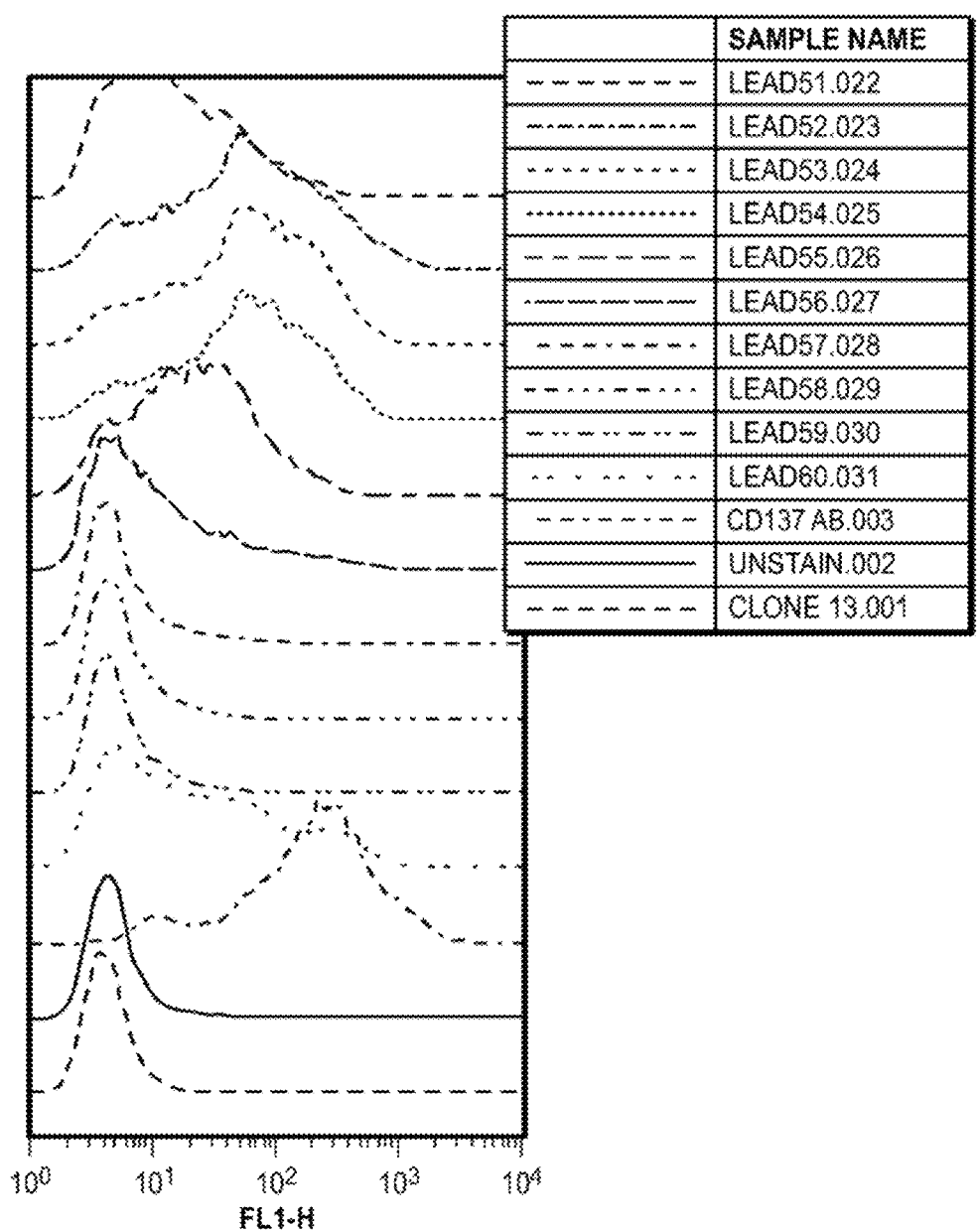

First round panning was performed using Hyperphage (M13K07ΔpIII, Progen, Heidelberg, Germany). Solid phase panning and cell panning against CD137 were used for CD137-specific binder selection and isolation from the OmniMab library. Solid phase panning was performed using recombinant human CD137-ECD-Fc (APBio Inc.) used in first-round selection. CD137-expressing HEK293 cells were used for second and third round enrichment. The specific CD137 binders were screened and isolated by direct ELISA and FACS after three rounds panning (FIG. 1 and FIG. 2). For FACS analysis, 293F cells stably expressing CD137 were stained with anti-CD137 phage supernatant (50 ul/well) to examine CD137 binding activity. 293F cells stably expressing CD137 were also incubated with 2.5 ug/ml anti-CD137 antibodies (Abs) as control on ice for 1 hr. The cells were washed three times with 1×PBS and then incubated with anti-M13 antibody (Progen) on ice for 1 hr. Cells were again washed three times with 1×PBS and then incubated with anti-mouse IgG-Alexa 488 (Invitrogen Inc.) on ice for an additional 1 hr. After staining, the cells were washed three times with 1×PBS, resuspended in 1×PBS before analysis by FACS Calibur (BD Biosciences, Inc.) and FlowJo (TreeStar, LLC). FACS analysis for 293F cells clone 13 stably expressing CD137 is shown in FIG. 2. Positive binders were isolated and sent for sequencing to confirm the sequence and diversity of the heavy chain. As shown in FIG. 1 and FIG. 2, several clones were isolated that specifically recognized CD137 antigen as compared with negative control.

These results show that phage clones obtained after three rounds of CD137-specific enrichment specifically recognize CD137.

Example 2

This example illustrates subcloning, expression, and purification of CD137-specific binding proteins in the form of IgGs.

To quickly screen for candidates with functionality in T cell activation, the heavy chains and light chains of positive CD137 or PD-L1 binders identified by ELISA were amplified, digested and subcloned into an IgG expression vector generated by APBio and carrying the IgG4 constant region (SEQ ID NO. 25). After sequence validation, plasmids were prepared and transfected into HEK293 cells for antibody expression using 293fectin transfection reagent (Invitrogen). After 4 days of culture, antibody secreted into serum-free medium was affinity purified from culture supernatant by Protein G chromatography. Purified antibody was concentrated, followed by dialysis in PBS buffer. The final concentration of dialyzed protein was determined using a Nano-Drop2000 spectrophotometer and the purity and integrity were determined by SDS-PAGE with or without reducing reagent.

Figure 3A:
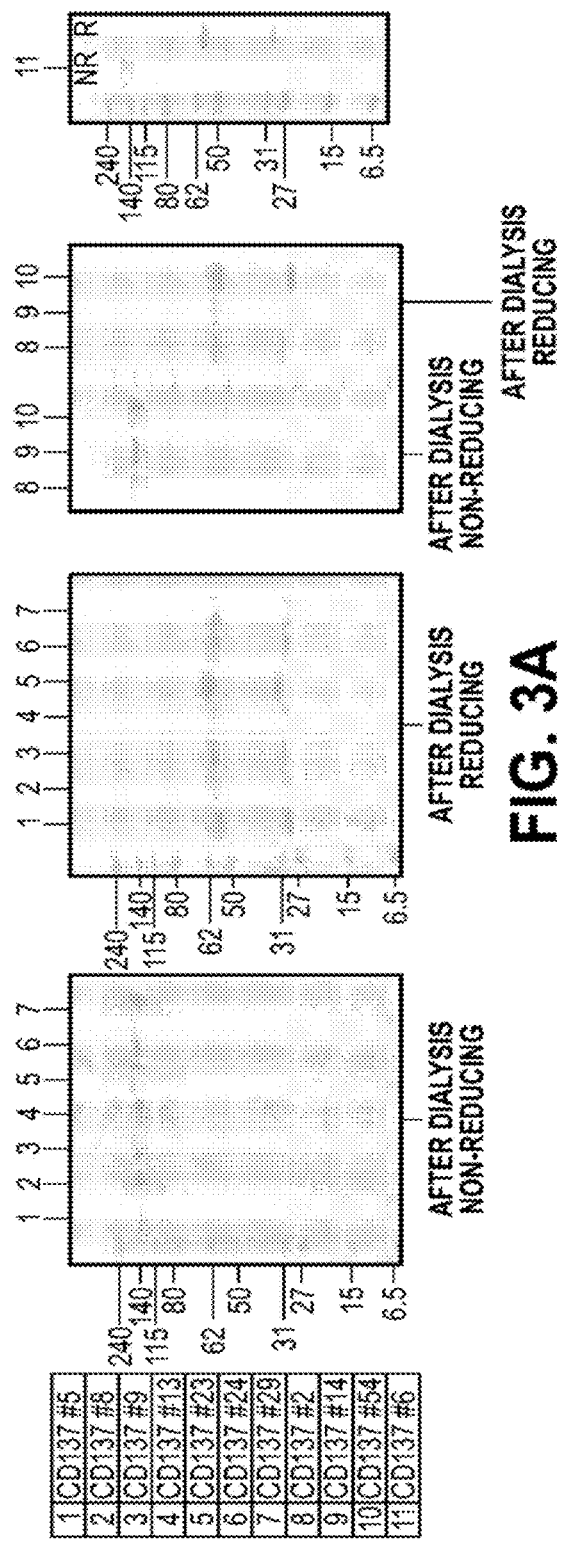
FIGS. 3A-3B show the integrity and purity of one-step Protein G-purified anti-CD137 antibody leads by PAGE. Results for two batches (top and bottom panels) are shown.
Figure 3B:
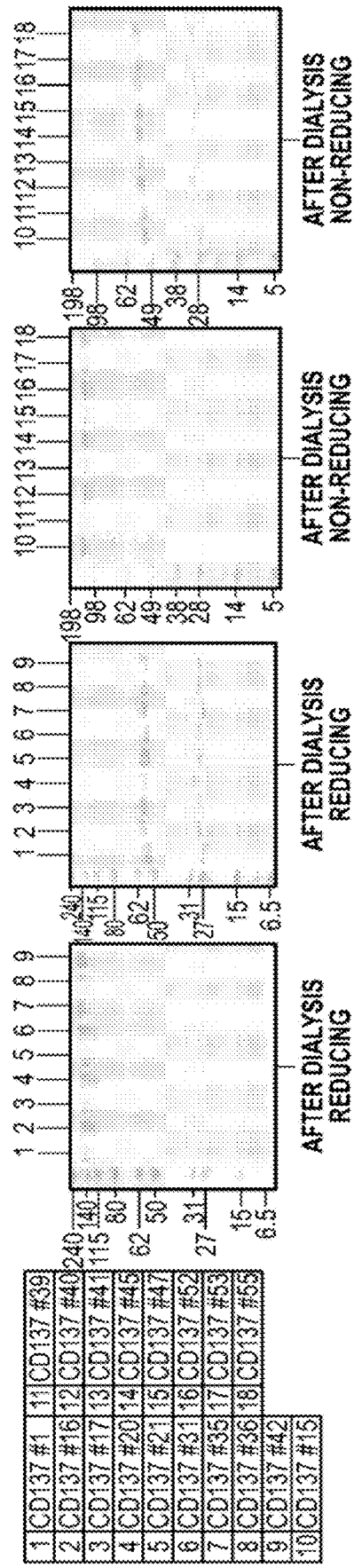

FIGS. 3A-3B show representative PAGE gel analysis of a first batch (FIG. 3A, top panels) and a second batch (FIG. 3B, bottom panels) of purified anti-CD137 antibody leads. Culture supernatants from mammalian cells collected 4 days post-transfection were purified using Protein G chromatography (Thermo Fisher). The purified proteins were analyzed under reducing or non-reducing condition before loading on the gel (3 ug/lane). Results indicated that both proteins have a molecular weight of about 145 kDa under non-reducing conditions, and heavy chain and light chain have a molecular weight of ~55 kDa and ~25 kDa, respectively, under reducing conditions. More than 90% purity could be obtained by one step of Protein G chromatography.

These results show that the integrity of various purified antibody leads is normal in the HEK293 cells.

Example 3

This example illustrates binding of anti-CD137 antibody to Jurkat cells.

Figure 4:
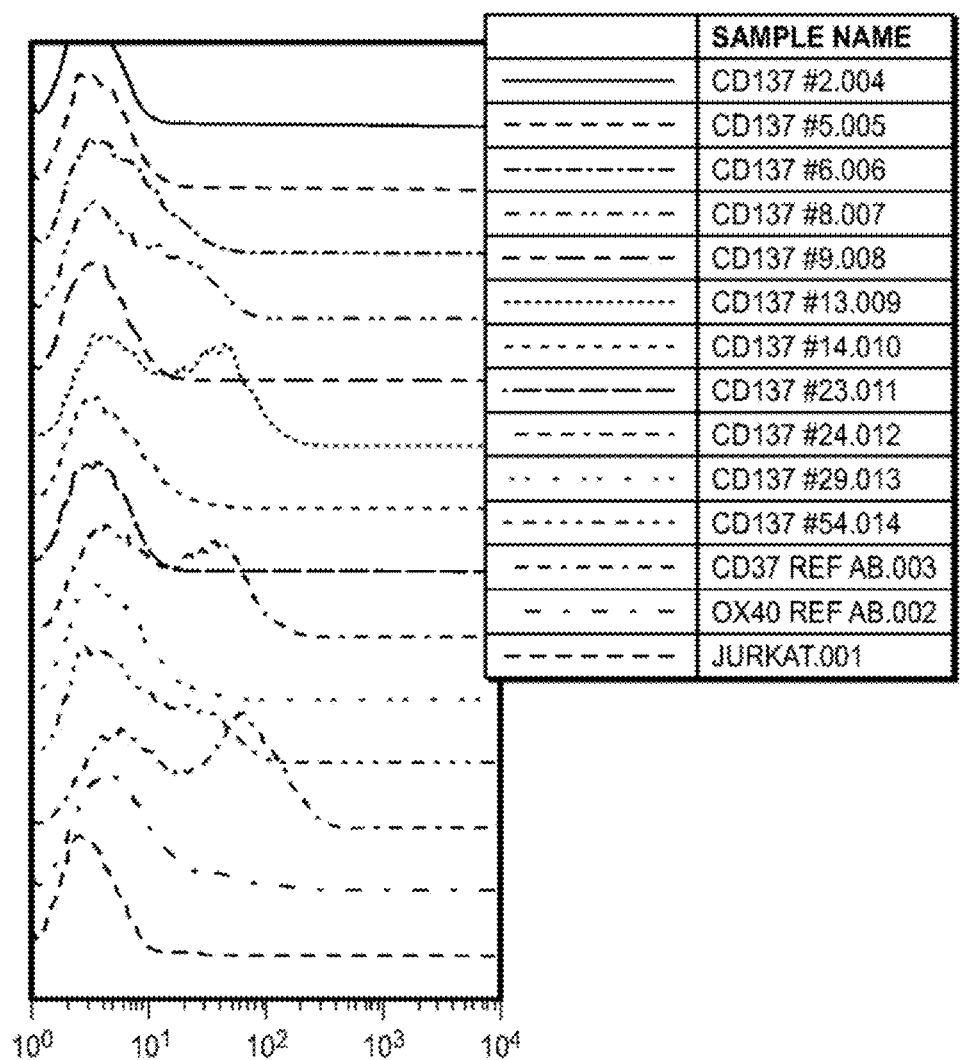
FIG. 4 shows the binding of anti-CD137 antibody leads on activated Jurkat cells by flow cytometry.

Purified anti-CD137 antibody leads were also applied to CD137-induced Jurkat cells to determine binding activity by FACS. Jurkat cells were treated with PMA (10 ng/ml) and ionomycin (1 μg/ml) to induce CD137 expression for 2 days. Stimulated cells were incubated with anti-CD137 (0.5 μg/ml) and reference (ref) Ab (0.5 μg/ml) as positive control for 1 hr on ice, left unstained or incubated with OX40 reference (ref) Ab as negative controls. The cells were washed three times with 1×PBS and then incubated with Alexa-488-conjugated goat anti-human IgG (H+L) (Invitrogen Inc.) on ice for an additional 1 hr. After staining, the cells were washed three times with 1×PBS, resuspended in 1×PBS before being analyzed by FACS Calibur (BD Biosciences, Inc.) and FlowJo (TreeStar, LLC). Among CD137 antibody leads, several leads possessed binding activity comparable to the reference antibody, as shown in FIG. 4.

These results show binding of anti-CD137 antibody leads to activation of Jurkat cells, as seen by flow cytometry.

Example 4

This example illustrates determination of anti-CD137 antibody binding activity by ELISA.

To perform a direct ligand binding assay of anti-CD137 antibody binding to CD137, recombinant CD137/Fc (100 ng/ml) was used to prepare pre-coated wells. Briefly, purified human CD137-IgG4 Fe (APBio) was dialyzed in Phosphate Buffered Saline (PBS), adjusted to 1 mg/ml and then diluted with PBS to a final concentration of 1 g/ml. Nunc-Immuno Maxisorp 96 well plates were pre-coated with 0.1 ml per well of recombinant CD137 protein, leaving empty wells for nonspecific binding controls, and incubated at 4° C. overnight. The CD137 recombinant protein solution was removed and the plates were washed three times with 0.4 ml of wash buffer (0.1% Tween-20 in PBS). 0.4 ml blocking buffer (5% low-fat milk powder in PBS) was added to all wells and incubated at room temperature for 1 hour. The blocking buffer was removed and washed three times with 0.4 ml wash buffer.

Figure 5:
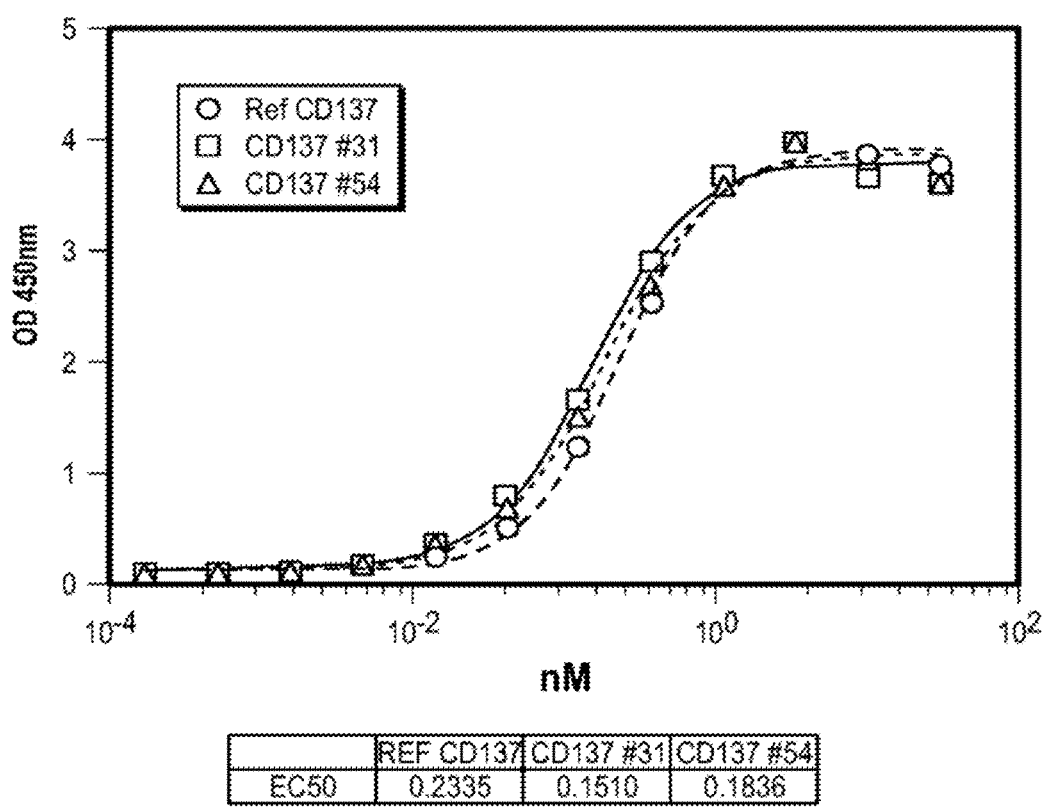
FIG. 5 shows the binding activity ($EC_{50}$) of anti-CD137 antibody leads to recombinant human CD137 by ELISA.

Pre-coated wells were incubated with serial dilutions of purified anti-CD137 antibodies. Serial dilutions of the CD137 antibodies were prepared in PBS and 0.1 ml added into each well. Plates were incubated for 1 hour at room temperature. The antibody solution was removed and the plates were washed three times with 0.4 ml wash buffer. HRP-conjugated goat anti-human IgG, F(ab')2 specific F(ab')2 antibody (Jackson Immunoresearch #109-036-097) was diluted 1:2000 with PBS and added at 0.1 ml per well. The plates were incubated for 1 hour at room temperature and washed three times with 0.4 ml wash buffer per well. Plates were developed with 0.1 ml TMB reagent (Invitrogen) and incubated for 1 to 5 minutes at room temperature. 0.05 ml 1N HCl was added to stop the reaction and absorbances were read at 450 nm on a Bio-Tek Spectra. OD450 readings were plotted against anti-CD137 concentrations, and 50% effective concentration ($EC_{50}$) values of anti-CD137 antibody binding to CD137/Fc were calculated. $EC_{50}$ values were calculated using GraphPad Prism (GraphPad Software, San Diego, CA). Calculated $EC_{50}$ values for anti-CD137 antibody clone 31 and clone 54 showed comparable binding activity to the reference antibody. Calculated $EC_{50}$ values for anti-CD137 specific antibody leads showed good binding activity compared to reference antibody (FIG. 5).

Anti-PD-L1 antibodies were detected with HRP-conjugated anti-human IgG1 Fab antibody before color development, with OD450 reading plotted against anti-PD-L1 concentrations.

Example 5

This example illustrates evaluation of protein aggregation of highly concentrated anti-CD137 antibody leads by SEC-HPLC.

Figure 6:
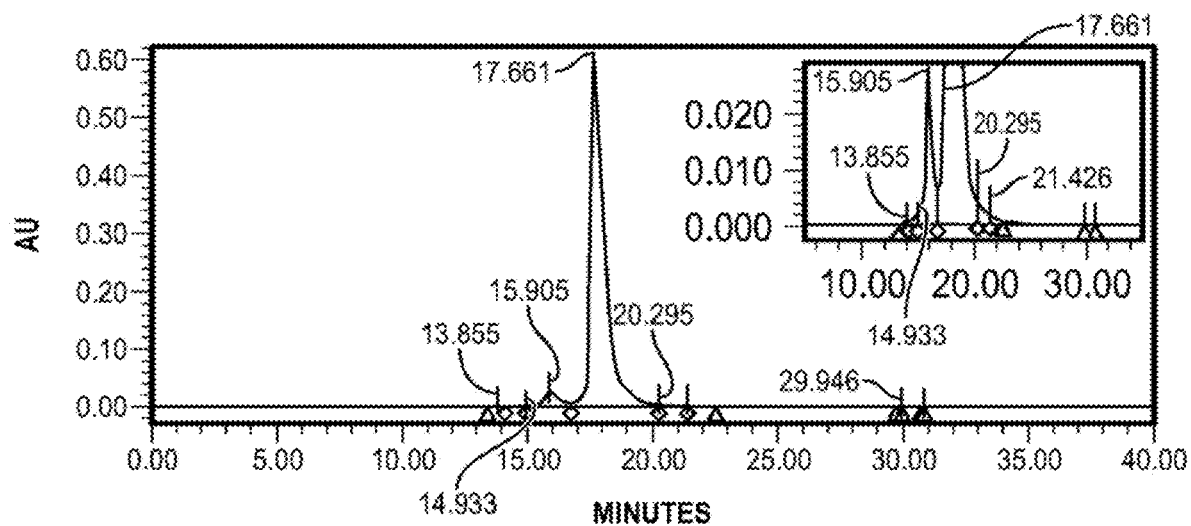
FIG. 6 shows protein aggregation of highly-concentrated anti-CD137 antibody clone 31 and clone 54 by SEC-HPLC.
Figure 6:
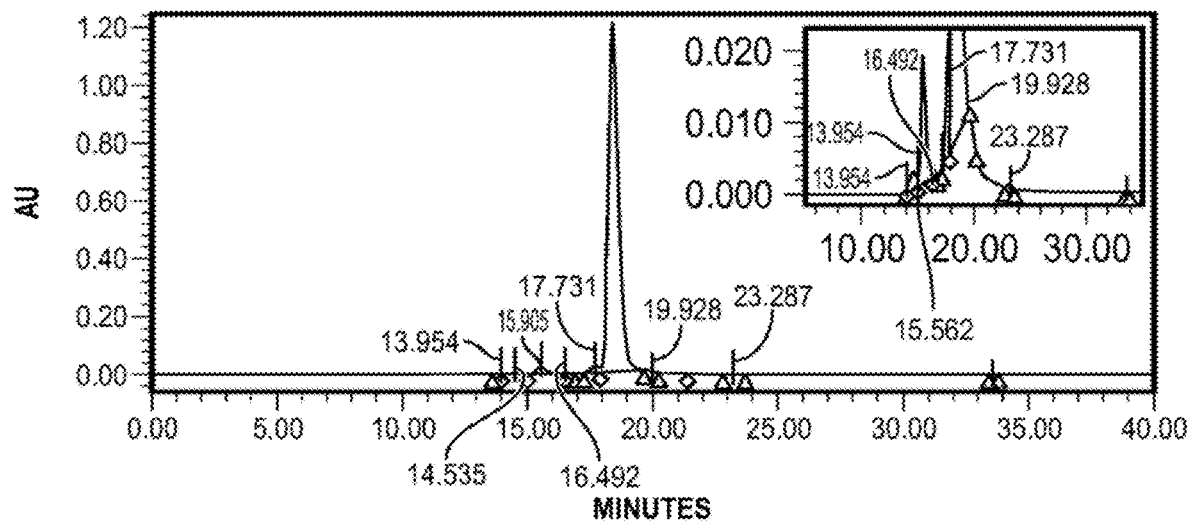

SEC-HPLC was performed using a Waters Alliance Separation Module 2695 with a Waters 2996 Photodiode Array detector. Samples were loaded onto a XBridge Protein BEH SEC Column (Waters, Cat #176007640) with isocratic 25 mM sodium phosphate, 200 mM NaCl, pH 6.8 as mobile phase buffer for SEC separation. The flow rate was 0.4 mL/min and the sample injection volume was 10 μL. Peaks were detected by absorbance at 280 nm. Before injection onto the SEC column, all samples were filtered with a 0.22 μm filter (Millipore, Cat #SLGP003RB) to remove any precipitated protein material. Data were analyzed by Empower 2 software. The main peak percentages of the highly concentrated-anti-CD137 antibody clone 31 and clone 54 were greater than 90%, as shown in the FIG. 6, with no obvious protein aggregates.

These results show that a high concentration anti-CD137 antibodies does not result in the formation of aggregates.

Example 6

This example illustrates agonistic activity of anti-CD137 antibodies.

Figure 7:
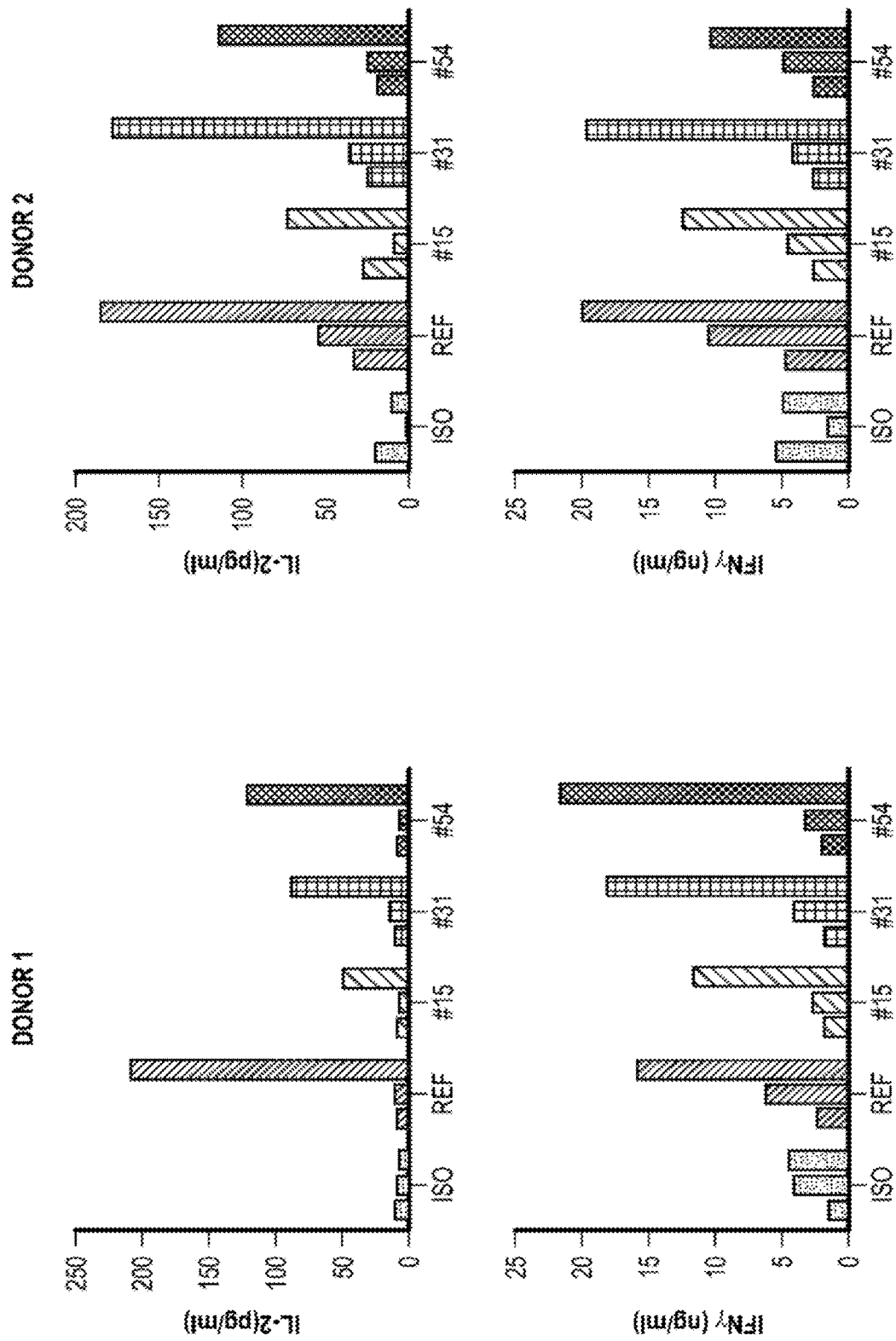
FIG. 7 shows cytokine production of T cells in the presence of the agonistic activity of anti-CD137 antibody leads.
Figure 7:
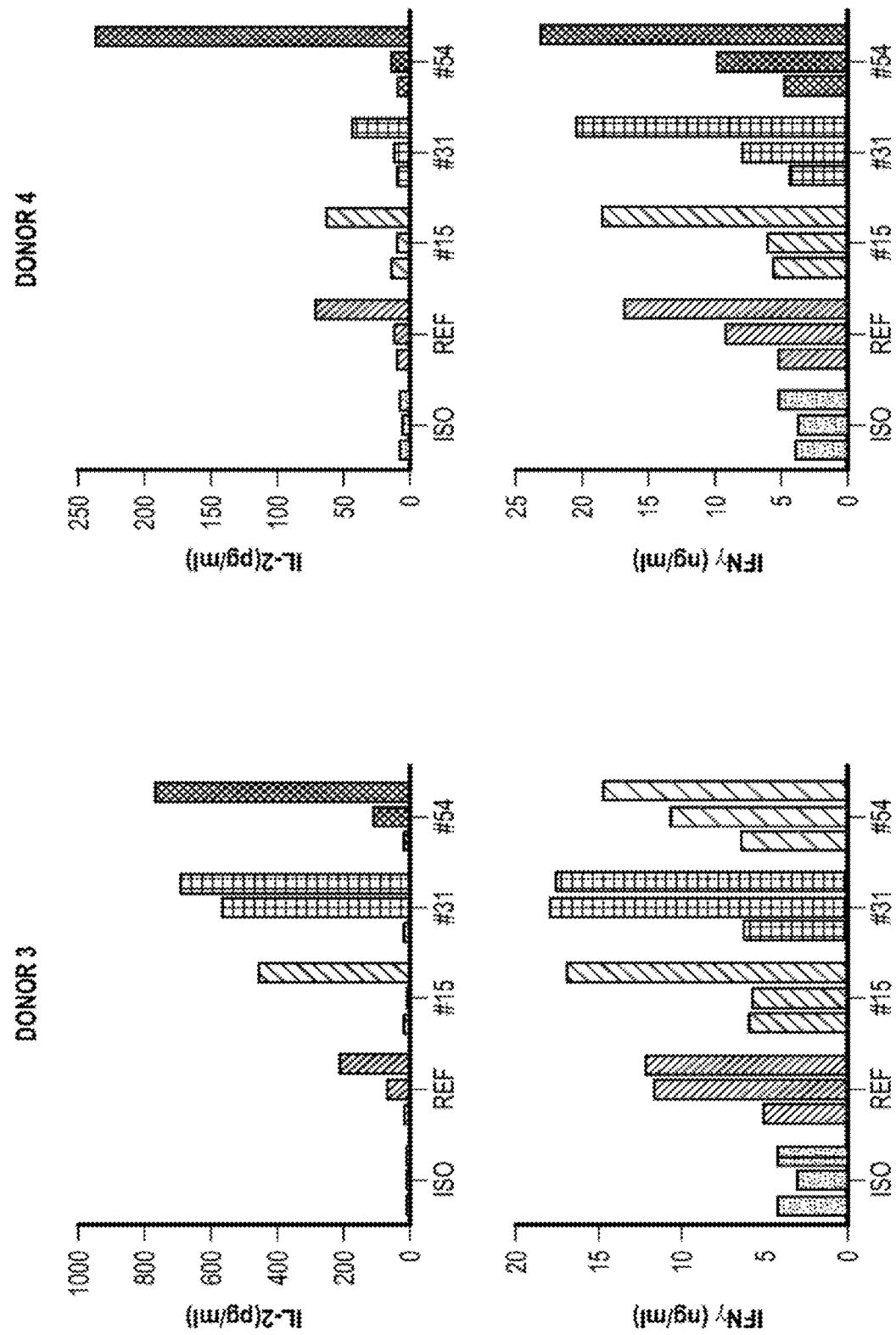
Figure 8:
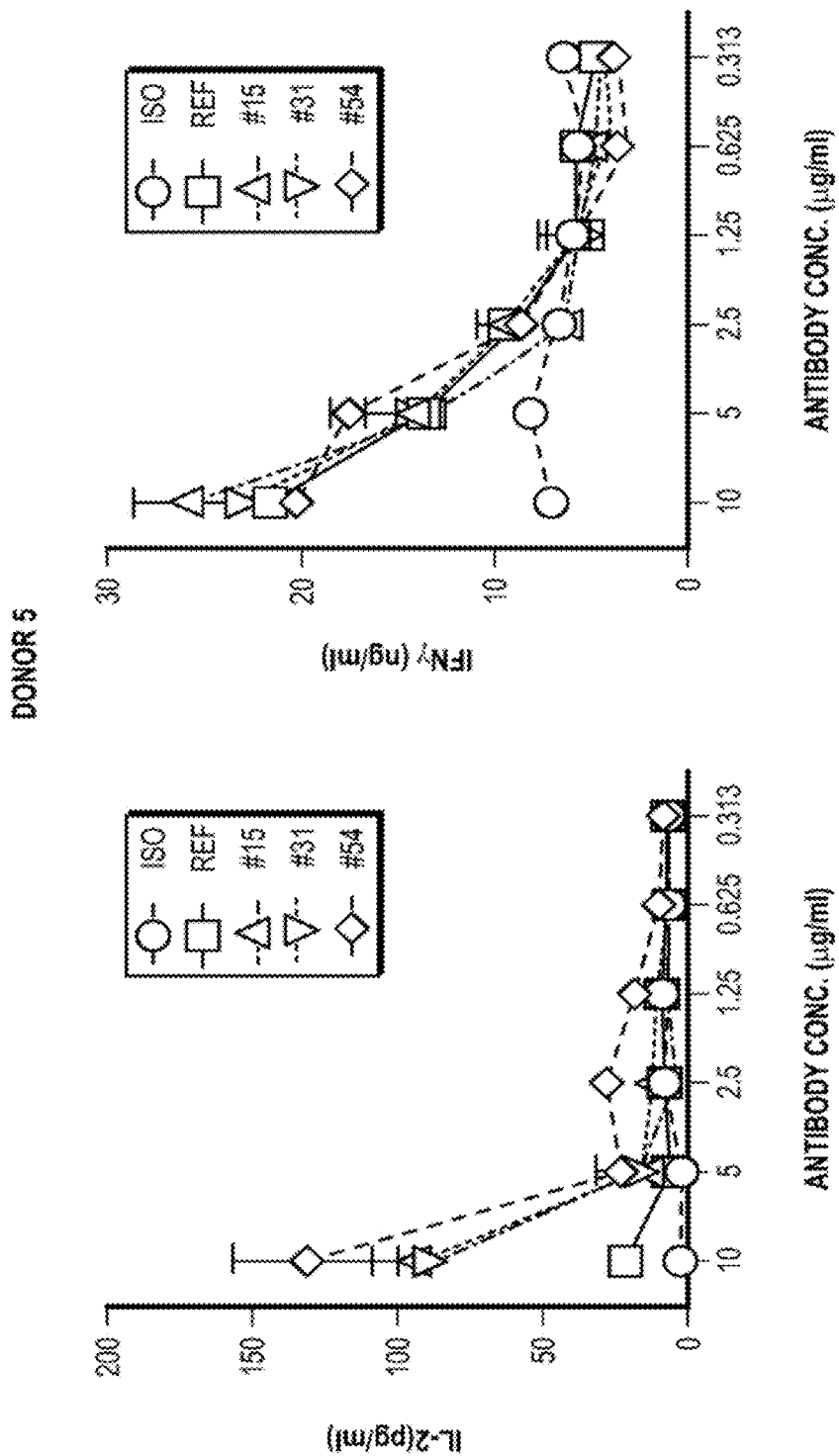
FIG. 8 shows dose-dependent induction of human T cell cytokine production by anti-CD137 antibody lead clones in primary human T cells.
Figure 8:
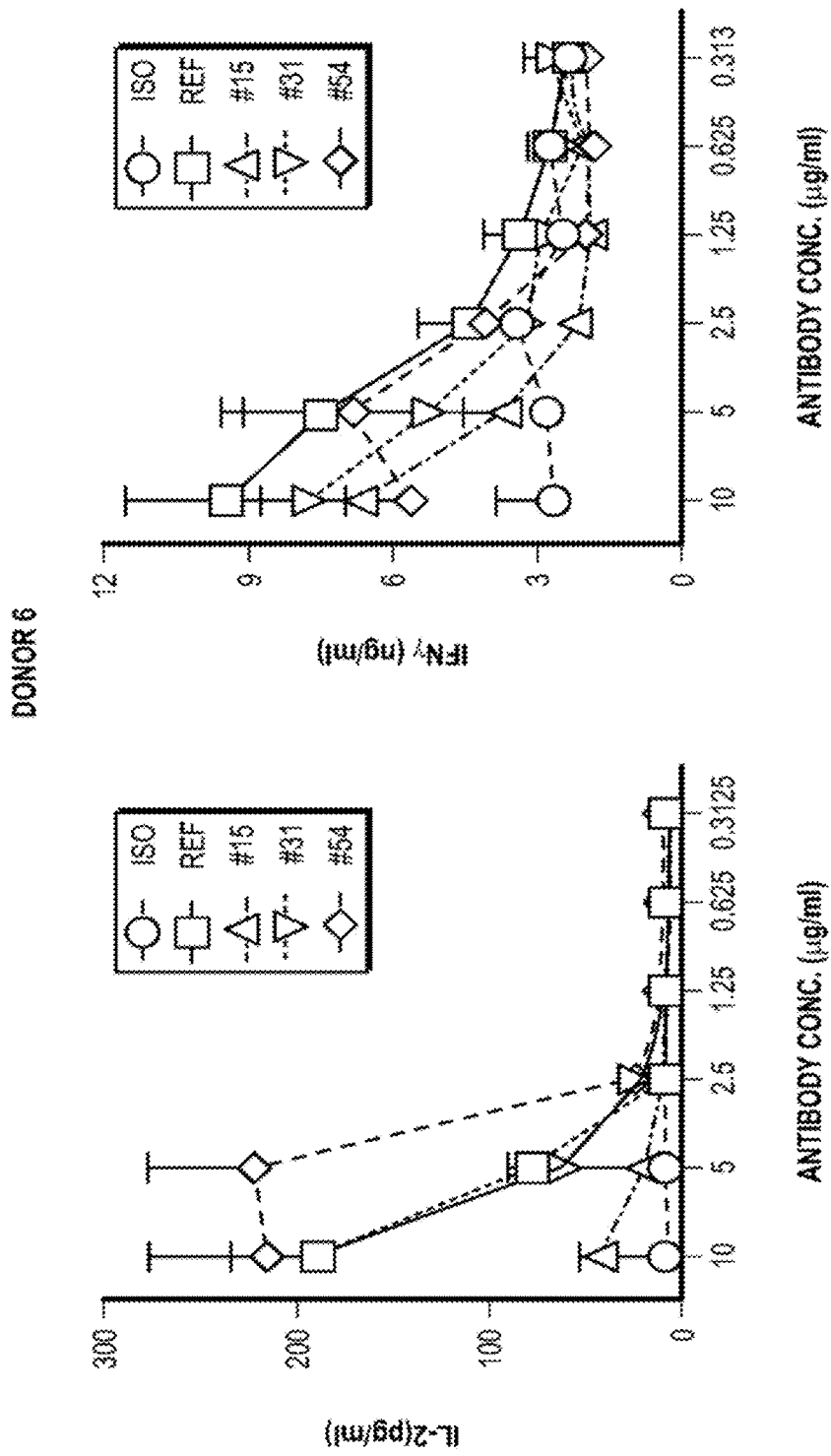

Purified antibody leads were functionally screened for their ability to enhance activation of human CD3+ cells, as seen by enhanced cytokine production, proliferation, and induction of proliferation of human CD3+ T cells. Anti-CD3 antibody (1 μg/ml, OKT3, BioLegend Cat. No. 317304), anti-CD137 antibody leads or isotype antibody (1, 3, and 10 μg/ml) were coated on a Maxisorp 96-well plate. Human CD3+ T-cells were isolated from peripheral blood of heathy adult volunteers using the RosetteSep™ Human T Cell Enrichment Cocktail (STEMCELL Cat. No. 15061). Isolated CD3+ T cells were labeled with CFSE (CellTrace™ CFSE cell proliferation kit, Life Technologies, Cat. No. C34554) and seeded in pre-coated wells (1×10 {circumflex over ( )}5 cells per well) with RPMI1640 medium (containing 10% fetal bovine serum, 2.5 mM L-glutamine, 1×Penicillin/Streptomycin). Three days later, cell proliferation was analyzed by flow cytometry and cytokine production of IL-2 and IFN-γ were analyzed by ELISA. As shown in FIG. 7 and FIG. 8, anti-CD137 antibody leads #15, #31, and #54, showed agonistic activity to enhance the CD3+ T cell activation in a dosage- and donor-dependent manner for at least two of four donors tested. Anti-CD137 clones #31 and #54 showed comparable or higher agonistic activity as seen by enhanced T cell activation as compared to reference antibody (Utomilumab; Chin et al., 2018; antibody sequence at kegg.jp/dbget-bin/www_bget?dr: D10997; see also U.S. Pat. No. 8,337,850). Therefore, clones #31 and #54 were chosen for bispecific antibody construction, as described below.

Example 7

This example illustrates combination treatment with anti-PD-L1 and anti-CD137 antibody in a mixed lymphocyte reaction.

Figure 9:
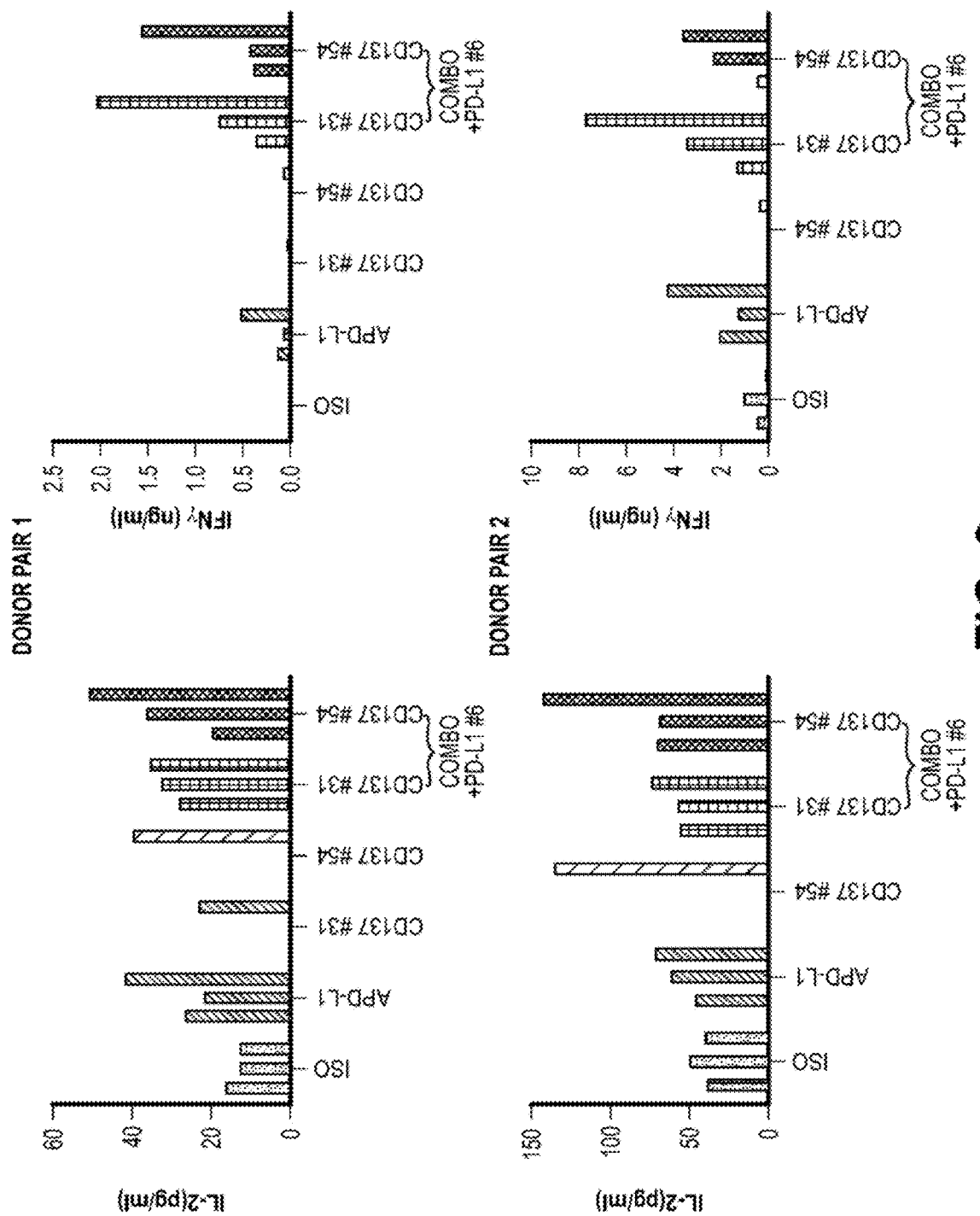
FIG. 9 shows that the combined treatment with anti-CD137 antibody boosts anti-PD-L1 antibody-mediated IFN-γ production by T cells in the mixed lymphocyte reaction.

Monocytes were isolated from peripheral blood of healthy donors by RosetteSep™ Human Monocyte Enrichment Cocktail (Cat. No. 15068) and cultured in RPMI1640 differentiation medium containing human GM-CSF and IL-4 (1000 U/ml each, R&D) for 6 days. Dendritic cell (DC) differentiation was verified by expression of DC-SIGN, CD14, CD80 or CD83 using flow cytometry. Differentiated DC were used as antigen-presenting cells (APCs) in mixed lymphocyte reactions (MLRs). Allogenic CD4+ T cells were isolated from human peripheral blood using RosetteSep™ Human CD4+ T Cell Enrichment Cocktail (Cat. No. 15062). The purity of CD4+ T cells was about 95% based on CD3 and CD4 expression. CFSE-labeled CD4+ T cells were co-cultured with DCs in the presence of antibody leads (0.4, 2, and 10 μg/ml) for 3 and 5 days. CD4+ T cell proliferation was analyzed by flow cytometry and cytokine production of IL-2 and IFN-γ in the culture medium was detected by ELISA. IL-2 and IFN-γ production increased significantly in the presence of anti-PD-L1 antibody in MLRs as compared to isotype control antibody. Interestingly, anti-CD137 antibody, such as clone #31, for example, further boosted anti-PD-L1 antibody-mediated IFN-γ production in MLRs with two distinct donor pairs, as shown in FIG. 9.

Example 8

This example illustrates the effects of anti-CD137 antibodies on CD137-CD137L interaction.

Figure 10:
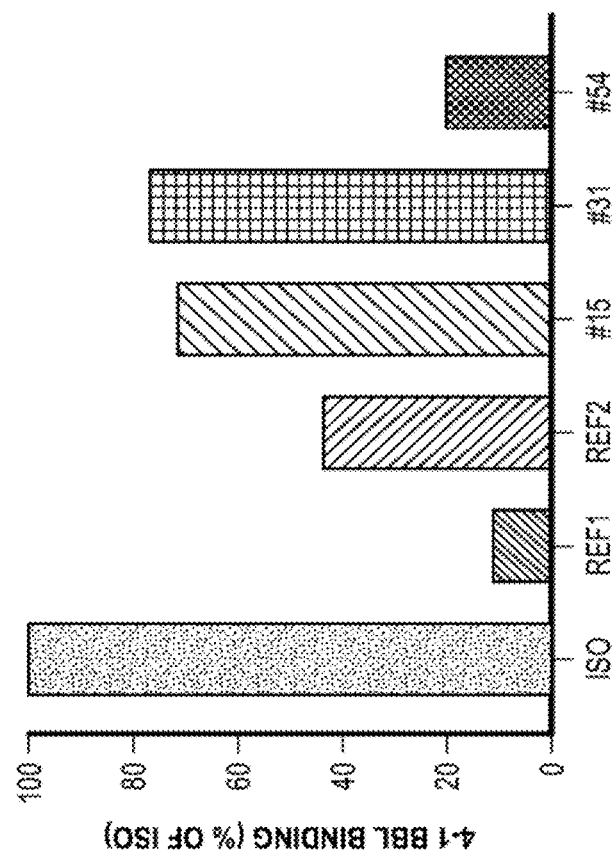
FIG. 10 shows distinct effects of anti-CD137 antibody clones on CD137-CD137L interaction.
Figure 10:
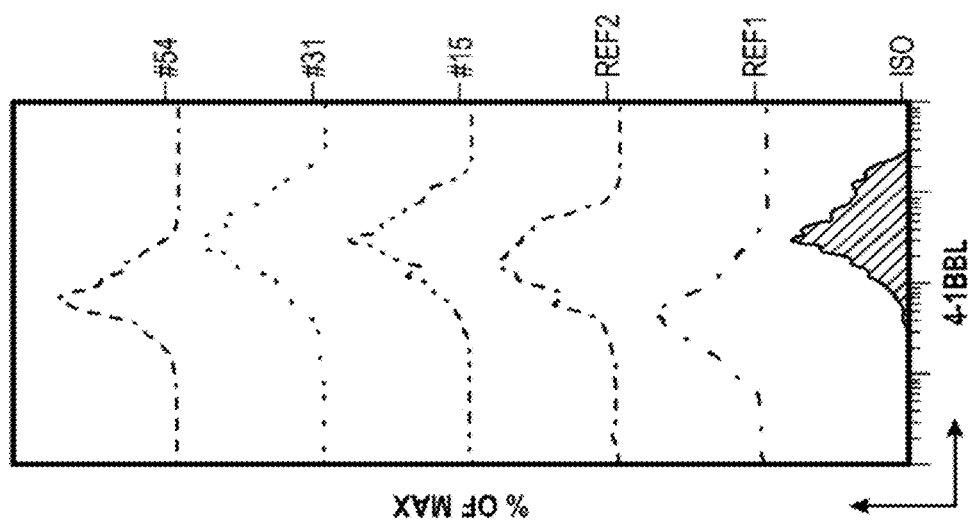

HEK-293F/CD137 cells were incubated with isotype control and anti-CD137 antibodies (50 μg/ml) for 30 mins on ice, washed twice with PBS/2% FBS (PBS2), and incubated with His-tagged 4-1BBL (0.5 μg/ml, Acro BIOSYSTEMS) for 20 mins on ice. After washing twice with PBS2, the presence of anti-CD137 antibody and 4-1BBL on HEK-293F/CD137 cells was detected using anti-human Fc-A488 (Jackson ImmunoResearch) and anti-His antibody-APC (Biolegend), respectively, followed by analysis using a Calibur flow cytometer (BD). Except for incubation with isotype control, almost all cells were A488-positive. Mean fluorescence intensity (MFI) of the APC channel was calculated using FlowJo (TreeStar, LLC) and values shown as a histogram (FIG. 10). As shown in FIG. 10, the reference antibody 1 (ref1) and clone #54 efficiently blocked CD137-CD137L interaction, while the reference antibody 2 (ref2), clone #15, and clone #31 were less efficient or inefficient at blocking CD137-CD137L interaction.

Example 9

This example illustrates pharmacokinetics of anti-CD137 antibody leads in vivo.

Figure 11:
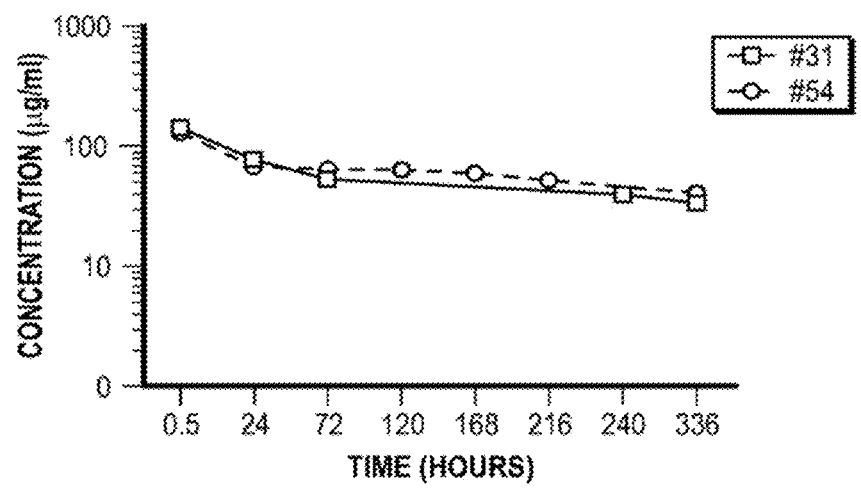
FIG. 11 shows the pharmacokinetic profiles of anti-CD137 antibody clone #31 and #54 in vivo.

Antibodies were administrated at a dose of 5 mg per kg body weight by intravenous bolus injection into SCID-beige mice. Peripheral blood was collected at the indicated time points post injection. Antibody plasma concentrations were detected by ELISA as described below. CD137-human Fc (1 μg/mL) pre-coated wells were incubated with titrated concentrations of purified anti-CD137 IgG4 antibody to prepare a standard curve to calculate antibody concentrations in the plasma (using fresh preparations in blocking solution). Samples collected at different time points were also applied to pre-coated CD137-human Fc wells for detection. After washing with 0.1% Tween-20 in PBS, bound antibodies were detected using HRP-conjugated anti-human Fab antibody (0.4 μg/mL) before color development. Antibody plasma concentrations were calculated by the interpolation method. PK parameters were calculated using PKSolver software (Zhang, Huo, Zhou, & Xie, 2010). Antibodies showed a good $t_{1/2}$ of about 176 hours and an AUC of about 7800 ug/ml*h (FIG. 11).

Example 10

This example illustrates crosslinking-dependent agonistic activity of anti-CD137 antibody leads.

Figure 12:
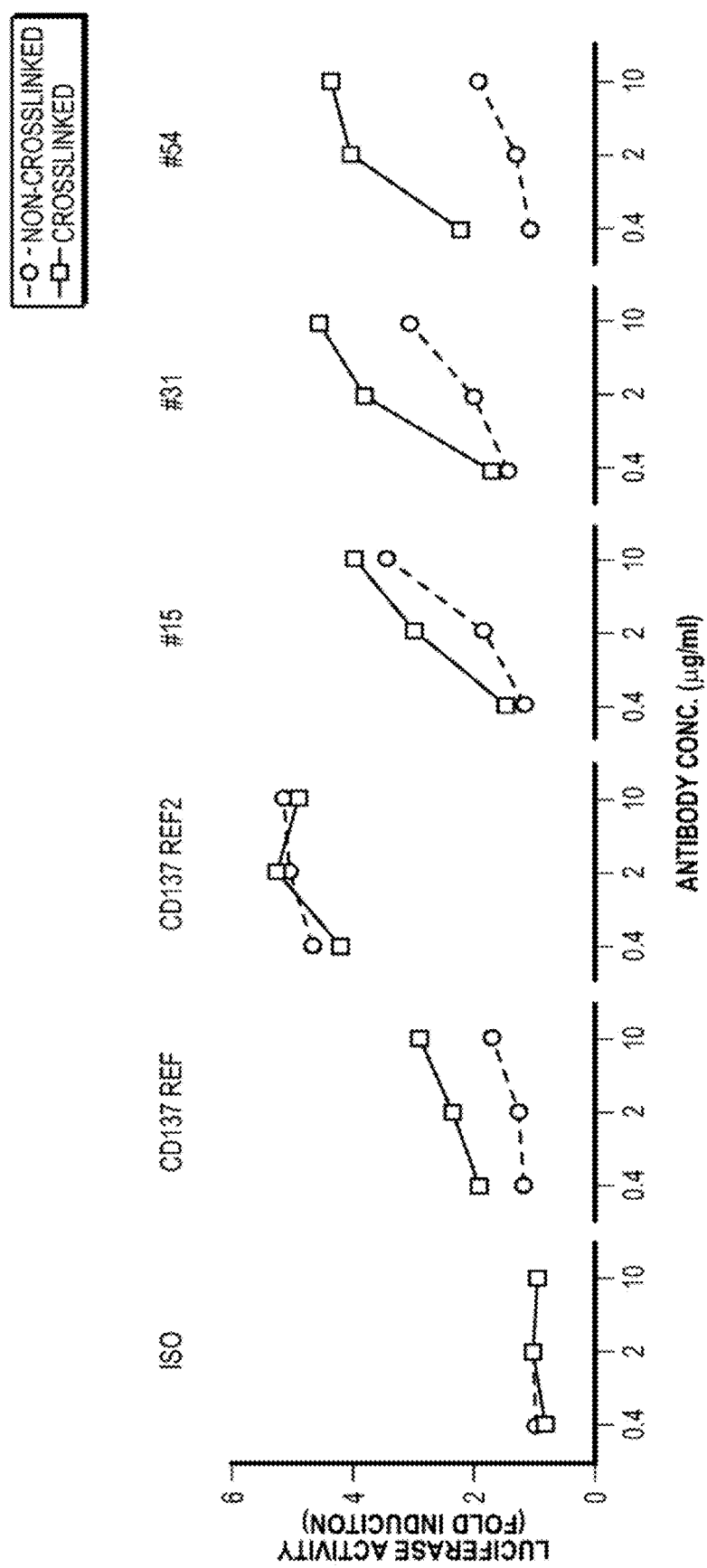
FIG. 12 shows different requirements of crosslinking for agonistic activity of anti-CD137 antibody clones compared to Utomilumab (CD137 ref) and Urelumab (CD137 ref 2).
Figure 13:
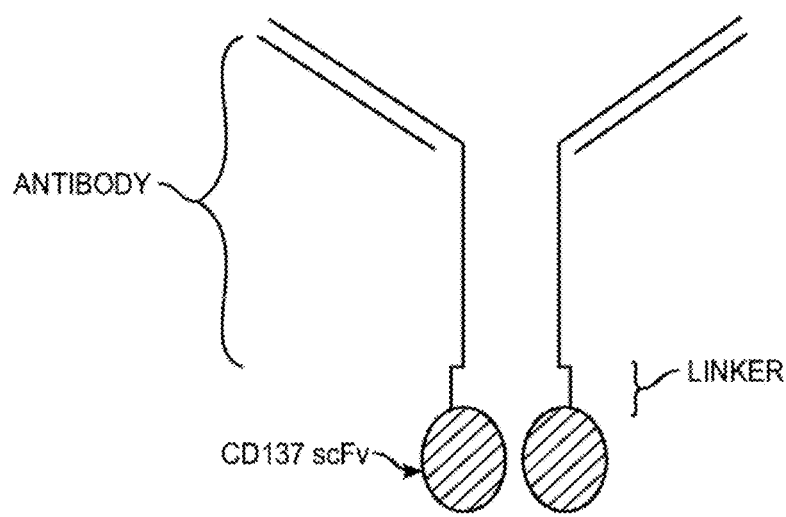
FIG. 13 shows the symmetric format of an anti-PD-L1-CD137 bispecific antibody (bsAb).

Stable clones of CD137 reporter cells were generated by transfecting HEK293 cells with NF-κB-driven luciferase and full-length CD137, followed by selection with hygromycin and G418, respectively. For agonistic activity assays, anti-CD137 antibodies (10, 2, and 0.4 µg/ml) alone or crosslinked with goat anti-human IgG (5 µg/ml, Jackson ImmunoResearch, Catalog No. 109-006-008) were added to the reporter cells and incubated for 5 hours. Luciferase activity was detected using the ONE-Glo™ Luciferase Assay System (Promega, Cat. No. E6120). Consistent with previous reports, Utomilumab (CD137 ref, FIG. 12) showed crosslinking-dependent agonist activity, while Urelumab (CD137 ref2, FIG. 12) showed crosslinking-independent agonist activity that may cause the severe hepatotoxicity observed in clinical trials. Compared to Utomilumab, CD137 #54 showed greater agonistic activity upon crosslinking while agonist activity in the absence of crosslinking was moderate and similar to agonistic activity of Utomilumab (FIG. 12). Without being limited by theory, this characteristic of CD137 #54 may induce target-dependent T-cell activation when included in bispecific antibodies with tumor-specific binders.

In summary, these results show different cross-linking dependencies of anti-CD137 #15, anti-CD137 #31, anti-CD137 #54 agonist activity.

Example 11

This example illustrates construction, expression, and purification of anti-PD-L1-CD137 bispecific antibodies.

Anti-PD-L1 antibody clone 6 was used in IgG form without ADCC, and anti-CD137 antibody was used in scFv format and fused to the C-terminus of the anti-PD-L1 clone 6 antibody Fc region. Bispecific antibody constructs that include an anti-PD-L1 antibody Fc region fused with CD137 scFv are shown in Table 1 below (Sequences), with a schematic shown in FIG. 10. A short flexible peptide linker (GGGGS)2 (SEQ ID NO: 29) was placed between the anti-PD-L1 antibody heavy chain C-terminus of the Fc region (SEQ ID NO: 25 or SEQ ID NO:26) and the N-terminal module of the anti-CD137 scFv to ensure correct folding and minimize steric hindrance. The amino acid sequences of anti-PD-L1-CD137 scFv heavy chains are shown in SEQ ID NO:31 and SEQ ID NO:32. Antibody Fc fusion protein constructs were expressed using the Gibco ExpiCHO Expression System and purified from the cell culture supernatant of transfected cells via 1-step Protein G chromatography.

In addition to a bispecific anti-PD-L1 antibody Fc fused with anti-CD137 scFv described above, antibodies fused to anti-CD137 scFv can include anti-inhibitory immune checkpoint antibodies, such as anti-PD-1, anti-CTLA-4, anti-LAG3, and others, or immune stimulatory antibodies, such as anti-CD28, anti-CD40, anti-CD137, anti-CD27, anti-ICOS, and others. For each bispecific antibody, a linker can be placed between the antibody Fc domain and anti-CD137 scFv to generate the bispecific antibody.

Figure 14:
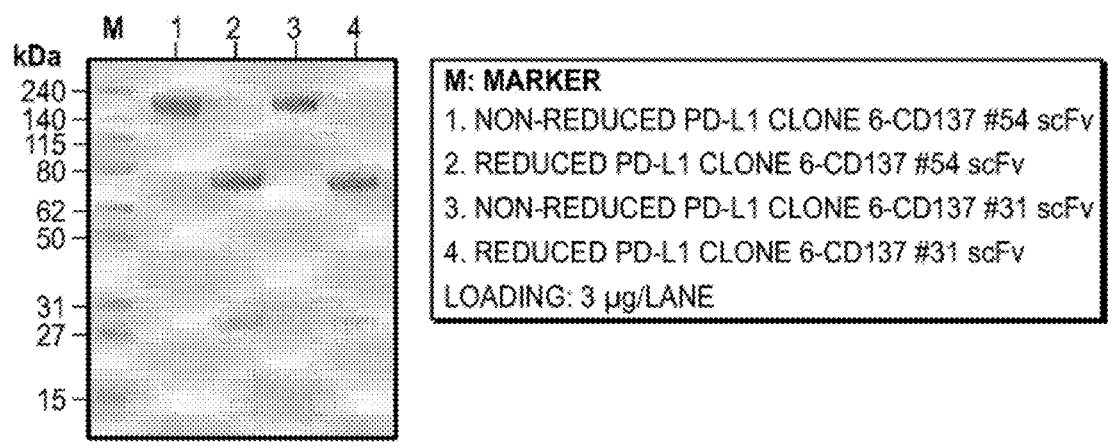
FIG. 14 shows the purity and integrity of protein G-purified anti-PD-L1-CD137 bsAbs by SDS-PAGE. More than 90% can be obtained by one step of Protein G chromatography.
Figure 15:
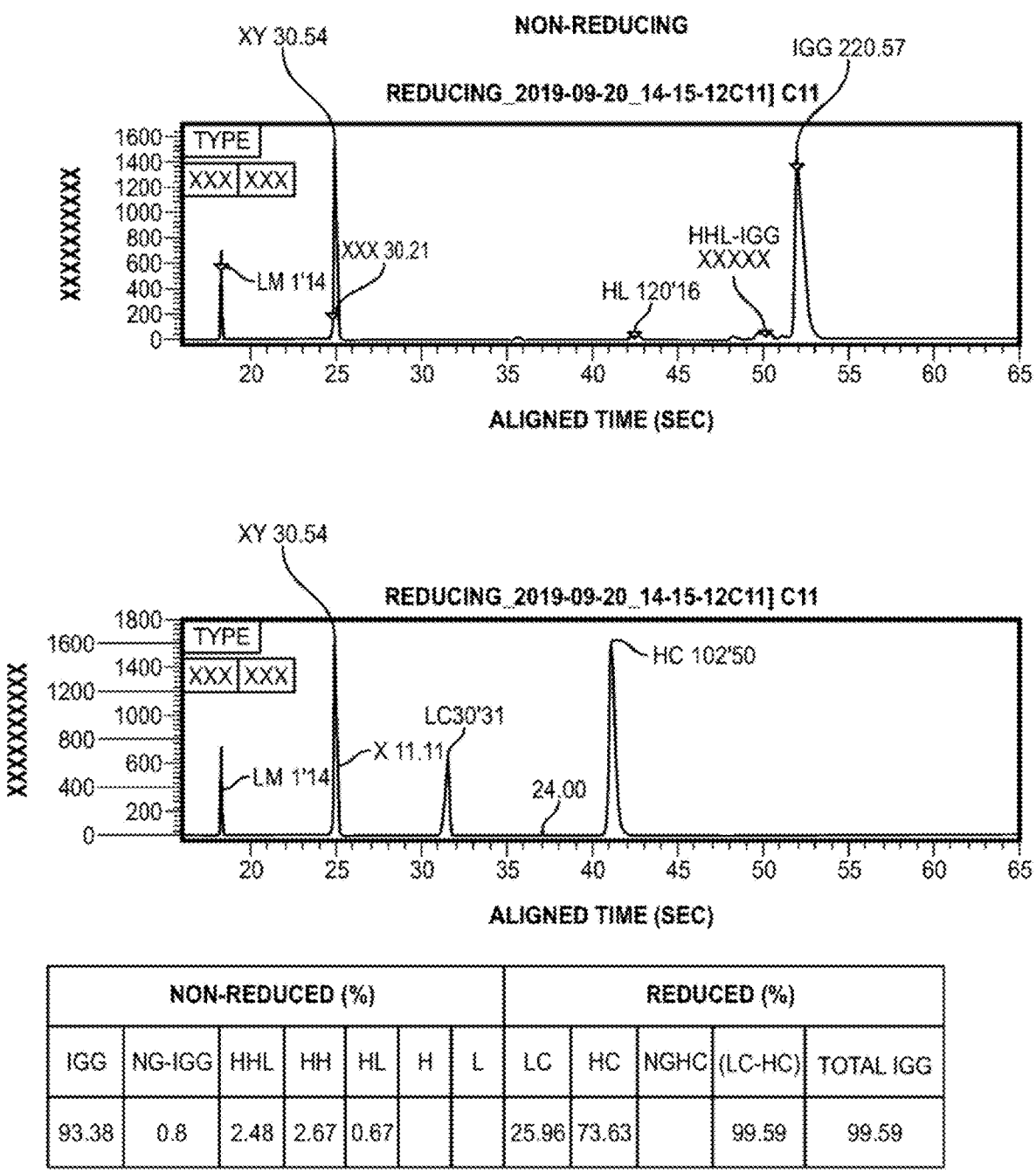
FIG. 15 shows the purity and integrity of protein A-purified anti-PD-L1-CD137 bsAbs by μCE-SDS.

The purity of bispecific antibodies was greater than 90% (FIG. 14 and FIG. 15). Purities greater than 90% were obtained in a single step purification process, consistent with purified fusion proteins having the correct molecular weight (Mw=220 kD). FIG. 14 shows a representative PAGE gel analysis of purified anti-PD-L1-CD137 bispecific antibodies (bsAbs). Culture supernatants from mammalian cells collected 4 days post-transfection were purified using Protein G chromatography (Thermo Fisher). The purified proteins were analyzed under reducing or non-reducing condition before loading on the gel (3 µg/lane). Results indicated that both proteins have molecular weights of about 220 kDa under non-reducing conditions, and heavy chain-CD137 scFv and light chain have molecular weights of ~85 kDa and ~25 kDa under reducing condition, respectively. FIG. 15 shows the purity and integrity of one-step Protein A-purified anti-PD-L1 #6-CD137 #54 bsAb by µCE-SDS.

Example 12

This example illustrates antigen recognition by anti-PD-L1-CD137 bispecific antibodies.

Binding activities of the anti-PD-L1-CD137 bispecific antibodies were determined by FortéBio® (Menlo Park, Calif) biosensor analysis. His-tagged CD137 (ACROBiosystems) was loaded on aHISIK (Anti-Penta-HIS) biosensor (Cat #18-5120) at 5 µg/mL in DPBS with 0.02% Tween-20 and 0.1% BSA for 5 minutes. Sensors were then exposed to the antibody as indicated at 100 nM using the same buffer for 5 minutes, followed by association with 100 nM of second antigen (PD-L1 fused to a mouse Fc domain) for another 5 minutes. The binding chart shown in FIG. 16 was then prepared using Octet Data Acquisition and Analysis Software as described by the manufacturer. Compared to control antibody, both bispecific antibodies (anti-PD-L1 #6-CD137 #31 and anti-PD-L1 #6-CD137 #54) could recognize first CD137 and then PD-L1 as well, demonstrating that bispecific antibodies could target PD-L1 and CD137 simultaneously.

In summary, these results show that anti-PD-L1-CD137 bispecific antibodies simultaneously recognize PD-L1 and CD137, as determined by FortéBio® biosensor analysis.

Example 13

This example illustrates enhancement of T cell activation by anti-PD-L1 antibody and anti-PD-L1-CD137 scFv bispecific antibody (bsAb) in an allogenic mixed lymphocyte reaction.

Figure 17:
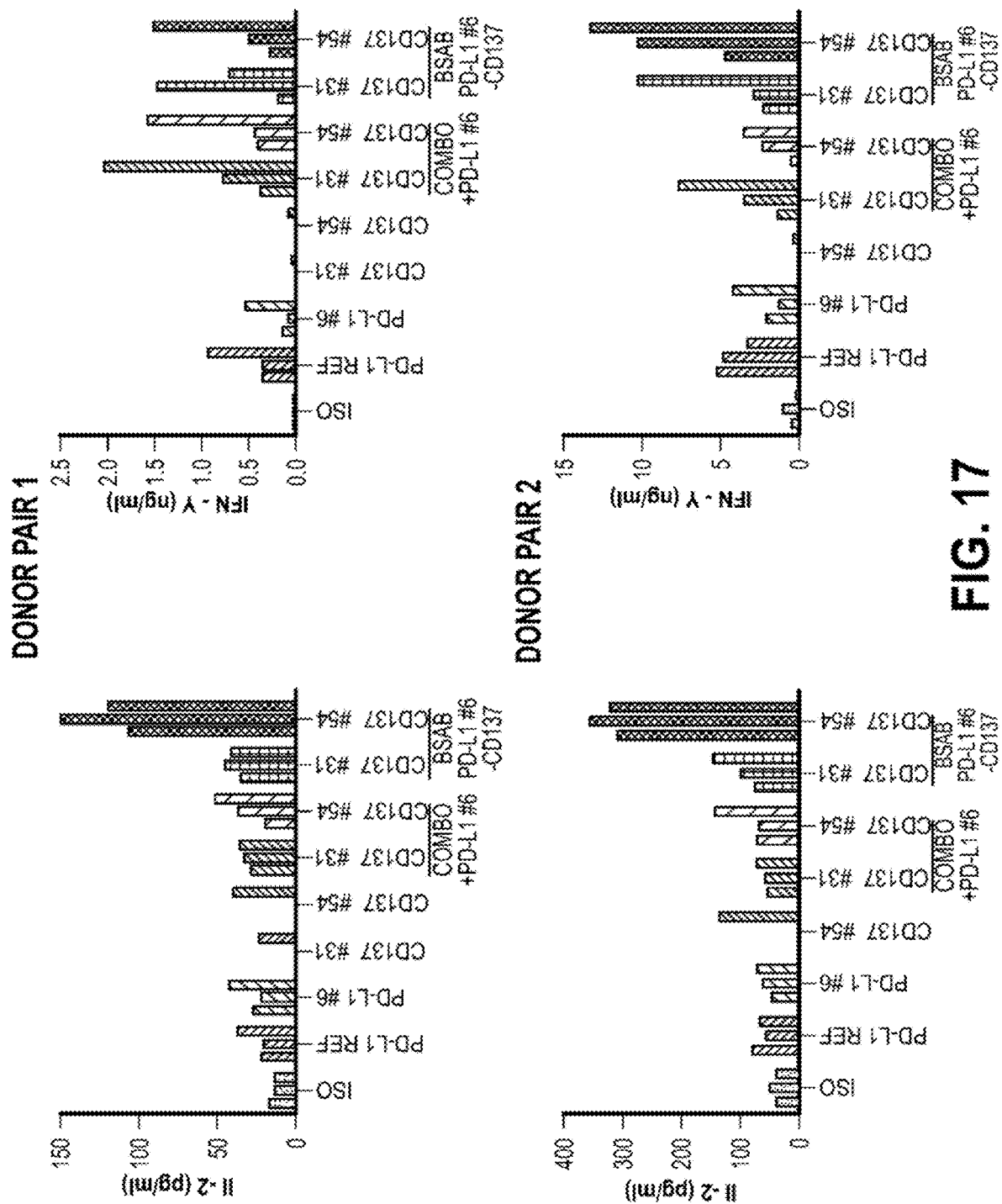
FIG. 17 shows that anti-PD-L1 #6-CD137 #54 bsAb induces synergistic T cell activation compared to monotreatment, combination treatment, or treatment with anti-PD-L1 #6-CD137 #31 bsAb in the mixed lymphocyte reaction.

Monocytes were isolated from peripheral blood of healthy donors by RosetteSep™ Human Monocyte Enrichment Cocktail (Cat. No. 15068) and cultured in RPMI1640 differentiation medium containing human GM-CSF and IL-4 (1000 U/ml each, R&D) for 6 days. Allogenic CD4+ T cells were isolated from human peripheral blood by RosetteSep™ Human CD4+ T Cell Enrichment Cocktail (Cat. No. 15062). The purity of CD4+ T cells was about 95% based on CD3 and CD4 expression. CFSE-labeled CD4+ T cells were co-cultured with DCs in the presence of antibody leads (1, 3, and 10 µg/ml) for 3 and 5 days. CD4+ T cell proliferation was analyzed by flow cytometry and cytokine production of IL-2 and IFN-γ in the culture medium was detected by ELISA. Compared to the mono-treatment and combination treatment with anti-PD-L1 and anti-CD137 antibodies, anti-PD-L1 #6-CD137 #54 strikingly enhanced activation of T cells (FIG. 17, showing results for two donor pairs).

These results show that anti-PD-L1 #6-CD137 #54 bsAb induced a more potent T-cell activation in mixed lymphocyte reactions compared to the mono-treatment or combination treatment with anti-PDL-1 and anti-CD137 antibodies and compared to treatment with anti-PD-L1 #6-CD137 #31 bsAb.

Example 14

This example illustrates boosting of antigen-specific T-cell activation by anti-PD-L1-CD137 scFv bispecific antibody leads.

Human memory CD4 and CD8 T cells were isolated using an EasySep™ Human Memory CD4+ T Cell Enrichment Kit (STEMCELL, Cat. No. 19157) and a Human CD8+ T Cell Isolation Kit (STEMCELL, Cat. No. 17953), respectively. Cocultures of memory CD4-T cells and autologous immature DCs were stimulated with a CEFX Ultra SuperStim Pool MHC-II subset (1 ug/ml, JPT) in the presence of antibodies (0.4, 2, and 10 µg/ml) for 7 days. For cocultures with CD8-T cells, TLR-DC generated as immature DCs were matured for 24 hours by adding IL-1 (10 ng/ml, PeproTech), TNF-α (10 ng/ml, PeproTech), IFN-γ (5000 IU/ml, PeproTech), PGE2 (250 ng/ml, Sigma), poly I:C (10 µg/ml, Sigma), and R848 (5 µg/ml, Sigma) to the differentiation medium. Cocultures of CD8 T cells and autologous TLR-DCs were stimulated with a CEFX Ultra SuperStim Pool (1 µg/ml, JPT) in the presence of antibodies (0.4, 2, and 10 µg/ml) for 7 days. Similar to results observed in the MLR of Example 12, anti-PD-L1 #6-CD137 #54 bsAb boosted recall responses of memory CD4 T cells (FIG. 18A) and CD8 T cells (FIG. 18B) compared to mono-treatment with anti-PD-L1 or anti-CD137 monoclonal antibody or combination treatment with anti-PD-L1 and anti-CD137 monoclonal antibodies (FIGS. 18A-18B).

In summary, results shown in FIGS. 17 (Example 13) and 18 (this Example) show that anti-PD-L1 #6-CD137 #54 bsAb strikingly enhanced T-cell activation that was more robust than T-cell activation seen upon treatment with anti-PD-L1 and anti-CD137 monoclonal antibodies either alone or in combination. Moreover, T-cell activation seen upon treatment with anti-PD-L1 #6-CD137 #54 bsAb was antigen-dependent, as seen in recall response assays with CD4 and CD8 T cells. Without being limited by theory, the greater potency of T-cell activation seen with anti-PD-L1 #6-CD137 #54 bsAb as compared to anti-PD-L1 #6-CD137 #31 bsAb indicates that the anti-CD137 #54 arm of the bispecific antibody may bind to a unique CD137 epitope without steric hindrance resulting from binding to PD-L1 by the anti-PD-L1 arm of the bispecific antibody.

Example 15

This example illustrates anti-PD-L1-CD137 bispecific antibody-induced target-dependent T-cell activation.

Figure 19:
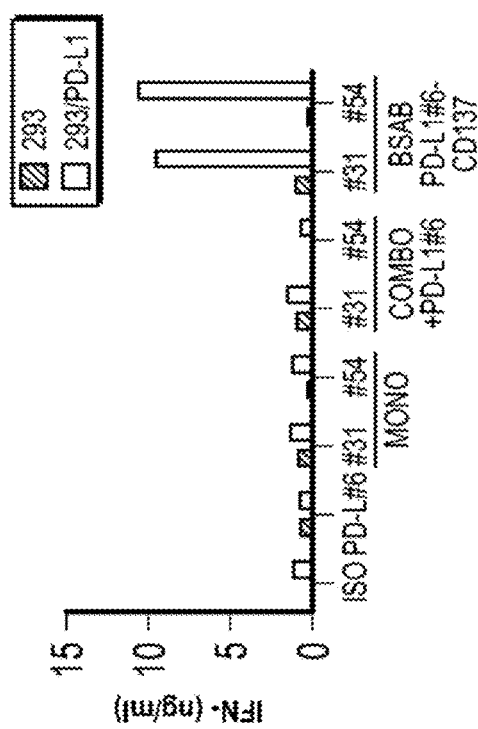
FIG. 19 shows that target-dependent T cell activation is induced by anti-PD-L1 #6-CD137 #31 or anti-PD-L1 #6-CD137 #54 bsAb while coculturing T cells with PD-L1-overexpressing HEK-293 cells.
Figure 19:
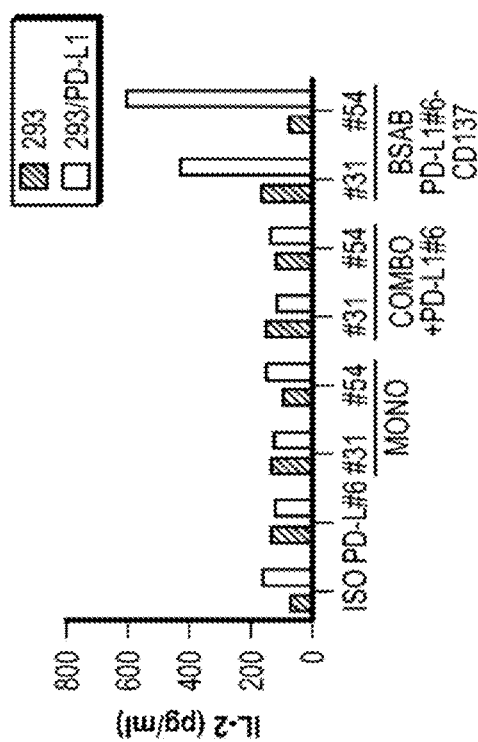

Human T cells were isolated using a RosetteSep™ Human T Cell Enrichment Cocktail (STEMCELL Cat. No. 15061). Purified T cells were activated by plate-bound anti-CD3 (OKT3, 1 µg/ml) and cocultured with PD-L1-overexpressing or parental HEK293 cells under the indicated antibody treatments (FIG. 19). Compared to mono-treatment or combination treatment with anti-PD-L1 and anti-CD137 monoclonal antibodies, anti-PD-L1-CD137 bispecific antibodies greatly boosted T cell activation upon coculture with PD-L1-overexpressing, but not the PD-L1-negative parental cells, as shown in FIG. 19.

In summary, these results show that target-dependent T-cell activation was only induced by anti-PD-L1 #6-CD137 bsAb when cocultured with PD-L1-overexpressing HEK-293 cells, but not parental HEK293 cells, in the presence plate-bound anti-CD3 (OKT3).

Example 16

This example illustrates tumor antigen-dependent T cell activation induced by anti-tumor antigen-specific CD137 #54 bispecific antibodies.

Human CD8-T cells were isolated by positive selection as described above (Example 15). Purified CD8-T cells were cocultured with PD-L1-positive tumor cells (NCI-H1975, PC-3, and MDA-MD-231) in the presence of anti-CD3 (OKT3)-coated polybeads at a 1:1 ratio. Three days later, T cell activation was assayed based on IFN-γ production as measured by ELISA, and tumor cell cytotoxicity was detected by CytoTox 96® Cytotoxicity Assay (Promega, Cat. #G1780).

Figure 20A:
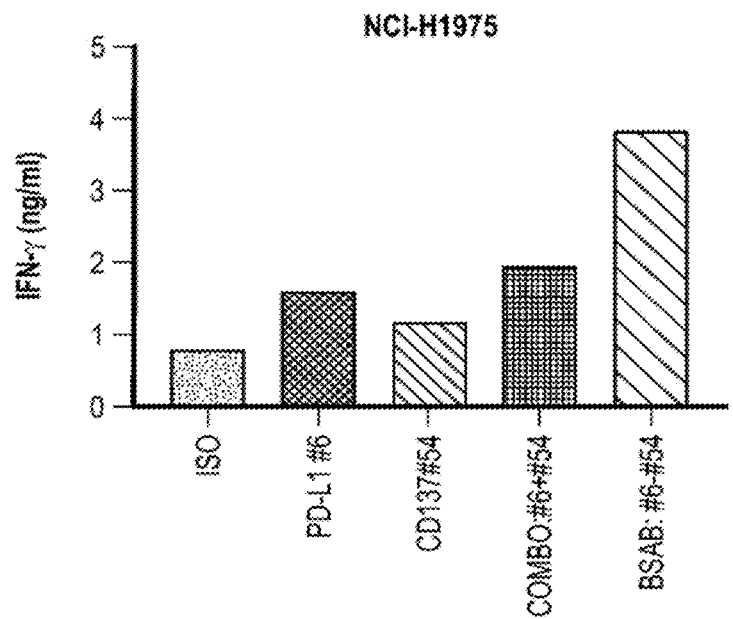
FIGS. 20A-20C show that anti-PD-L1 #6-CD137 #54 bsAb induces IFN-γ production (FIG. 20A, FIG. 20C and left panel of FIG. 20B) and cancer cell cytotoxicity (right panel of FIG. 20B) of T cells upon coculturing with PD-L1-positive cancer cells.
Figure 20B:
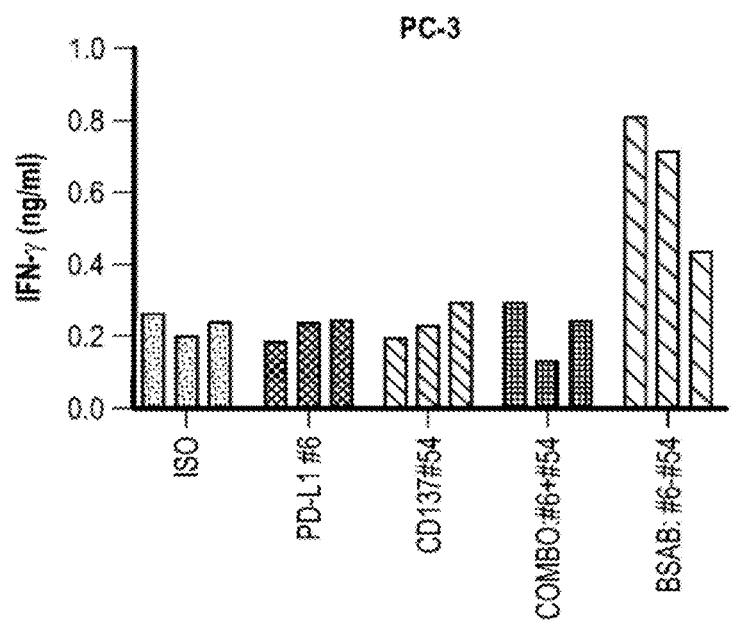
Figure 20B:
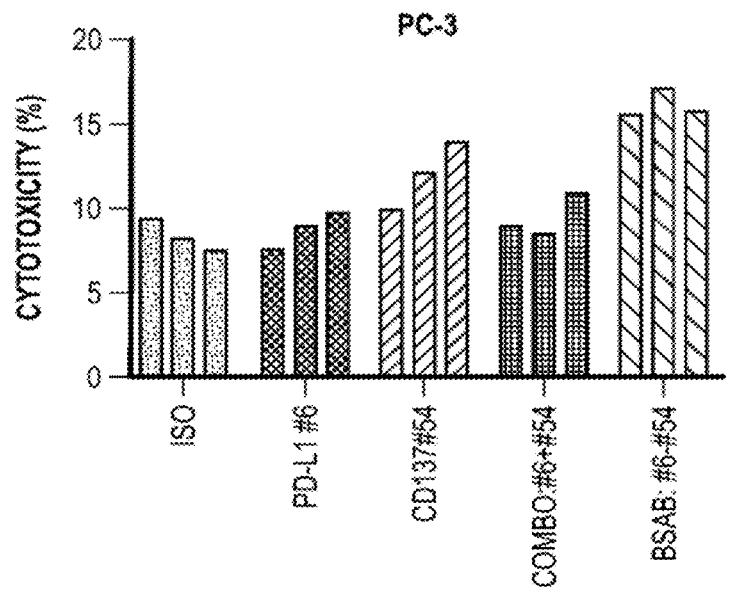
Figure 20C:
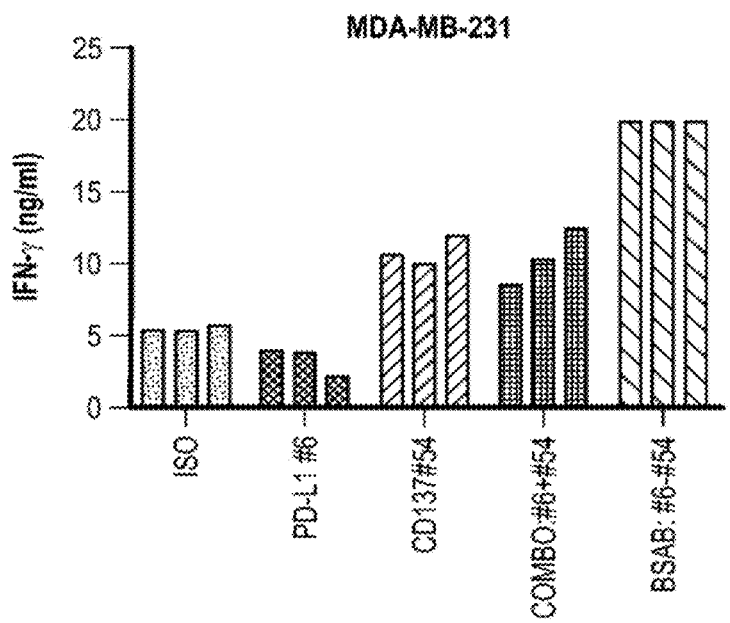
Figure 21B:
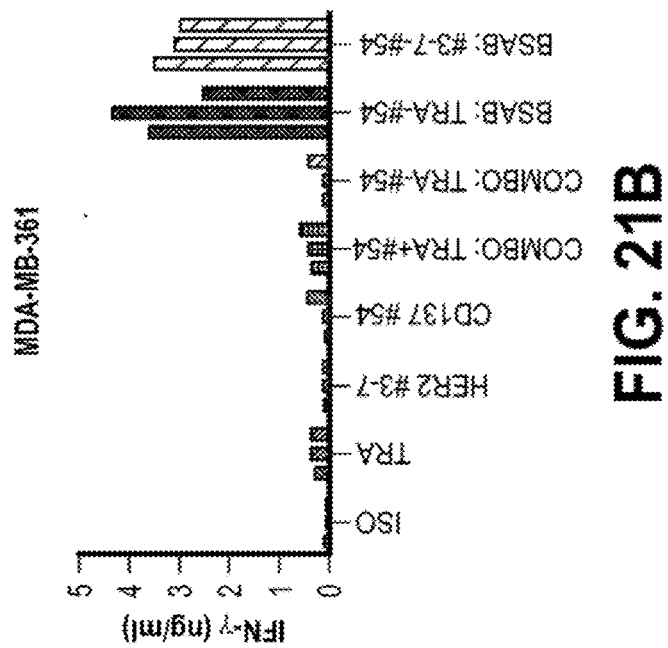
FIGS. 21A-21B show that Trastuzumab (Tra)-CD137 #54 or anti-Her2 #3-7-CD137 #54 bsAbs induce IFN-γ production of CD8 T cells upon coculturing with Her2-positive cancer cells.
Figure 21A:
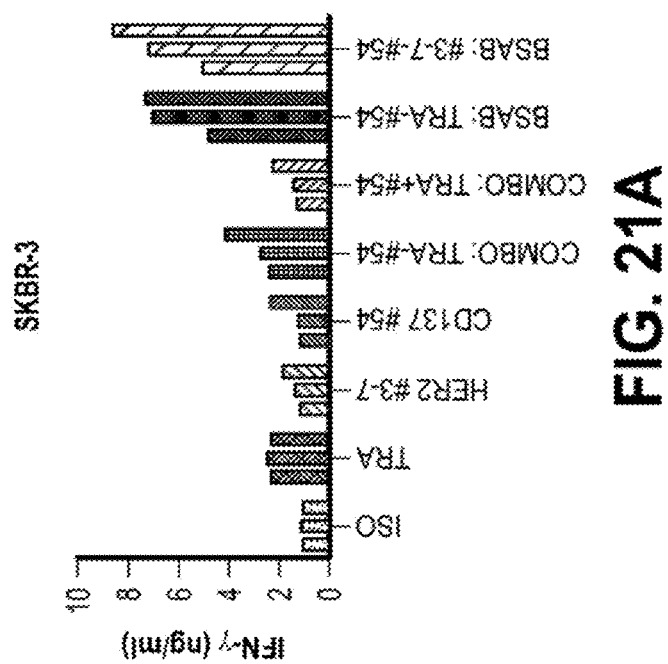
Figure 22A:
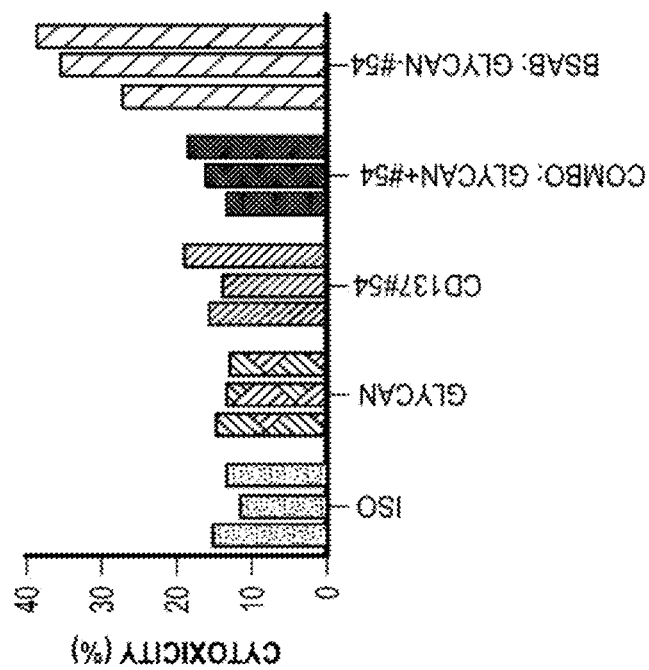
FIGS. 22A-22B show that anti-glycan-CD137 #54 bsAb induces IFN-γ production (left panel of FIG. 22A and FIG. 22B) and cancer cell cytotoxicity (right panel of FIG. 22A) of CD8 T cells upon coculturing with glycan-positive cancer cells.
Figure 22A:
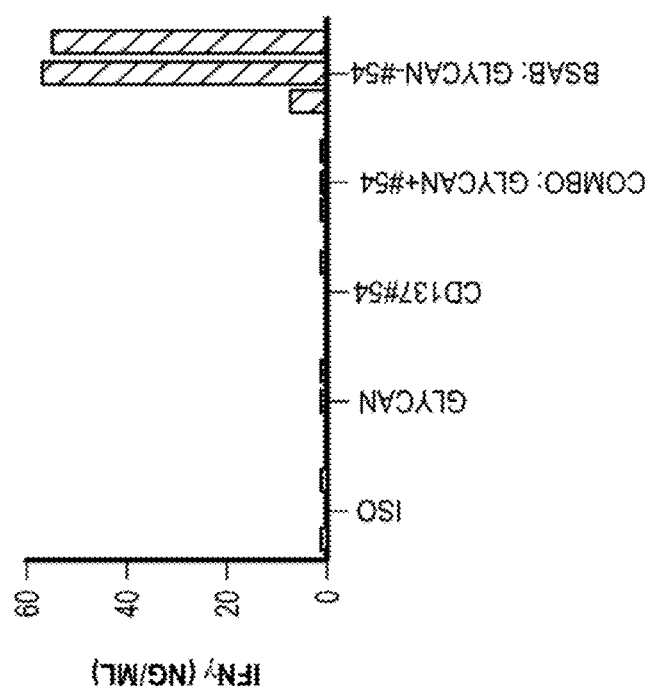
Figure 22B:
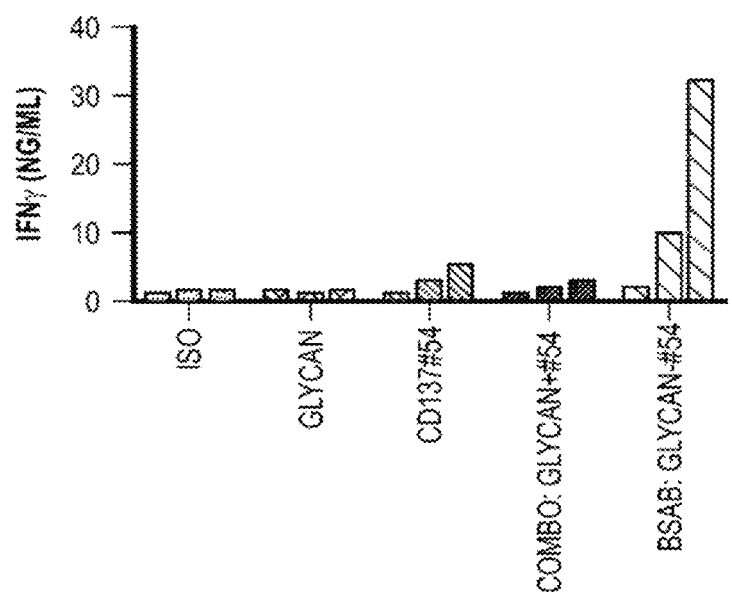

More robust IFN-γ production was induced by anti-PD-L1 #6-CD137 #54 bsAb compared to the mono- or combination therapy with anti-PD-L1 #6 and anti-CD137 #54 antibodies (FIGS. 20A-20C). Higher tumor cell cytotoxicity of CD8 T cells was observed in coculture with PC-3 cells (FIG. 20B). In addition to PD-L1-positive tumors, Her2-positive (SKBR-3 and MDA-MB-361) and glycan-positive (MCF-7 and NCI-N87) tumor cells targeted by anti-Her2 (Trastuzumab or #3-7) and anti-tumor glycan antibodies conjugated to CD137 #54 scFv also resulted in much stronger IFN-γ production (FIGS. 21A-21B and FIGS. 22A-22B) and tumor cell cytotoxicity (FIG. 22A) of CD8 T cells compared to mono- or combination therapy.

These results show that target-dependent T-cell activation was specifically induced by tumor-targeted CD137 #54 bsAb.

Example 17

This example illustrates induction of CD137 internalization by anti-PD-L1 #6-CD137 #54 bispecific antibody.

To test whether CD137 internalization is also induced by anti-PD-L1 #6-CD137 #54 bispecific antibody as well as the reference antibodies Urelumab and Utoliumab, an internalization assay was carried out with CD137 expressing HEK293 cells (FIG. 23). 5×10$^4$ CD137 expressing cells per well were pre-seeded on a black 96-well plate with Dulbecco's Modified Eagle Medium (Invitrogen) containing 10% fetal bovine serum (Gibco) and incubated overnight at 37° C., 5% $CO_2$. Antibodies as indicated were labeled with pHAb Amine Reactive dye (Promega Corp.) according to the manufacturer's protocol and then prepared as a 3-fold serial dilution from 100 nM in medium. The medium of pre-seeded cells was then replaced with medium containing labeled antibodies and cells were cultured for another 24 hours in the incubator. After incubation, cells were rinsed and kept in PBS for fluorescence recording by SpectraMax iD3. The EC50 value was calculated using GraphPad Prism. As shown in FIG. 23, stronger CD137 internalization induction was observed with anti-PD-L1 #6-CD137 #54 bispecific antibody treatment compared to treatment with reference anti-CD137 antibodies. Without being limited by theory, the level of CD137 internalization may reduce CD137 activation if the bispecfic Ab binds to the T cell through CD137 engagement alone. Accordingly, a lower toxicity may be seen with the bispecific antibody compared to reference antibodies, and especially compared to Urelumab, upon administration of the bispecific antibody in vivo.

Example 18

This example illustrates rescue of Treg cell-mediated inhibition of T cell proliferation by anti-PD-L1 #6-CD137 #54 bispecific antibody.

Figure 24A:
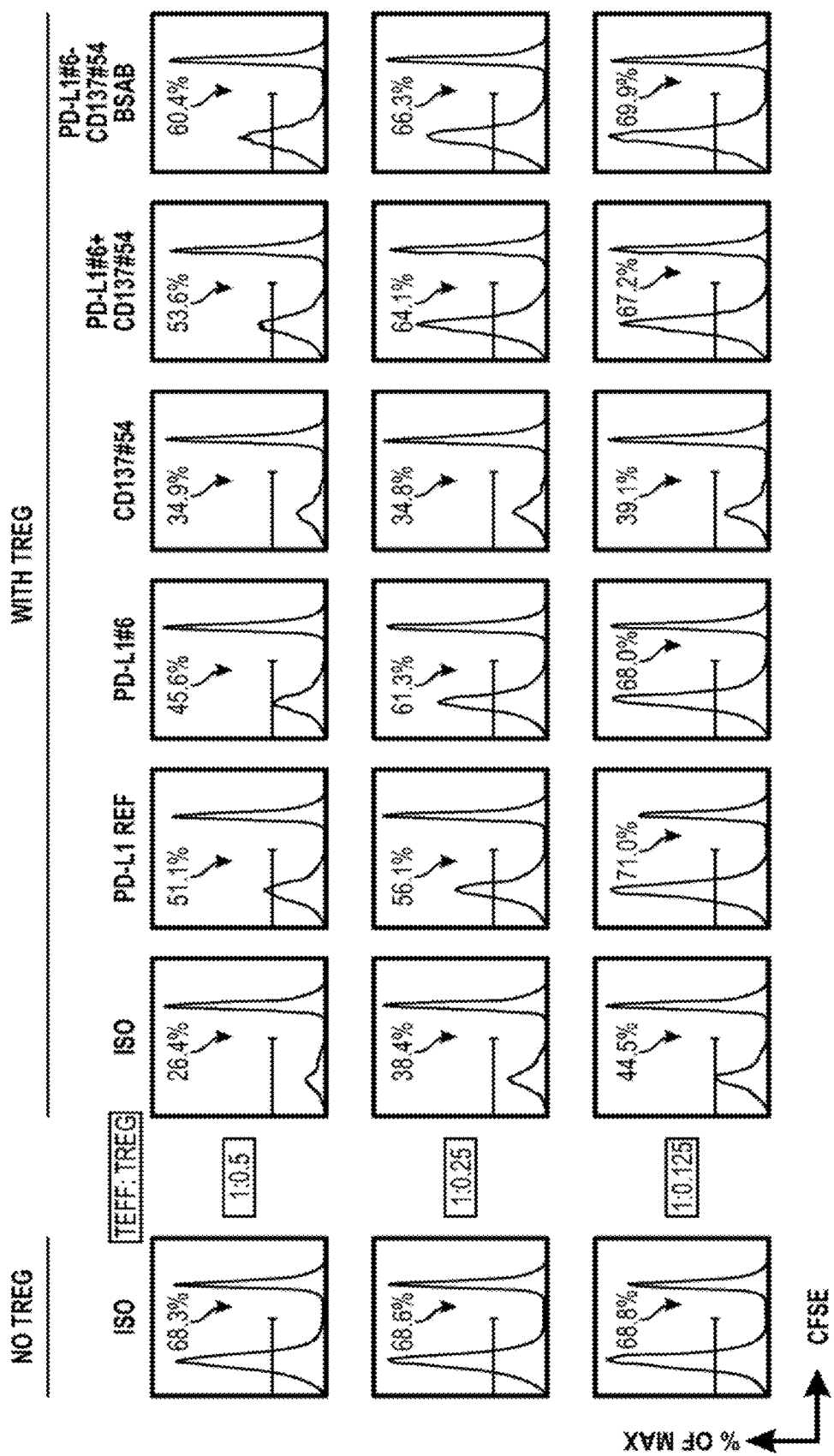
FIGS. 24A-24B show that anti-PD-L1 #6-CD137 #54 bsAb rescued T-cell proliferation (FIG. 24A) and cytokine production (FIG. 24B) in the presence of Treg cells.
Figure 24B:
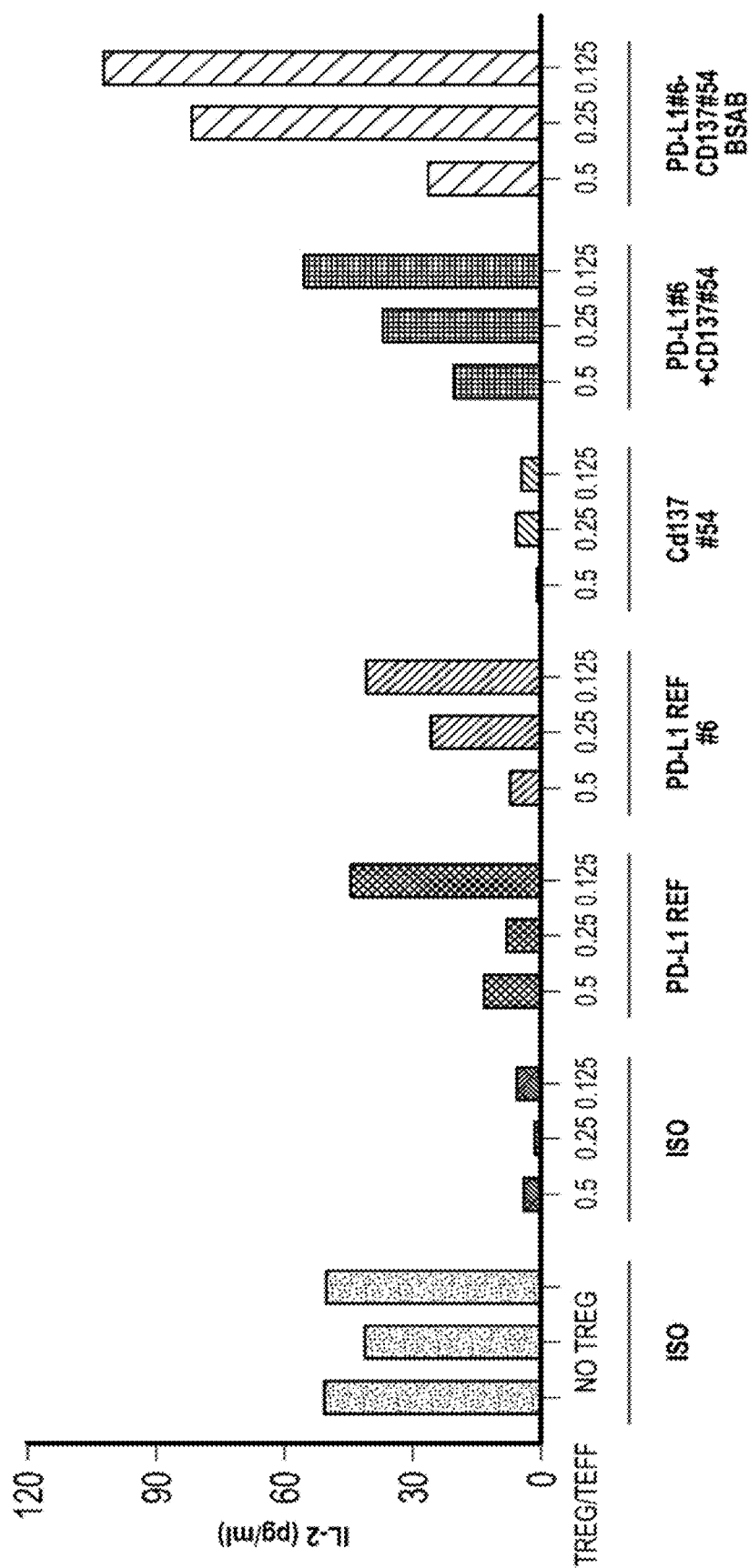

A Treg suppression assay was established using a mixed lymphocyte reaction as described in Example 12. Treg cells were isolated from peripheral blood using an EasySep™ Human CD4+CD127$^{low}$CD25+ Regulatory T Cell Isolation Kit (STEMCELL, Catalog no. 18063) and expanded using Dynabeads® Human Treg Expander (Gibco, Catalog no. 11129D). Expanded Treg cells greatly suppressed the proliferation and IL-2 production of CD4 T cells. The suppressive activity of Treg cells was abolished by adding anti-PD- L1 #6-CD137 #54 bsAb to the culture (FIGS. 24A-24B). Anti-PD-L1 #6-CD137 #54 bsAb rescued both T-cell proliferation (FIG. 24A) and cytokine production (FIG. 24B) in the presence of Treg cells. These results show that anti-PD-L1 #6-CD137 #54 bsAb was able to rescue T-reg mediates suppression of T-cell activation.

Example 19

This example illustrates inhibition of tumor growth by anti-PD-L1 #6-CD137 #54 bispecific antibody in vivo.

Figure 25A:
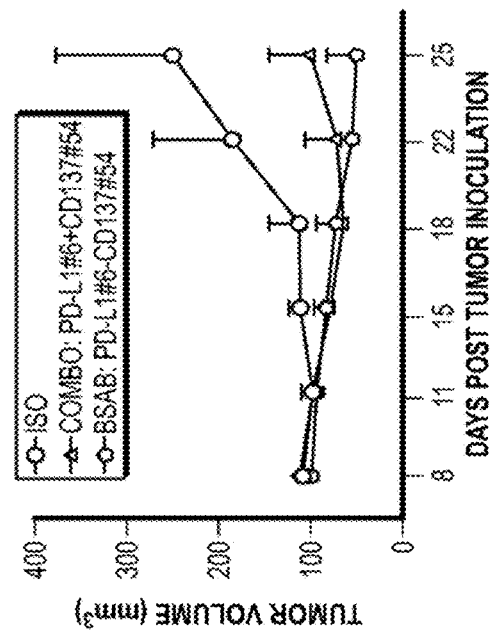
FIGS. 25A-25C show that anti-PD-L1 #6-CD137 #54 bsAb results in greater tumor growth inhibition compared to combination treatment with anti-PD-L1 #6 and anti-CD137 #54 antibodies in humanized mice xenografted with PD-L1-positive (FIG. 25A) NCI-H292, (FIG. 25B) NCI-H1975, and (FIG. 25C) BxPC-3 tumor cells.
Figure 25B:
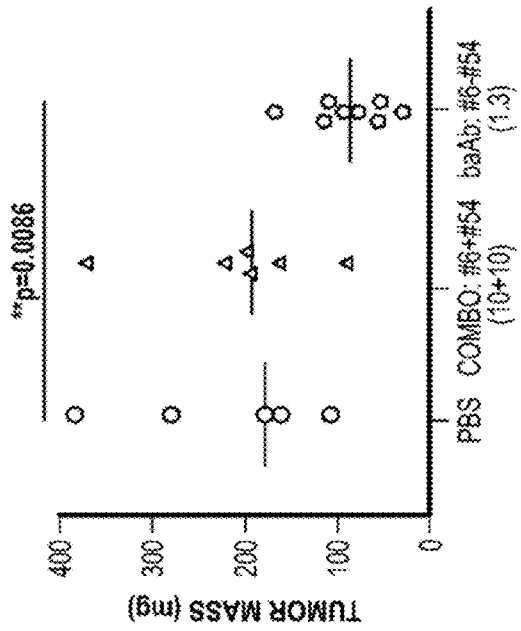
Figure 25C:
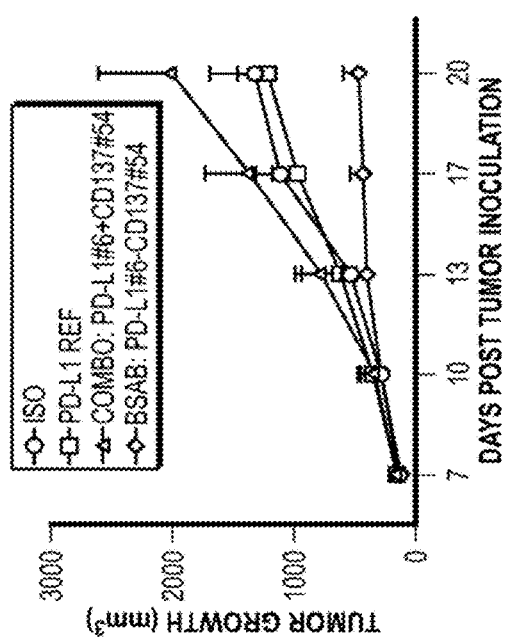
Figure 25C:
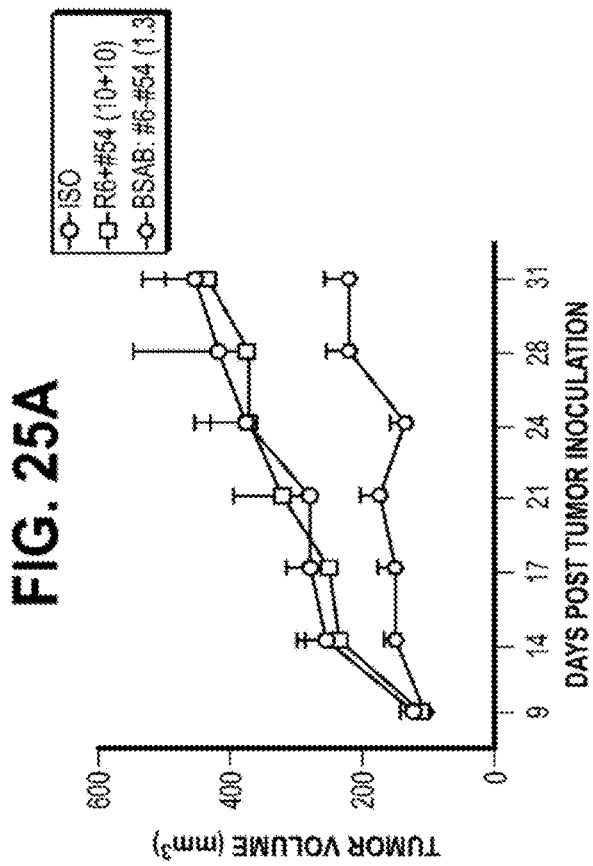

To validate the anti-tumor activity of anti-PD-L1 #6-CD137 #54 bsAb, which does not cross-react with mouse PD-L1 and mouse CD137, human tumor cells (NCI-H292, NCI-H1975 and BxPC-3) were premixed with human PBMC and xenografted subcutaneously to SCID-beige mice to evaluate anti-cancer activity in vivo. Seven days post tumor inoculation, equal moles of mAb (M.W. 150 kDa, 1 mg/kg) and bsAb (M.W. 195 kDa, 1.3 mg/kg) were intraperitoneally injected twice per week. Tumor sizes (mm³) were measured twice per week and calculated as (length× width×width)/2. The tumor growth inhibition index (TGI) of anti-PD-L1 #6-CD137 #54 bsAb (TGI: 67.5%) was greater than that of MPDL-3280a (TGI: 44.3%) and the combination of PD-L1 #6+CD137 #54 (TGI: −18.77%) in the NCI-H292 tumor model (FIG. 25A). Similarly, the TGI of anti-PD-L1 #6-CD137 #54 bsAb (TGI: 80%) was greater than that of the combination of PD-L1 #6+CD137 #54 (TGI: 67.2%) in the NCI-H1975 tumor model (FIG. 25B). In addition to lung cancers, anti-PD-L1 #6-CD137 #54 bsAb also showed greater anti-tumor activity (TGI of 1.3 mg/kg was 43%) compared to combination therapy (TGI of 10 mg/ml each: −9.2%) in the BxPC-3 pancreatic cancer model (FIG. 25C). Thus, anti-PD-L1 #6-CD137 #54 bsAb showed anti-tumor activity in two different cancer models in vivo.

In summary, these results show greater inhibition of tumor growth upon treatment with anti-PD-L1 #6-CD137 #54 bsAb compared to combination treatment with anti-PD-L1 and anti-CD137 antibodies in xenograft tumor models in mice.

Example 20

This example illustrates cytokine release in the presence of bispecific antibodies in vitro.

Figure 26:
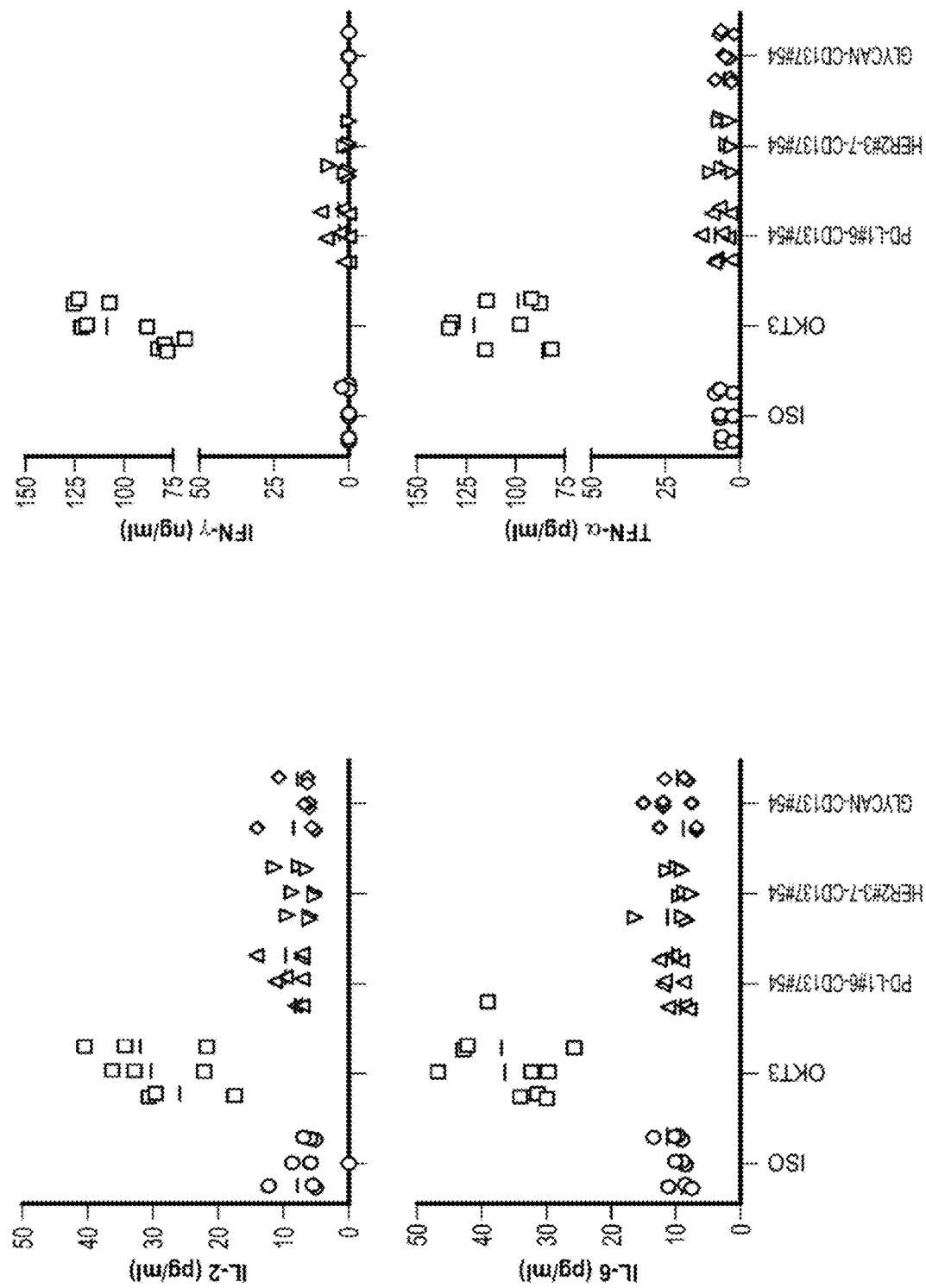
FIG. 26 shows that PD-L1 #6-CD137 #54, Her2 #3-7-CD137 #54 and glycan-CD137 #54 bsAbs do not induce noticeable cytokine release in human PBMC.
Figure 26:
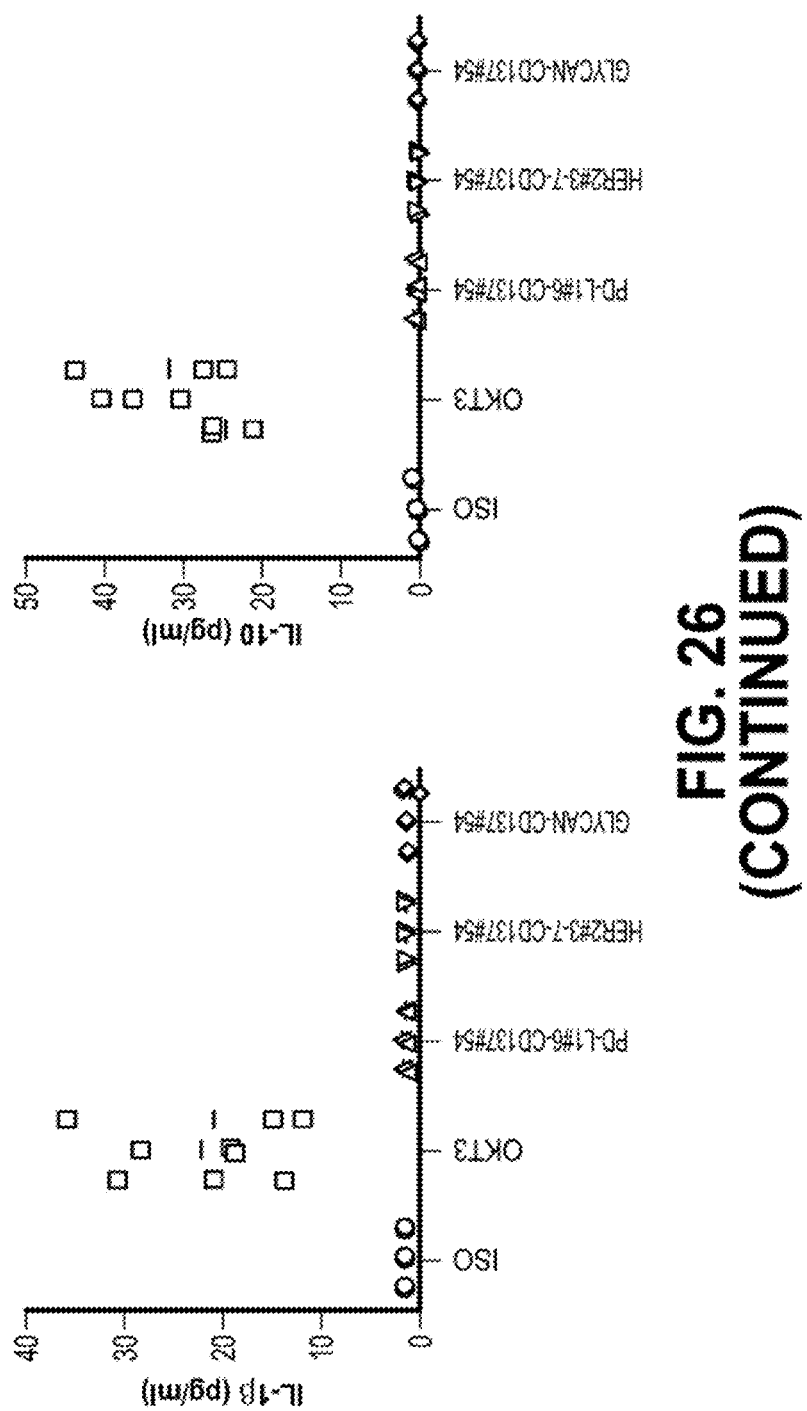

Human PBMCs from three donors were incubated with isotype, anti-CD3 antibody (OKT3, as positive control), and three bispecific antibodies (anti-PD-L1 #6, anti-Her2 #3-7, and anti-glycan conjugated to CD137 #54 scFv) at 0.67, 6.67, and 66.67 nM for 24 hours. Cytokines released into the culture medium were detected by the multiplex ProcartaPlex™ Immunoassay (ThermoFisher Scientific). A profound cytokine release was induced by OKT3, while the three bispecific antibodies did not induce cytokine release (FIG. 26).

These results show that, compared to OKT3, PD-L1 #6-CD137 #54, Her2 #3-7-CD137 #54 and glycan-CD137 #54 bsAbs did not induce noticeable cytokine release above background when incubated with human PBMC.

Example 21

This example illustrates pharmacokinetic parameters of an anti-PD-L1 #6-CD137 #54 bispecific antibody in rhesus monkeys.

Figures 27A, 27B:
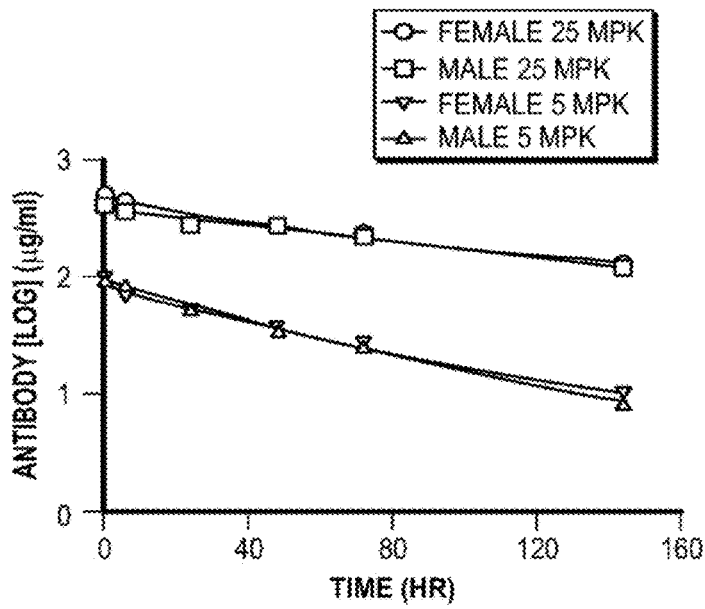
FIGS. 27A-27B show PK parameters of anti-PD-L1 #6-CD137 #54 bsAb in monkeys as (FIG. 27A) a graph and (FIG. 27B) in tabular form.

The bispecific anti-PD-L1 #6-CD137 #54 antibody (5 and 25 mg per kg body weight) was administered via an intravenous bolus injection to two groups (one male and one female per group) of rhesus monkeys. Peripheral blood was collected at 0.5, 6, 24, 48, 72, and 144 hours post injection. Plasma concentrations of the antibody were determined by ELISA. MaxiSorp plates (Invitrogen) were coated with CD137-Fc fusion protein (AP Biosciences, 1 µg/mL), followed by application of serially-diluted plasma samples and anti-PD-L1 #6-CD137 #54 bsAb as the standard curve. Bound antibodies were detected by biotinylated PD-L1-Fc fusion protein (AP Biosciences) and HRP-conjugated streptavidin using TMB substrate. Plasma antibody concentrations were calculated by the interpolation method. PK parameters were calculated using PKSolver software (Zhang, Huo, Zhou, & Xie, 2010). The $t_{1/2}$ of anti-PD-L1 #6-CD137 #54 bsAb were about 87 and 49 hours in the 25 mg/kg- and 5 mg/kg-injected groups, respectively (FIGS. 27A-27B), and no elevated levels of ALT/AST were observed during the experimental period (not shown).

SEQUENCES

SEQ ID NO 1: Anti-CD137 clone 15 heavy chain
QVQLVQSGAEVKKPGSSVKVSCKASGGTFSSYAISWVRQAPGQGLEWMGRIIPILGIANY
AQKFQGRVTITADKSTSTAYMELSSLRSEDTAVYYCASDLYQLLFPYYYGMDVWGQGTTV
TVSS SEQ ID NO 2: Anti-CD137 clone 15 light chain
QLVLTQPPSASASLGASVTLTCTLSSGYSNYKVDWYQQRPGKGPRFVMRVGTGGIVGSKG
DGIPDRFSVLGSGLNRYLTIKNIQEEDESDYHCGADHGSGSNLFWVFGGGTKLTVLGQPK
AAPSVTLFPPSSEELQANKATLVCLISDFYPGAVTVAWKADSSPVKAGVETTTPSKQSNN
KYAASSYLSLTPEQWKSHRSYSCQVTHEGSTVEKTVAPTECS SEQ ID NO 3: CDR-H1 of anti-CD137 clone 15
GGTFSSY SEQ ID NO 4: CDR-H2 of anti-CD137 clone 15
IPILGI SEQ ID NO 5: CDR-H3 of anti-CD137 clone 15
DLYQLLFPYYYGMDV SEQ ID NO 6: CDR-L1 of anti-CD137 clone 15
TLSSGYSNYKVD SEQ ID NO 7: CDR-L2 of anti-CD137 clone 15
VGTGGIVGSKGD SEQ ID NO 8: CDR-L3 of anti-CD137 clone 15
GADHGSGSNLFWV SEQ ID NO 9: Anti-CD137 clone 31 heavy chain
QVQLVQSGAEVKKPGASVKVSCKASGYTFTGYYMHWVRQAPGQGLEWMGWINPNSGGTNY
AQKFQGRVTMTRDTSISTAYMELSRLRSDDTAVYYCARDLRGAFDPWGQGTTVTVSS SEQ ID NO 10: Anti-CD137 clone 31 light chain
QSALTQPASVSGSPGQSITISCTGTSSDVGAYNFVSWYQQRPGKAPELMIYDVSDRPSGV
SNRFSGSKSGNTASLTISGLQTEDEADYYCSSYTSSITRYVFGTGTKVTVLGQPKANPTV
TLFPPSSEELQANKATLVCLISDFYPGAVTVAWKADGSPVKAGVETTKPSKQSNNKYAAS
SYLSLTPEQWKSHRSYSCQVTHEGSTVEKTVAPTECS SEQ ID NO 11: CDR-H1 of anti-CD137 clone 31
GYTFTGY SEQ ID NO 12: CDR-H2 of anti-CD137 clone 31
NPNSGG SEQ ID NO 13: CDR-H3 of anti-CD137 clone 31
DLRGAFDP SEQ ID NO 14: CDR-L1 of anti-CD137 clone 31
TGTSSDVGAYNFVS SEQ ID NO 15: CDR-L2 of anti-CD137 clone 31
DVSDRPS SEQ ID NO 16: CDR-L3 of anti-CD137 clone 31
SSYTSSITRYV SEQ ID NO 17: Anti-CD137 clone 54 heavy chain
QVQLVQSGAEVKKPGSTVKVSCKASGGTFSSYAISWVRQAPGQGLEWMGRIIPILGIANY
AQKFQGRVTITADKSTSTAYMELSSLRSEDTAVYYCASPPYYDSSGYYPLGAFDIWGQGT
MVTVSS SEQ ID NO 18: Anti-CD137 clone 54 light chain
SYELTQPPSVSVSPGQTASITCSGDKLGEKYASWYQQKAGQSPILVIYQDSKRPSGIPER
FSGSNSGNTATLTISGLQAGDEADYYCQAWDGSSTYVFGTGTKVTVFGQPKANPTVTLFP
PSSEELQANKATLVCLISDFYPGAVTVAWKADGSPVKAGVETTKPSKQSNNKYAASSYLS
LTPEQWKSHRSYSCQVTHEGSTVEKTVAPTECS SEQ ID NO 19: CDR-H1 of anti-CD137 clone 54
GGTFSSY SEQ ID NO 20: CDR-H2 of anti-CD137 clone 54
IPILGI SEQ ID NO 21: CDR-H3 of anti-CD137 clone 54
PPYYDSSGYYPLGAFDI SEQ ID NO 22: CDR-L1 of anti-CD137 clone 54
SGDKLGEKYAS SEQ ID NO 23: CDR-L2 of anti-CD137 clone 54
QDSKRPS SEQ ID NO 24: CDR-L3 of anti-CD137 clone 54
QAWDGSSTYV SEQ ID NO 25: constant domain in heavy chain (IgG4)
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSLGK SEQ ID NO 26: constant domain in heavy chain (engineered IgG1)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCAVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPG

| SEQUENCES |
|---|

SEQ ID NO 27: SP1
METDTLLLWVLLLWVPGSTG

SEQ ID NO 28: GS linker
GGGGS

SEQ ID NO 29: (G4S)2 linker
GGGGSGGGGS

SEQ ID NO 30: Anti-PD-L1#6 Light Chain
QSVLTQPPSASGTPGQRVTISCSGSSSNIGSNTVNWYQQLPGTAPKLLIYSNNQRPSGVP
DRESGSKSGTSASLAISGLQSEDEADYYCATWDLSLNAWVVFGGGTKLTVLGQPKAAPSV
TLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS SEQ ID NO 31: Anti-PD-L1 #6-CD137 #31 bsAb Heavy Chain
QVQLVQSGAEVKKPGSSVKVSCKASGGTFRRYSISWVRQAPGQGLEWMGGIIPVFGAAKY
AQKFQGRVTITADEFTSTAYMELSSLTSEDTAVYYCALSGDSDAFDIWGQGTMVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCAVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGGGGSGGGGQSALTQPASVSGSPGQSITISCTG
TSSDVGAYNFVSWYQQRPGKAPELMIYDVSDRPSGVSNRFSGSKSGNTASLTISGLQTED
EADYYCSSYTSSITRYVFGTGTKVTVLGGGGSGGGGSGGGGSQVQLVQSGAEVKKPGASV
KVSCKASGYTFTGYYMHWVRQAPGQGLEWMGWINPNSGGTNYAQKFQGRVTMTRDTSIST
AYMELSRLRSDDTAVYYCARDLRGAFDPWGQGTTVTVSSA SEQ ID NO 32: Anti-PD-L1#6-CD137 #54 bsAb Heavy Chain
QVQLVQSGAEVKKPGSSVKVSCKASGGTFRRYSISWVRQAPGQGLEWMGGIIPVFGAAKY
AQKFQGRVTITADEFTSTAYMELSSLTSEDTAVYYCALSGDSDAFDIWGQGTMVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCAVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGGGGSGGGGSQVQLVQSGAEVKKPGSTVKVSCK
ASGGTFSSYAISWVRQAPGQGLEWMGRIIPILGIANYAQKFQGRVTITADKSTSTAYMEL
SSLRSEDTAVYYCASPPYYDSSGYYPLGAFDIWGQGTMVTVSSAGGGGSGGGGSGGGGSG
GGGSSYELTQPPSVSVSPGQTASITCSGDKLGEKYASWYQQKAGQSPILVIYQDSKRPSG
IPERFSGSNSGNTATLTISGLQAGDEADYYCQAWDGSSTYVFGTGTKVTVLG SEQ ID NO 33: CD137#31-scFv
QSALTQPASVSGSPGQSITISCTGTSSDVGAYNFVSWYQQRPGKAPELMIYDVSDRPSGV
SNRFSGSKSGNTASLTISGLQTEDEADYYCSSYTSSITRYVFGTGTKVTVLGGGGSGGGG
SGGGGSQVQLVQSGAEVKKPGASVKVSCKASGYTFTGYYMHWVRQAPGQGLEWMGWINPN
SGGTNYAQKFQGRVTMTRDTSISTAYMELSRLRSDDTAVYYCARDLRGAFDPWGQGTTVT
VSSA SEQ ID NO 34: CD137#54-scFv
QVQLVQSGAEVKKPGSTVKVSCKASGGTFSSYAISWVRQAPGQGLEWMGRIIPILGIANY
AQKFQGRVTITADKSTSTAYMELSSLRSEDTAVYYCASPPYYDSSGYYPLGAFDIWGQGT
MVTVSSAGGGGSGGGGSGGGGSGGGGSSYELTQPPSVSVSPGQTASITCSGDKLGEKYAS
WYQQKAGQSPILVIYQDSKRPSGIPERFSGSNSGNTATLTISGLQAGDEADYYCQAWDGS
STYVFGTGTKVTVLG SEQ ID NO 35: Trastuzumab Light Chain
DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC SEQ ID NO 36: Trastuzumab-CD137 #54 bsAb Heavy Chain
EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCAVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGGGGSGGGGSQVQLVQSGAEVKKPGSTVKVS
CKASGGTFSSYAISWVRQAPGQGLEWMGRIIPILGIANYAQKFQGRVTITADKSTSTAYM
ELSSLRSEDTAVYYCASPPYYDSSGYYPLGAFDIWGQGTMVTVSSAGGGGSGGGGSGGGG
SGGGGSSYELTQPPSVSVSPGQTASITCSGDKLGEKYASWYQQKAGQSPILVIYQDSKRP
SGIPERFSGSNSGNTATLTISGLQAGDEADYYCQAWDGSSTYVFGTGTKVTVLG

SEQUENCES

SEQ ID NO 37: Anti-Her2 #3-7 Light Chain
QTVVTQEPSFSVSPGGTVTLTCGLSSGSVSTSYYPSWYQQTPGQAPRTLIYSTNTRSSGV
PDRFSGSILGNKAALTITGAQADDESDYYCVLYMGSGIWVFGGGTKLTVLGQPKAAPSVT
LFPPSSEELQANKATLVCLISDFYPGAVTVAWKADSSPVKAGVETTTPSKQSNNKYAASS
YLSLTPEQWKSHRSYSCQVTHEGSTVEKTVAPTECS SEQ ID NO 38: Anti-Her2 #3-7-CD137 #54 bsAb Heavy Chain
EVQLVQSGAEVKKPGESLKISCKGSGYSFTSYWIGWVRQMPGKGLEWMGIIYPGDSDTRY
SPSFQGQVTISADKSISTAYLQWSSLKASDTAMYYCARQDNWNHGPYDAFDIWGQGTMVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREE
QYASTYRVVSVLTVLHQDWLNGKEYKCAVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGGGGSGGGGSQVQLVQSGAEVKKPGSTV
KVSCKASGGTFSSYAISWVRQAPGQGLEWMGRIIPILGIANYAQKFQGRVTITADKSTST
AYMELSSLRSEDTAVYYCASPPYYDSSGYYPLGAFDIWGQGTMVTVSSAGGGGSGGGGSG
GGGSGGGGSSYELTQPPSVSVSPGQTASITCSGDKLGEKYASWYQQKAGQSPILVIYQDS
KRPSGIPERFSGSNSGNTATLTISGLQAGDEADYYCQAWDGSSTYVFGTGTKVTVLG SEQ ID NO 39: Anti-Glycan Light Chain
EIVLTQSPSTLSLSPGERATLSCQASEDVSYMHWYQQKPGQAPQPWIYGTSNKASGVPSR
FSGSGSGTDFTLTISSLQPEDVATYYCQQWSRRPFTFGQGTKVEIKRTVAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSENRGEC SEQ ID NO 40: Anti-Glycan-CD137 #54 bsAb Heavy Chain
QITLQESGPTLVKPTQTLTLTCTESGFSLYRFDMGVGWIRQPPGQGLEWLAHIWWDDDKY
YNPALKSRLTISKDTSKNQVVLTMTNMDPVDTATYYCARVGLHDYYYFAYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREE
QYASTYRVVSVLTVLHQDWLNGKEYKCAVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGGGGSGGGGSQVQLVQSGAEVKKPGSTV
KVSCKASGGTESSYAISWVRQAPGQGLEWMGRIIPILGIANYAQKFQGRVTITADKSTST
AYMELSSLRSEDTAVYYCASPPYYDSSGYYPLGAFDIWGQGTMVTVSSAGGGGSGGGGSG
GGGSGGGGSSYELTQPPSVSVSPGQTASITCSGDKLGEKYASWYQQKAGQSPILVIYQDS
KRPSGIPERFSGSNSGNTATLTISGLQAGDEADYYCQAWDGSSTYVFGTGTKVTVLG SEQ ID NO 41: CDR-H1 of anti-Her2#3-7
GYSFTSY SEQ ID NO 42: CDR-H2 of anti-Her2#3-7
YPGDSD SEQ ID NO 43: CDR-H3 of anti-Her2#3-7
QDNWNHGPYDAFDI SEQ ID NO 44: CDR-L1 of anti-Her2#3-7
GLSSGSVSTSYYPS SEQ ID NO 45: CDR-L2 of anti-Her2#3-7
STNTRSS SEQ ID NO 46: CDR-L3 of anti-Her2#3-7
VLYMGSGIWV

TABLE 1

Sequences of Defined CDR Regions of Monoclonal Antibodies and Single Chain Variable Fragments (scFv) of Bispecific Antibodies.

| Name | Sequences | | |
|---|---|---|---|
| | CDR1 | CDR2 | CDR3 |
| CD137#15-H | GGTFSSY (SEQ ID NO: 3) | IPILGI (SEQ ID NO: 4) | DLYQLLFPYYYGMDV (SEQ ID NO: 5) |
| CD137#15-L | TLSSGYSNYKVD (SEQ ID NO: 6) | VGTGGIVGSKGD (SEQ ID NO: 7) | GADHGSGSNLFW (SEQ ID NO: 8) |

TABLE 1-continued

Sequences of Defined CDR Regions of Monoclonal Antibodies and Single Chain Variable Fragments (scFv) of Bispecific Antibodies.

| Name | CDR1 | CDR2 | CDR3 |
|---|---|---|---|
| CD137#31-H | GYTFTGY (SEQ ID NO: 11) | NPNSGG (SEQ ID NO: 12) | DLRGAFDP (SEQ ID NO: 13) |
| CD137#31-L | TGTSSDVGAYNFVS (SEQ ID NO: 14) | DVSDRPS (SEQ ID NO: 15) | SSYTSSITRYV (SEQ ID NO: 16) |
| CD137#54-H | GGTFSSY (SEQ ID NO: 19) | IPILGI (SEQ ID NO: 20) | PPYYDSSGYYPLGAFDI (SEQ ID NO: 21) |
| CD137#54-L | SGDKLGEKYAS (SEQ ID NO: 22) | QDSKRPS (SEQ ID NO: 23) | QAWDGSSTYV (SEQ ID NO: 24) |
| Her2#3-7-H | GYSFTSY (SEQ ID NO: 41) | YPGDSD (SEQ ID NO: 42) | QDNWNHGPYDAFDI (SEQ ID NO: 43) |
| Her2#3-7-L | GLSSGSVSTSYYPS (SEQ ID NO: 44) | STNTRSS (SEQ ID NO: 45) | VLYMGSGIWV (SEQ ID NO: 46) |
| CD137#31-scFv | QSALTQPASVSGSPGQSITISCTGTSSDVGAYNFVSWYQQRPGKAPELMIYDVSDRPSGVSNRFSGSKSGNTASLTISGLQTEDEADYYCSSYTSSITRYVFGTGTKVTVLGGGGSGGGGSGGGGSQVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDLRGAFDPWGQGTTVTVSSA (SEQ ID NO: 33) | | |
| CD137#54-scFv | QVQLVQSGAEVKKPGSTVKVSCKASGGTFSSYAISWVRQAPGQGLEWMGRIIPILGIANYAQKFQGRVTITADKSTSTAYMELSSLRSEDTAVYYCASPPYYDSSGYYPLGAFDIWGQGTMVTVSSAGGGGSGGGGSGGGGSGGGGSSYELTQPPSVSVSPGQTASITCSGDKLGEKYASWYQQKAGQSPILVIYQDSKRPSGIPERFSGSNSGNTATLTISGLQAGDEADYYCQAWDGSSTYVFGTGTKVTVLG (SEQ ID NO: 34) | | |

REFERENCES

Kwon, B. S., & Weissman, S. M. (1989). cDNA sequences of two inducible T-cell genes. *Proc Natl Acad Sci USA*, 86(6), 1963-1967.

Zhang, Y., Huo, M., Zhou, J., & Xie, S. (2010). PKSolver: An add-in program for pharmacokinetic and pharmacodynamic data analysis in Microsoft Excel. *Comput Methods Programs Biomed*, 99(3), 306-314. doi: 10.1016/j.cmpb.2010.01.007

Chin, S. M. et al. (2018). Structure of the 4-1BB/4-1BBL complex and distinct binding and functional properties of utomilumab and urelumab. *Nature Communications* 9:4679. DOI: 10.1038/s41467-018-07136-7

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.1, 2.2, 2.7, 3, 4, 5, 5.5, 5.75, 5.8, 5.85, 5.9, 5.95, 5.99, and 6. This applies regardless of the breadth of the range.

Although the invention has been described with reference to the above examples, it will be understood that modifications and variations are encompassed within the spirit and scope of the invention. Accordingly, the invention is limited only by the following claims.

What is claimed is:

1. A bispecific antibody comprising a first antigen binding region and a second antigen binding region,
   wherein the first antigen binding region binds to CD137, and
   wherein the first antigen binding region comprises:
   (i) heavy chain variable (V$_H$) complementarity determining region (CDR)-H1, CDR-H2, and CDR-H3, wherein CDR-H1 comprises the amino acid sequence of SEQ ID NO:19, CDR-H2 comprises the amino acid sequence of SEQ ID NO:20, and CDR-H3 comprises the amino acid sequence of SEQ ID NO:21; and
   (ii) light chain variable (VL) CDR-L1, CDR-L2, and CDR-L3, wherein CDR-L1 comprises the amino acid sequence of SEQ ID NO:22, CDR-L2 comprises the amino acid sequence of SEQ ID NO:23, and CDR-L3 comprises the amino acid sequence of SEQ ID NO:24.

2. The bispecific antibody of claim 1 wherein the antibody comprises:
   a V$_H$ region comprising an amino acid sequence comprising SEQ ID NO: 17 and a V$_L$ region comprising an amino acid sequence comprising SEQ ID NO: 18;
   wherein the second antigen binding region binds to an immune checkpoint molecule, an immune stimulatory molecule, or a tumor antigen.

3. The bispecific antibody of claim 1, wherein the antibody comprises:
   (i) a heavy chain sequence of SEQ ID NO:32 and a light chain sequence of SEQ ID NO: 30,
   (ii) a heavy chain sequence of SEQ ID NO:36 and a light chain sequence of SEQ ID NO: 35,
   (iii) a heavy chain sequence of SEQ ID NO:38 and a light chain sequence of SEQ ID NO: 37, or
   (iv) a heavy chain sequence of SEQ ID NO:40 and a light chain sequence of SEQ ID NO: 39.

4. The bispecific antibody of claim 1, wherein the second antigen binding region binds to an antigen selected from PD-L1, PD-1, CTLA-4, LAG3, CD28, CD40, CD137, CD27, ICOS, Her2, or a glycan.

5. The bispecific antibody of claim 1, wherein the first antigen binding region and the second antigen binding region comprise an scFv, an F (ab) 2, a Fab, or any combination thereof.

6. The bispecific antibody of claim 5, wherein the first antigen binding region comprises an scFv and wherein the second antigen binding region comprises a Fab.

7. A bispecific antibody comprising a first antigen binding region and a second antigen binding region,
   wherein the first antigen binding region binds to CD137,
   wherein the first antigen binding region comprises an scFv and wherein the second antigen binding region comprises a Fab, and
   wherein the scFv comprises: a V$_H$ region comprising an amino acid sequence comprising SEQ ID NO: 17 and a V$_L$ region comprising an amino acid sequence of about 100 to 120 amino acids of an N-terminal sequence of SEQ ID NO: 18.

8. The bispecific antibody of claim 7, wherein the scFv comprises the amino acid sequence of SEQ ID NO:34.

9. The bispecific antibody of claim 8, further comprising an Fc domain:
   (i) wherein the scFv is linked to the C-terminus of the Fc domain
   and/or
   (ii) wherein there is a linker between the Fc domain and the scFv and wherein the Fab is linked to the N-terminus of the Fc domain.

* * * * *